(12) United States Patent
Schnermann et al.

(10) Patent No.: US 11,707,537 B2
(45) Date of Patent: *Jul. 25, 2023

(54) CONFORMATIONAL RESTRICTION OF CYANINE FLUOROPHORES IN FAR-RED AND NEAR-IR RANGE

(71) Applicant: The United States of America, as represented by the Secretary, Department of Health and Human Service, Bethesda, MD (US)

(72) Inventors: Martin J. Schnermann, Rockville, MD (US); Megan S. Michie, Frederick, MD (US)

(73) Assignee: The USA, as represented by the Secretary, Department of Health and Human Services, Bethesda, MD (US)

( * ) Notice: Subject to any disclaimer, the term of this patent is extended or adjusted under 35 U.S.C. 154(b) by 142 days.

This patent is subject to a terminal disclaimer.

(21) Appl. No.: 17/198,004

(22) Filed: Mar. 10, 2021

(65) Prior Publication Data

US 2021/0220490 A1    Jul. 22, 2021

Related U.S. Application Data

(63) Continuation of application No. 16/640,620, filed as application No. PCT/US2018/047876 on Aug. 24, 2018, now Pat. No. 10,994,029.

(60) Provisional application No. 62/549,566, filed on Aug. 24, 2017.

(51) Int. Cl.
*A61K 49/00* (2006.01)
*C07D 491/147* (2006.01)

(52) U.S. Cl.
CPC ...... *A61K 49/0032* (2013.01); *C07D 491/147* (2013.01); *A61K 2123/00* (2013.01)

(58) Field of Classification Search
CPC ............ A61K 49/0032; A61K 2123/00; C07D 491/147; C07D 491/22; C09B 23/0075; C09B 57/00
See application file for complete search history.

(56) References Cited

U.S. PATENT DOCUMENTS

| | | | |
|---|---|---|---|
| 6,133,445 | A | 10/2000 | Waggoner et al. |
| 9,349,964 | B2 | 5/2016 | Chun et al. |
| 10,280,307 | B2 | 5/2019 | Schnermann et al. |
| 10,561,729 | B2 | 2/2020 | Schnermann et al. |
| 2014/0110694 | A1 | 4/2014 | Shin et al. |

FOREIGN PATENT DOCUMENTS

| | | |
|---|---|---|
| EP | 0 670 374 A1 | 9/1995 |
| KR | 2012008324 | 7/2012 |
| WO | WO 1999/31181 | 6/1999 |
| WO | WO 2000/56933 | 9/2000 |
| WO | WO 2017/027721 | 2/2017 |

OTHER PUBLICATIONS

Cooper, Michael E., "Fluorescent Probes for Biological Applications: Cyanine Dyes Revisited," *Fluorescence Microscopy and Fluorescent Probes*, 17 pages, (1999).

(Continued)

*Primary Examiner* — Robert S Cabral
(74) *Attorney, Agent, or Firm* — Klarquist Sparkman, LLP

(57) ABSTRACT

Conformationally restricted cyanine fluorophores, as well as methods of making and using the compounds, are described. The conformationally restricted cyanine fluorophores have a chemical structure according to Formula I, or a stereoisomer or pharmaceutically acceptable salt thereof:

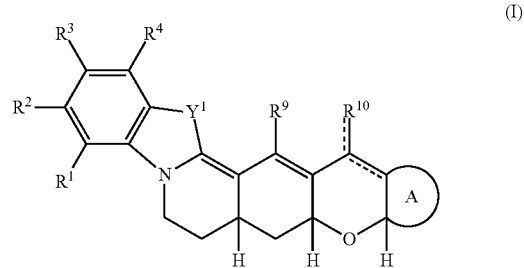

(I)

wherein A is

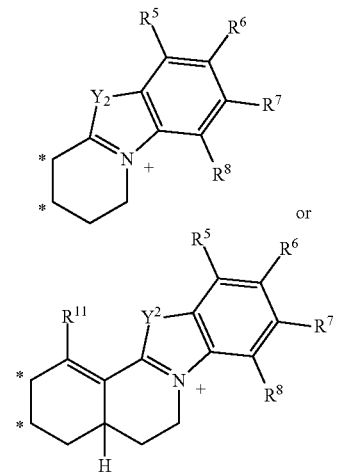

and wherein each "*" designates an attachment point of A.

20 Claims, 11 Drawing Sheets

(56) References Cited

OTHER PUBLICATIONS

Gorka et al., "A near-IR uncaging strategy based on cyanine photochemistry," *Journal of the American Chemical Society* 136: 14153 (2014), dx.doi.org/10.1021/ja5065203.

Michie et al., "Cyanine Conformational Restraint in the Far-Red Range," *Journal of the American Chemical Society* 139(6): 12406-12409 (Sep. 1, 2017).

Nani, et al., "N- to O- Rearrangement of Cyanines: Synthesis of Stable NIR Fluorophores," *Chemical Biology Laboratory, National Cancer Institute*, 1 page (Sep. 24, 2014).

Shershov et al., "Near-infrared heptamethine cyanine dyes. Synthesis, spectroscopic characterization, thermal properties and photo stability," *Dyes and pigments* 97(2): 353-360 (Jan. 16, 2013).

| Position | $\delta_H$ (mult., J in Hz) | $\delta_C$ |
|---|---|---|
| 2 | | 169.19 |
| 3 | | 49.07 or 48.33 |
| 4 | | 141.50 or 141.05 |
| 5-8 and 20-23 | 7.57 – 7.36 (m, 4H)<br>7.37 – 7.16 (m, 4H) | 128.30, 128.25, 125.27, 124.52, 121.90, 121.85, 110.23, 109.58 |
| 9 | | 142.01 or 141.97 |
| 10 | 4.40 – 4.24 (m, 2H)<br>3.88 (tq, J = 13.3, 4.5 Hz, 2H) | 42.90 |
| 11 | 2.41 (dt, J = 13.3, 4.2 Hz, 1H)<br>1.82 (dd, J = 12.6, 5.0 Hz, 1H) | 27.23 |
| 12 | 2.84 (tt, J = 12.3, 4.1 Hz, 1H) | 31.09 |
| 13 | 2.49 (dt, J = 11.7, 4.5 Hz, 1H)<br>1.48 (q, J = 11.8 Hz, 1H) | 35.05 |
| 14 | 4.61 (dd, J = 11.4, 5.0 Hz, 1H) | 72.20 |
| 15 | 4.67 (dd, J = 11.5, 5.0 Hz, 1H) | 70.16 |
| 16 | 2.58 (dt, J = 11.7, 4.5 Hz, 1H)<br>2.01 (qd, J = 12.6, 5.4 Hz, 1H) | 26.74 |
| 17 | 4.40 – 4.24 (m, 2H)<br>3.88 (tq, J = 13.3, 4.5 Hz, 2H) | 40.67 |
| 19 | | 142.01 or 141.97 |
| 24 | | 141.50 or 141.05 |
| 25 | | 49.07 or 48.33 |
| 26 | | 165.75 |
| 27 | | 111.42 |
| 28 | 7.93 (s) | 140.34 |
| 29 | | 128.74 |
| 30 | 7.86 (s) | 143.25 |
| 31 | | 114.03 |
| 32-35 | 1.78 – 1.74 (m, 12H) | 26.69, 26.57, 26.14, 25.99 |

| Position | δ_H (mult., J in Hz) | δ_C |
|---|---|---|
| 2 | | 169.39 |
| 3 | | 48.20 |
| 4 | | 139.97 |
| 5 | 7.89 (s, 1H) | 120.43 |
| 6 | | 145.08 |
| 7 | 7.69 (d, J = 8.1 Hz, 1H) | 124.91 |
| 8 | 7.36 (d, J = 8.2 Hz, 1H) | 109.32 |
| 9 | | 140.42 |
| 10 | 4.34 (d, J = 10.3 Hz, 1H) 3.89 (t, J = 11.7 Hz, 1H) | 42.10 |
| 11 | 2.28 (d, J = 12.9 Hz, 1H) 1.76 – 1.63 (m, 13H) - 1 | 25.60 |
| 12 | 2.75 (t, J = 12.4 Hz, 1H) | 29.23 |
| 13 | 1.34 (q, J = 11.8 Hz, 1H) 2.35 (dd, J = 7.0, 4.5 Hz, 1H) | 33.54 |
| 14 | 4.51 (dd, J = 11.3, 4.6 Hz, 1H) | 70.22 |
| 15 | 4.57 (dd, J = 11.4, 4.7 Hz, 1H) | 68.35 |
| 16 | 2.43 (d, J = 12.2 Hz, 1H) 1.88 (dd, J = 12.2, 5.0 Hz, 1H) | 25.36 |
| 17 | 4.24 (d, J = 9.5 Hz, 1H) 3.80 (t, J = 11.6 Hz, 1H) | 39.39 |
| 19 | | 143.92 |
| 20 | 7.23 (d, J = 8.3 Hz, 1H) | 107.86 |
| 21 | 7.95 (d, J = 8.2 Hz, 1H) | 129.19 |
| 22 | | 128.36 |
| 23 | 8.08 (s, 1H) | 122.08 |
| 24 | | 139.32 |
| 25 | | 46.29 |
| 26 | | 162.38 |
| 28 | 8.04 (s, 1H) | 142.87 |
| 30 | 7.99 (s, 1H) | 138.64 |
| 27, 29, 31 | | 118.79, 114.41, 109.74 |
| 32-35 | 1.76 – 1.63 (m, 13H) -12 | 26.30, 25.85 |
| 36 | | 166.29 |

CONFORMATIONAL RESTRICTION OF CYANINE FLUOROPHORES IN FAR-RED AND NEAR-IR RANGE

CROSS REFERENCE TO RELATED APPLICATIONS

This is a continuation of application Ser. No. 16/640,620, filed Feb. 20, 2020, issued as U.S. Pat. No. 10,994,029 B2, which claims priority to U.S. National Stage Application No. PCT/U2018/047876, filed Aug. 24, 2018, which was published in English under PCT Article 21(2), which in turn claims priority to U.S. provisional patent application No. 62/549,566 filed Aug. 24, 2017, all of which are incorporated by reference herein in their entirety.

FIELD

Conformationally restricted cyanine fluorophores are disclosed, and methods of making and using the conformationally restricted cyanine fluorophores.

BACKGROUND

Single molecule localization microscopy (SMLM) techniques like photoactivated localization microscopy (PALM) and direct stochastic optical reconstruction microscopy (dSTORM) enable three-dimensional (3D) imaging of cellular components with nearly molecular resolution. Localization precision, and therefore the structural resolution capability of SMLM, scales with the inverse square root of the single molecule emitter intensity. Consequently, SMLM fluorophores should provide high photon yields in the on state, while exhibiting low to absent background fluorescence in the off state.

Indocyanines are among the most useful fluorescent small molecules, uniquely spanning the visible to near-infrared (near-IR) range through successive 2-carbon homologation. Far-red variants, including Cy5 and Alexa 647, are the most common chemical component of dSTORM methods. However, fluorescence quantum yields ($\Phi_F$) are modest, typically below 0.2 in aqueous solution. Cyanine excited state deactivation involves trans- to cis-polyene rotation that competes extensively with photon emission. In the trimethine series, which emits in the green region of the spectrum, this pathway has been obstructed through a synthetic strategy involving installation of fused 6-membered rings along the polymethine bridge dramatically improving quantum yield. However, the synthetic strategy is not applicable to far-red cyanines, which require synthesis of a complex fused tetracyclic or pentacyclic ring system.

SUMMARY

Embodiments of conformationally restricted cyanine fluorophores, as well as methods of making and using the conformationally restricted cyanine fluorophores, are disclosed. Embodiments of the disclosed compounds have a chemical structure according to Formula I, or a stereoisomer or pharmaceutically acceptable salt thereof:

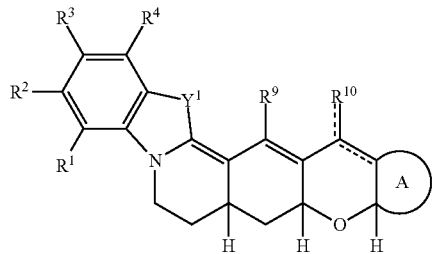

wherein A is

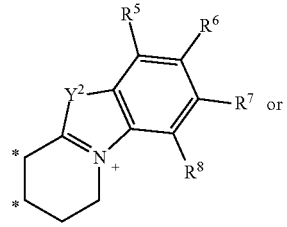

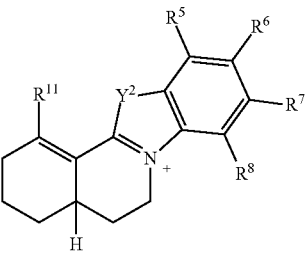

wherein each "*" designates an attachment point of A; the bonds represented by "----" are single or double bonds as needed to satisfy valence requirements; $R^1$-$R^9$ and $R^{11}$ independently are H, deuterium, alkyl, heteroalkyl, —N($R^a$)$_2$, sulfonate, alkyl sulfonate, amino, aminoalkyl, —C(O)O$R^a$, trityl, or a group comprising a conjugatable moiety, a targeting agent, or a drug, where each $R^a$ independently is H, deuterium, alkyl or heteroalkyl; $R^{10}$ is H, deuterium, O, alkyl, aryl, amino, sulfonate, triflate, —C(O)O$R^b$, —O$R^b$, —N($R^b$)$_2$, heteroalkyl, heteroaryl, trityl, or a group comprising a conjugatable moiety, a targeting agent, or a drug, where each $R^b$ independently is H, deuterium, alkyl, heteroalkyl, aryl, or heteroaryl; and $Y^1$ and $Y^2$ independently are C($R^c$)$_2$, N($R^d$), S, O, or Se, wherein each $R^c$ independently is H, deuterium, alkyl, —(OCH$_2$CH$_2$)$_x$OH where x is an integer ≥2, trityl, or a group comprising a conjugatable moiety, a targeting agent, or a drug, and each $R^d$ independently is H, deuterium, alkyl, or heteroalkyl.

In some embodiments, the compound has a chemical structure according to Formula IA, IB, IC, or ID:

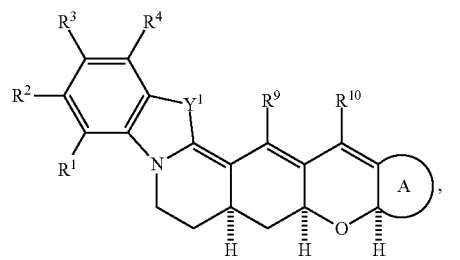
(IA)

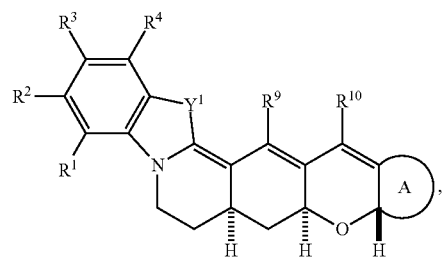
(IB)

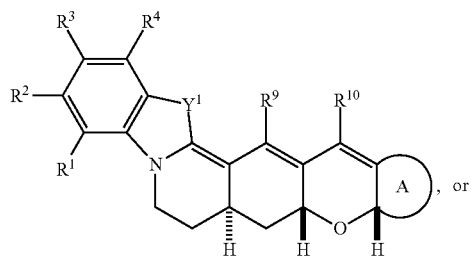
(IC)

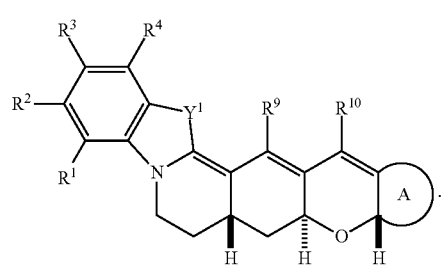
(ID)

In certain embodiments, the compound has a chemical structure according to Formula II or Formula III:

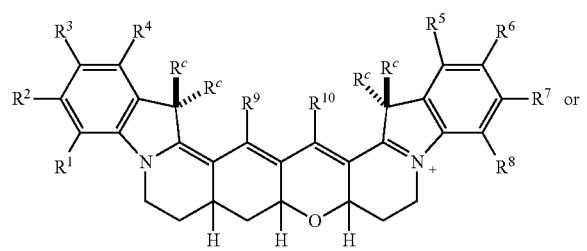
(II)

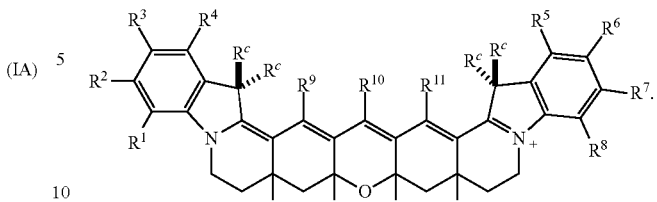
(III)

Embodiments of a pharmaceutical conformation comprise a compound according to Formula I and a pharmaceutically acceptable carrier.

Embodiments of a method for making a conformationally restricted pentamethine cyanine compound according to Formula I proceed via a cyclization cascade of a dialdehyde precursor, which is accessed through chemoselective olefin metathesis. The dialdehyde undergoes intramolecular Michael addition followed by a dihydropyran ring-forming cascade. Embodiments of a method for making a conformationally restricted heptamethine cyanine compound according to Formula I include combining an indolene precursor or two distinct indolenine precursors with a bis vinylogous amide to provide a heptamethine cyanine including pendant terminal alkenyl groups, which are subsequently converted to dialdehydes. A cyclization reaction produces the conformationally restricted heptamethine cyanine compound.

Embodiments of compounds according to Formula I may be used for imaging applications. Some embodiments of a method for using a compound according to Formula I, wherein the compound includes a target agent, include combining the compound with a sample comprising a target capable of binding with the targeting agent; and imaging the target by visualizing the compound. In some embodiments, visualizing the compound includes irradiating the sample with targeted application of a quantity of light having a wavelength in the visible or near-infrared range and a selected intensity, wherein the quantity of light is sufficient to produce fluorescence of the compound; and detecting any fluorescence emitted by the compound. In any or all of the above embodiments, combining the compound with the sample may be performed in vitro, ex vivo, or in vivo. In any or all of the above embodiments, the method may further include combining the compound with a reducing agent prior to imaging the target. In any or all of the above embodiments, the sample may be a tissue sample, a biological fluid, or a target area within a subject. In some embodiments, the sample is a target area within a subject, and the method further includes administering the compound, or a pharmaceutical composition comprising the compound to the subject, subsequently irradiating the compound by targeted application of the quantity of light to a targeted portion of the subject, and detecting any fluorescence from the compound in the targeted portion of the subject. In certain embodiments, the target area is a tumor site, the targeted portion of the subject includes the tumor site, and the method further includes excising at least a portion of the tumor from the subject after detecting the fluorescence in the targeted portion of the subject.

In an independent embodiment, a method for detective reactive oxygen species includes combining a compound according to Formula I with a reducing agent to provide a reduced compound; contacting a sample with the reduced compound, whereby the reduced compound is oxidized to regenerate the compound according to Formula I if reactive oxygen species (ROS) are present in the sample; irradiating the sample with a quantity of light having a wavelength in the visible or near-infrared range and a selected intensity, wherein the quantity of light is sufficient to produce fluorescence if the reduced compound has been oxidized by the ROS to regenerate the compound according to Formula I; and detecting any fluorescence emitted by the compound according to Formula I, wherein fluorescence indicates the presence of ROS in the sample.

The foregoing and other objects, features, and advantages of the invention will become more apparent from the following detailed description, which proceeds with reference to the accompanying figures.

DETAILED DESCRIPTION

Figure 1:
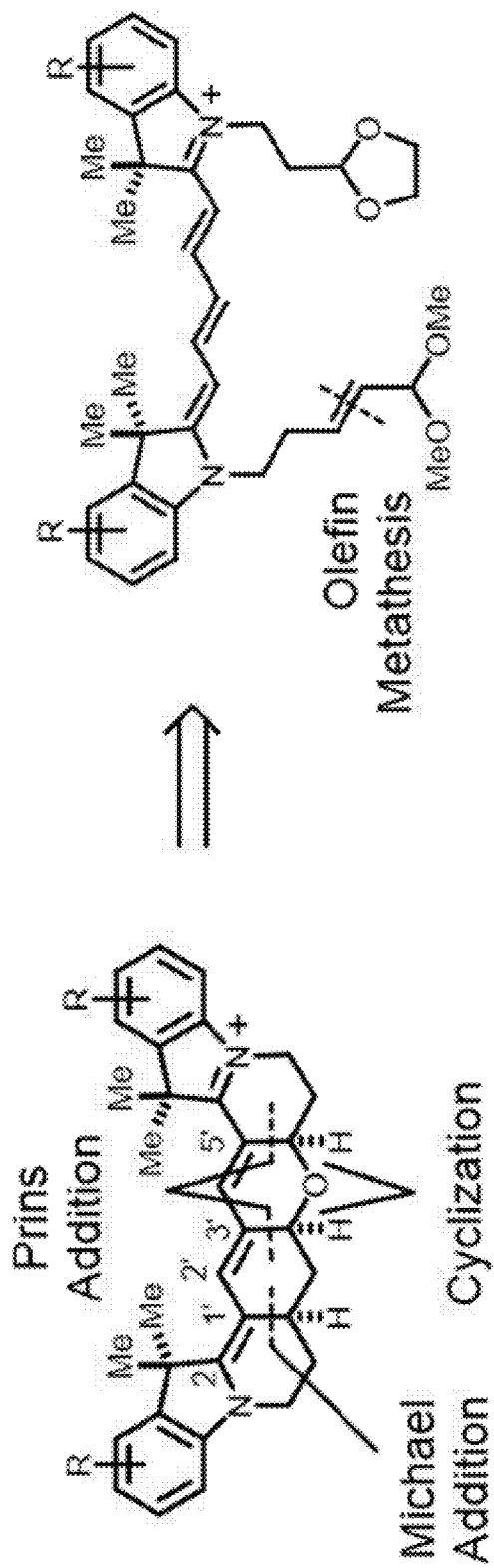
FIG. 1 is an exemplary retrosynthetic pathway for making a conformationally restricted pentamethine cyanine fluorophore.

This disclosure concerns embodiments of conformationally restricted cyanine fluorophores, and methods of making and using the conformationally restricted cyanine fluorophores. Advantageously, the conformationally restricted cyanine fluorophores have emission maxima that are in the far-red and near-infrared range, and/or have absorption and/or emission maxima that are red-shifted compared to corresponding cyanine fluorophores that are not conformationally restricted.

I. DEFINITIONS AND ABBREVIATIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2). Definitions of common terms in molecular biology may be found in Benjamin Lewin, *Genes VI*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

In order to facilitate review of the various embodiments of the disclosure, the following explanations of specific terms are provided:

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. The term "lower aliphatic" refers to an aliphatic group containing from one to ten carbon atoms. An aliphatic chain may be substituted or unsubstituted. Unless expressly referred to as an "unsubstituted aliphatic," an aliphatic group can either be unsubstituted or substituted. An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group). Exemplary substituents include, but are not limited to, alkyl, alkenyl, alkynyl, alkoxy, alkylamino, alkylthio, acyl, aldehyde, amide, amino, aminoalkyl, aryl, arylalkyl, carboxyl, cyano, cycloalkyl, dialkylamino, halo, haloaliphatic, heteroaliphatic, heteroaryl, heterocycloaliphatic, hydroxyl, oxo, sulfonamide, sulfhydryl, thioalkoxy, or other functionality.

Alkoxy: A group having the structure —OR, where R is a substituted or unsubstituted alkyl. Methoxy (—OCH$_3$) is an exemplary alkoxy group. In a substituted alkoxy, R is alkyl substituted with a non-interfering substituent.

Alkoxy carbonyl: A group having the structure —(O)C—O—R, where R is a substituted or unsubstituted alkyl.

Alkyl: A hydrocarbon group having a saturated carbon chain. The chain may be branched, unbranched, or cyclic (cycloalkyl). The term lower alkyl means the chain includes 1-10 carbon atoms. Unless otherwise specified, the term alkyl encompasses substituted and unsubstituted alkyl.

Alkyl sulfonate: A group having the structure —R—SO$_3^-$, where R is a substituted or unsubstituted alkyl.

Amino: A group having the structure —N(R)R' where R and R' are independently hydrogen, haloalkyl, aliphatic, heteroaliphatic, aryl (such as optionally substituted phenyl or benzyl), heteroaryl, alkylsulfano, or other functionality. A "primary amino" group is —NH$_2$. "Mono-substituted amino" means a radical —N(H)R substituted as above and includes, e.g., methylamino, (1-methylethyl)amino, phenylamino, and the like. "Di-substituted amino" means a radical —N(R)R' substituted as above and includes, e.g., dimethylamino, methylethylamino, di(1-methylethyl)amino, and the like. The term amino also encompasses charged tri-substituted amino groups, e.g., —N(R)(R')R''$^+$ where R, R', and R'' are independently hydrogen, haloalkyl, aliphatic, heteroaliphatic, aryl (such as optionally substituted phenyl or benzyl), heteroaryl, alkylsulfano, or other functionality.

Aminoalkyl: A chemical functional group —RNH$_2$ or —RNH$_3^+$ where R is an alkyl group. "Substituted aminoalkyl" means that the amino group is substituted, e.g., —RN(R')R'' or —RN(R')(R'')R'''$^+$ where R', R'', and R''' are independently hydrogen, haloalkyl, aliphatic, heteroaliphatic, aryl (such as optionally substituted phenyl or benzyl), heteroaryl, alkylsulfano, or other functionality.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. In avian and reptilian species, IgY antibodies are equivalent to mammalian IgG.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

The structure of IgY antibodies is similar to the structure of mammalian IgG, with two heavy ("nu" chains; approximately 67-70 kDa) and two light chains (22-30 kDa). The molecular weight of an IgY molecule is about 180 kDa, but it often runs as a smear on gels due to the presence of about 3% carbohydrate. Heavy chains (H) of IgY antibodies are composed of four constant domains and one variable domain, which contains the antigen-binding site.

As used herein, the term "antibodies" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999). As used herein, the term "antibodies" includes antibodies comprising one or more unnatural (i.e., non-naturally occurring) amino acids (e.g., p-acetyl-phenylalanine) to facilitate site-specific conjugation.

Antibodies for use in the methods of this disclosure can be monoclonal or polyclonal, and for example specifically bind a target such as the target antigen. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. As used herein, a "target antigen" is an antigen (including an epitope of the antigen) that is recognized and bound by a targeting agent. "Specific binding" does not require exclusive binding. In some embodiments, the antigen is obtained from a cell or tissue extract. In some embodiments, the target antigen is an antigen on a tumor cell. An antigen need not be a full-length protein. Antigens contemplated for use include any immunogenic fragments of a protein, such as any antigens having at least one epitope that can be specifically bound by an antibody.

Aryl: A monovalent aromatic carbocyclic group of, unless specified otherwise, from 6 to 15 carbon atoms having a single ring (e.g., phenyl) or multiple condensed rings in which at least one ring is aromatic (e.g., quinoline, indole, benzodioxole, and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic. Unless otherwise specified, the term aryl encompasses substituted and unsubstituted aryl.

Biological sample: As used herein, a "biological sample" refers to a sample obtained from a subject (such as a human or veterinary subject) or other type of organism, such as a plant, bacteria or insect. Biological samples from a subject include, but are not limited to, cells, tissue, serum, blood, plasma, urine, saliva, cerebral spinal fluid (CSF) or other bodily fluid. In particular examples of the method disclosed herein, the biological sample is a tissue sample.

Conformationally restricted: The term "conformationally restricted" as used herein refers to a cyanine compound that has been modified so that the molecule loses flexibility in the region of the central conjugated polymethine bridge. The term "rigidized" is a synonym for "conformationally restricted."

Conjugatable moiety: A portion of a molecule that allows the molecule to be conjugated (i.e., coupled or bound) to another molecule, e.g., to a drug or targeting agent such as an antibody.

dSTORM: Direct stochastic optical reconstruction microscopy.

Drug: As used herein, the term "drug" refers to a substance which has a physiological effect when administered to a subject, and is intended for use in the treatment, mitigation, cure, prevention, or diagnosis of disease or used to otherwise enhance physical or mental well-being. The term "small molecule drug" refers to a drug having a molecular weight <1,000 Daltons.

An anti-cancer drug is a drug that is used to treat malignancies. Exemplary anti-cancer drugs include, but are not limited to, abiraterone, actinomycin D, altretamine, amifostine, anastrozole, asparaginase, bexarotene, bicalutamide, bleomycin, buserelin, busulfan, carboplatin, carmustine, chlorambucil cisplatin, cladribine, clodronate, combretastatin A4, cyclophosphamide, cyproterone, cytarabine, dacarbazine, daunorubicin, degarelix, diethylstilbestrol, docetaxel, doxorubicin, duocarmycin DM, epirubicin, ethinyl estradiol, etoposide, exemestane, 5-fluorouracil, fludarabine, flutamide, folinic acid, fulvestrant, gemcitabine, goserelin, ibandronic acid, idarubicin, ifosfamide, irinotecan, lanreotide, lenalidomide, letrozole, leuprorelin, medroxyprogesterone, megestrol, melphalan, mesna, methotrexate, octreotide, pamidronate, pemetrexed, mitocmycin, mitotane, mitoxantrone, oxaliplatin, paclitaxel, pentastatin, pipbroman, plicamycin, procarbazine, raltitrexed, stilbestrol, streptozocin, tamoxifen, temozolomide, teniposide, topotecan, triptorelin, vinblastine, vincristine, vinorelbine, and zolendronic acid.

Effective amount or therapeutically effective amount: An amount sufficient to provide a beneficial, or therapeutic, effect to a subject or a given percentage of subjects.

Epitope: An antigenic determinant. Epitopes are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

Far-red: Far red light is generally considered to be light is a wavelength within a range of 700-850 nm.

Heteroaliphatic: An aliphatic compound or group having at least one heteroatom, i.e., one or more carbon atoms has been replaced with an atom having at least one lone pair of electrons, typically nitrogen, oxygen, phosphorus, silicon, or sulfur. Heteroaliphatic compounds or groups may be substituted or unsubstituted, branched or unbranched, cyclic or acyclic, and include "heterocycle", "heterocyclyl", "heterocycloaliphatic", or "heterocyclic" groups.

Heteroalkyl: An alkyl group as defined above containing at least one heteroatom, such as N, O, S, or S(O). (where n is 1 or 2). Unless otherwise specified, the term heteroalkyl encompasses substituted and unsubstituted heteroalkyl.

Heteroaryl: An aromatic compound or group having at least one heteroatom, i.e., one or more carbon atoms in the ring has been replaced with an atom having at least one lone pair of electrons, typically nitrogen, oxygen, phosphorus, silicon, or sulfur. Unless otherwise specified, the term heteroaryl encompasses substituted and unsubstituted heteroaryl.

Ligand: A molecule that binds to a receptor, having a biological effect.

Linker: A molecule or group of atoms positioned between two moieties. As used herein, the term "linker" refers to a group of atoms positioned between the cyanine fluorophore and a targeting agent or reactive group, or to a group of atoms positioned between the cyanine fluorophore and a drug.

Near-infrared (near-IR, NIR): Wavelengths within the range of 650-2500 nm. Unless otherwise specified, the terms "near-infrared" and "NIR" as used herein refer to wavelengths within the range of 650-900 nm.

PALM: Photo-activated localization microscopy.

PBS: Phosphate-buffered saline.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., $21^{st}$ Edition (2005), describes compositions and formulations suitable for pharmaceutical delivery of one or more conformationally restricted cyanine fluorophores as disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutically acceptable salt: A biologically compatible salt of a disclosed conformationally restricted cyanine fluorophores, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19, which is incorporated herein by reference.)

Phosphoramidite: A group having the general formula $(RO)_2PNR_2$. As a substituent, a phosphoramidite has a general formula —RO—P(OR)NR$_2$ where each R independently is aliphatic, such as substituted or unsubstituted alkyl.

Protecting group: When synthesizing organic compounds, often a specific functional group cannot survive the required reagents or chemical environments. These groups must be protected. A protecting group, or protective group, is introduced into a molecule by chemical modification of a functional group in order to obtain chemoselectivity in a subsequent chemical reaction. Various exemplary protecting or protective groups are disclosed in Greene's Protective Groups in Organic Synthesis, by Peter G. M. Wuts and Theodora W. Greene (Oct. 30, 2006), which is incorporated herein by reference.

SMLM: Single-molecule localization microscopy.

Specific binding partner: A member of a pair of molecules that interact by means of specific, non-covalent interactions that depend on the three-dimensional structures of the molecules involved. Exemplary pairs of specific binding partners include antigen/antibody, hapten/antibody, receptor/ligand, nucleic acid strand/complementary nucleic acid strand, substrate/enzyme, inhibitor/enzyme, carbohydrate/lectin, biotin/avidin (such as biotin/streptavidin), and virus/cellular receptor.

STORM: Stochastic optical reconstruction microscopy.

Substituent: An atom or group of atoms that replaces another atom in a molecule as the result of a reaction. The term "substituent" typically refers to an atom or group of atoms that replaces a hydrogen atom, or two hydrogen atoms if the substituent is attached via a double bond, on a parent hydrocarbon chain or ring. The term "substituent" may also cover groups of atoms having multiple points of attachment to the molecule, e.g., the substituent replaces two or more hydrogen atoms on a parent hydrocarbon chain or ring. In such instances, the substituent, unless otherwise specified, may be attached in any spatial orientation to the parent hydrocarbon chain or ring. Exemplary substituents include, for instance, alkyl, alkenyl, alkynyl, alkoxy, alkylamino, alkylthio, acyl, aldehyde, amido, amino, aminoalkyl, aryl, arylalkyl, arylamino, carbonate, carboxyl, cyano, cycloalkyl, dialkylamino, halo, haloaliphatic (e.g., haloalkyl), haloalkoxy, heteroaliphatic, heteroaryl, heterocycloaliphatic, hydroxyl, isocyano, isothiocyano, oxo, sulfonamide, sulfhydryl, thio, and thioalkoxy groups.

Substituted: A fundamental compound, such as an aryl or aliphatic compound, or a radical thereof, having coupled thereto one or more substituents, each substituent typically replacing a hydrogen atom on the fundamental compound. Solely by way of example and without limitation, a substituted aryl compound may have an aliphatic group coupled to the closed ring of the aryl base, such as with toluene. Again solely by way of example and without limitation, a long-chain hydrocarbon may have a hydroxyl group bonded thereto.

Sulfonate-containing group: A group including $SO_3^-$. The term sulfonate-containing group includes —$SO_3^-$ and —$RSO_3^-$ groups, where R is substituted or unsubstituted alkyl, substituted or unsubstituted heteroalkyl, substituted or unsubstituted aryl, or substituted or unsubstituted heteroaryl.

Target: An intended molecule to which a disclosed conformationally restricted cyanine fluorophore comprising a targeting agent is capable of specifically binding. Examples of targets include proteins and nucleic acid sequences present in tissue samples. A target area is an area in which a target molecule is located or potentially located.

Targeting agent: An agent that promotes preferential or targeted delivery to a target site, for example, a targeted location in a subject's body, such as a specific organ, organelle, physiologic system, tissue, or site of pathology such as a tumor, area of infection, or area of tissue injury. Targeting agents function by a variety of mechanisms, such as selective concentration in a target site or by binding to a specific binding partner. Suitable targeting agents include, but are not limited to, proteins, polypeptides, peptides, glycoproteins and other glycoslyated molecules, oligonucleotides, phospholipids, lipoproteins, alkaloids, and steroids. Exemplary targeting agents include antibodies, antibody fragments, affibodies, aptamers, albumin, cytokines, lymphokines, growth factors, hormones, enzymes, immune modulators, receptor proteins, antisense oligonucleotides, avidin, nano particles, and the like. Particularly useful of targeting agents are antibodies, nucleic acid sequences, and receptor ligands, although any pair of specific binding partners can be readily employed for this purpose.

TCEP: Tris(2-carboxyethyl)phosphine, a reducing agent.

TRABI: Temporal, radial-aperture-based intensity estimation.

Treat/treatment: As used herein, the terms "treat" and "treatment" mean to inhibit or reduce at least one sign or symptom associated with a condition, i.e., a disorder or disease. With respect to a tumor, treating may mean inhibiting tumor growth and/or reducing a tumor volume. Treatment may, for example, produce a reduction in severity of some or all clinical symptoms of the tumor, a slower progression of the tumor (for example by prolonging the life of a subject having the tumor), a reduction in the number of tumor reoccurrence, an improvement in the overall health or well-being of the subject, or by other parameters well known in the art that are specific to the particular disorder or disease.

Trityl: A substituted or unsubstituted triphenyl methyl group, e.g., $Ph_3C\text{—}OR\text{—}$ or $Ph_3CR\text{—}$ where R is aliphatic. Each phenyl group and R independently may be substituted or unsubstituted.

TSTU: N,N,N',N'-tetramethyl-O—(N-succinimidyl)uronium tetrafluoroborate, a coupling agent.

II. CONFORMATIONALLY RESTRICTED CYANINE FLUOROPHORES

Embodiments of the disclosed conformationally restricted cyanine fluorophores have a chemical structure according to Formula I, or a stereoisomer or pharmaceutically acceptable salt thereof:

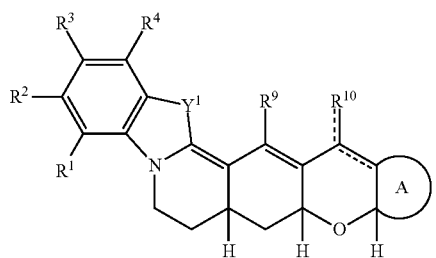

(I)

wherein A is

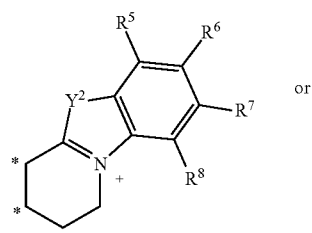

or

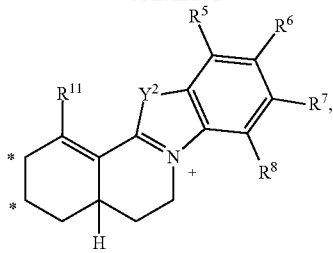

and wherein each "*" designates an attachment point of A. The bonds represented by "----" are single or double bonds as needed to satisfy valence requirements. $R^1$-$R^9$ and $R^{11}$ independently are H, deuterium, alkyl, heteroalkyl, —$N(R^a)_2$, sulfonate, alkyl sulfonate, amino, aminoalkyl, trityl, —$C(O)OR^a$, or a group comprising a conjugatable moiety, a targeting agent, or a drug, where each $R^a$ independently is H, deuterium, alkyl or heteroalkyl. $R^{10}$ is H, deuterium, O, alkyl, aryl, amino, sulfonate, —$C(O)OR^b$, —$OR^b$, —$N(R^b)_2$, heteroalkyl, heteroaryl, trityl, or a group comprising a conjugatable moiety, a targeting agent, or a drug, where each $R^b$ independently is H, deuterium, alkyl, heteroalkyl, aryl or heteroaryl. $Y^1$ and $Y^2$ independently are $C(R^c)_2$, $N(R^d)$, S, O, or Se, wherein each $R^c$ independently is H, deuterium, alkyl, —$(OCH_2CH_2)_xOH$ where x is an integer ≥2, trityl, or a group comprising a conjugatable moiety, a targeting agent, or a drug, and each $R^d$ independently is H, deuterium, alkyl, or heteroalkyl. In some examples, the trityl group has a formula —$(CH_2)_3OC(Ph_2)$(p-methoxyphenyl).

In any of the disclosed embodiments, an alkyl group or alkyl moiety of an alkyl sulfonate or aminoalkyl group may be lower alkyl ($C_1$-$C_{10}$ alkyl), $C_1$-$C_5$ alkyl, $C_1$-$C_3$ alkyl, methyl, ethyl, $C_3$ alkyl, $C_4$ alkyl, $C_5$ alkyl, $C_6$ alkyl, $C_7$ alkyl, $C_8$ alkyl, $C_9$ alkyl, $C_{10}$ alkyl. A heteroalkyl group may have a chain length, including carbon atoms and heteroatoms, of from 1-10, 1-5, or 1-3, such as a chain length of 2, 3, 4, 5, 6, 7, 8, 9, or 10.

In some embodiments, the conformationally restricted cyanine fluorophores have a chemical structure according to any one of Formulas IA-ID or a pharmaceutically acceptable salt thereof, wherein $R^1$-$R^{11}$, $Y^1$, and $Y^2$ are as previously described:

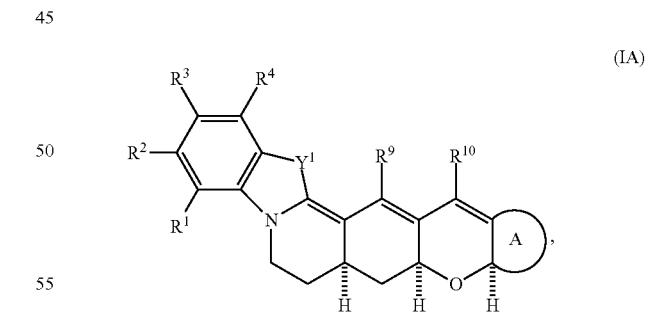

(IA)

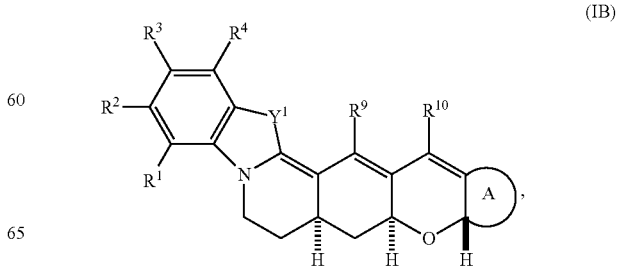

(IB)

-continued

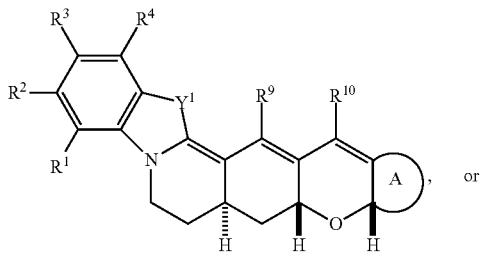

(IC)

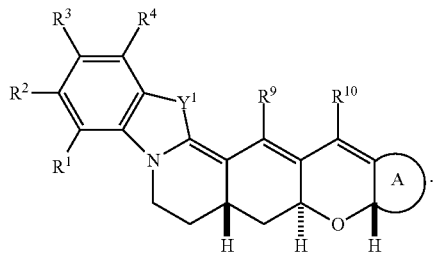

(ID)

In certain embodiments, the conformationally restricted cyanine fluorophores have a chemical structure according to Formula II or Formula III, or a stereoisomer or pharmaceutically acceptable salt thereof, wherein $R^1$-$R^{11}$ and $R^c$ are as previously described:

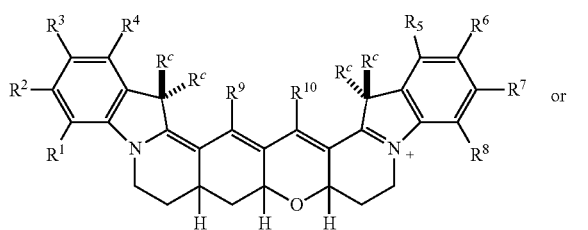

(II)

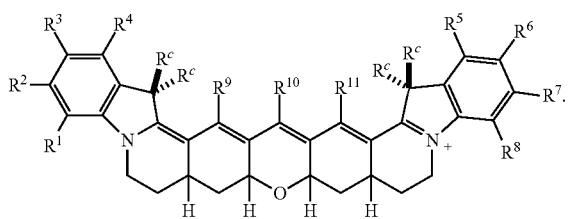

(III)

In any or all of the above embodiments, $R^1$-$R^9$ and $R^{11}$ independently are H, deuterium, alkyl, heteroalkyl, —N($R^a$)$_2$, sulfonate, alkyl sulfonate, amino, aminoalkyl, —C(O)O$R^a$, or a group comprising a conjugatable moiety, a targeting agent, or a drug, where $R^a$ is H, deuterium, alkyl or heteroalkyl. In some embodiments, at least one of $R^3$ and $R^6$ is sulfonate, —C(O)O$R^a$, trityl, or a group comprising a conjugatable moiety, a targeting agent, or a drug. In any or all of the foregoing embodiments, $R^1$, $R^2$, $R^4$, $R^5$, $R^7$, and $R^8$ may be H. In any or all of the foregoing embodiments, $R^9$ may be H. In any or all of the foregoing embodiments, $R^1$ and $R^8$, $R^2$ and $R^7$, $R^3$ and $R^6$, $R^4$ and $R^5$, and/or $R^9$ and $R^{11}$ may be the same. In certain embodiments, $R^1$, $R^2$, $R^4$, $R^5$, and $R^7$-$R^{11}$ are H, and $R^3$ and $R^6$ independently are —SO$_3$ or —CO$_2R^a$. In some examples, $R^3$ and $R^6$ are sulfonate.

In any or all of the above embodiments, $R^{10}$ is H, deuterium, O, alkyl, aryl, amino, sulfonate, triflate, (—OS(O)$_2$CF$_3$), —C(O)O$R^b$, —O$R^b$, heteroalkyl, heteroaryl, trityl, or a group comprising a conjugatable moiety, a targeting agent, or a drug, where $R^b$ is H, deuterium, alkyl, heteroalkyl, aryl, or heteroaryl. In some embodiments, $R^{10}$ is H, deuterium, O, alkyl, aryl, amino, sulfonate, triflate, (—OS(O)$_2$CF$_3$), —C(O)O$R^b$, —O$R^b$, heteroalkyl, heteroaryl, or a group comprising a conjugatable moiety, a targeting agent, or a drug, where $R^b$ is H, deuterium, alkyl, heteroalkyl, aryl, or heteroaryl. In certain embodiments, $R^{10}$ is H, O, aryl, —O$R^b$, —N($R^b$)$_2$, or triflate. In any or all of the foregoing embodiments, when the compound has a structure according to Formula II, $R^{10}$ may be H. In any or all of the foregoing embodiments, when the compound has a structure according to Formula III, $R^{11}$ may be H.

In any or all of the above embodiments, $Y^1$ and $Y^2$ independently are C($R^c$)$_2$, N($R^d$), S, O, or Se, wherein each $R^c$ independently is H, deuterium, alkyl, —(OCH$_2$CH$_2$)$_x$OH where x is an integer ≥2, trityl, or a group comprising a conjugatable moiety, a targeting agent, or a drug, and each $R^d$ independently is H, deuterium, alkyl, heteroalkyl, or trityl. In some embodiments, $Y^1$ and $Y^2$ are C($R^c$)$_2$ and each $R^c$ independently is C$_1$-C$_3$ alkyl, —(CH$_2$)$_n$C(O)$R^e$, or H, where n is an integer ≥1 and $R^e$ is a conjugatable moiety or a targeting agent. In any or all of the foregoing embodiments, at least one $R^c$ may be other than H. In any or all of the foregoing embodiments, each $R^c$ may be the same or each $R^d$ may be the same. In one embodiment, Y is C($R^c$)$_2$ where one $R^c$ is a group comprising a conjugatable moiety, a targeting agent, or a drug and the other $R^c$ is H, deuterium, or alkyl, and $Y^2$ is C($R^c$)$_2$ where each $R^c$ independently is H or alkyl. In an independent embodiment, $Y^1$ is C($R^c$)$_2$ where one $R^c$ is a group comprising a conjugatable moiety, a targeting agent, or a drug and the other $R^c$ is H or alkyl, and $Y^2$ is C($R^c$)$_2$ where one $R^c$ is trityl and the other $R^c$ is H or alkyl. In another independent embodiment, $Y^2$ is C($R^c$)$_2$ where one $R^c$ is a group comprising a conjugatable moiety, a targeting agent, or a drug and the other $R^c$ is H, deuterium, or alkyl, and $Y^1$ is C($R^c$)$_2$ where each $R^c$ independently is H or alkyl. In still another independent embodiment, $Y^2$ is C($R^c$)$_2$ where one $R^c$ is a group comprising a conjugatable moiety, a targeting agent, or a drug and the other $R^c$ is H or alkyl, and $Y^1$ is C($R^c$)$_2$ where one $R^c$ is trityl and the other $R^c$ is H or alkyl. In any or all of the foregoing embodiments, where $R^c$ is alkyl, the alkyl may be methyl.

In an independent embodiment, the compound has a chemical structure according to Formula II, $R^1$, $R^2$, $R^4$, $R^5$, $R^7$, $R^8$, and $R^c$ are as described above, $R^9$ and $R^{10}$ are H, and at least one of $R^3$ and $R^6$ is a group comprising a conjugatable moiety, a targeting agent, or a drug. In another independent embodiment, the compound has a chemical structure according to Formula II, $R^1$, $R^2$, $R^4$, $R^5$, $R^7$, and $R^8$ are as described above, $R^9$ and $R^{10}$ are H, $R^3$ and $R^6$ are sulfonate, and at least one $R^c$ is a group comprising a conjugatable moiety, a targeting agent, or a drug. In another independent embodiment, the compound has a chemical structure according to Formula III, $R^1$-$R^9$ and $R^{11}$ are H, and $R^{10}$ is H, O, triflate, aryl, —O$R^b$, or —N($R^b$)$_2$. In yet another independent embodiment, the compound has a chemical structure according to Formula III, $R^1$-$R^9$ and $R^{11}$ are H, and $R^{10}$ is a group comprising a conjugatable moiety, a targeting agent, or a drug. In another independent embodiment, the compound has a chemical structure according to Formula III, $R^1$, $R^2$, $R^4$, $R^5$, $R^7$, and $R^8$ are as described above, $R^3$ and $R^6$ are sulfonate, $R^9$ and $R^{11}$ are H, $R^{10}$ is H, O, triflate, aryl, —O$R^b$, or —N($R^b$)$_2$, and at least one $R^c$ is a group comprising a conjugatable moiety, a targeting agent, or a drug. Without wishing to be bound by a particular theory of operation, in some embodiments, inclusion of sulfonate groups, e.g., at $R^3$ and $R^6$, may decrease aggregation of the compounds in aqueous media, exhibit improved antibody labeling properties, and/or exhibit improved fluorescence emission compared to compounds without sulfonate groups.

In any or all of the above embodiments, a compound according to Formula I, IA-ID, II, or III may include at least one group comprising a conjugatable moiety, a targeting agent, or a drug. Exemplary groups comprising conjugatable moieties or targeting agents include, but are not limited to, —$(CH_2)_nC(O)R^e$, —$(CH_2)_nN(H)R^e$, —$(CH_2)_nN(H)C(O)R^e$, —$(CH_2)_nC(O)N(H)R^e$, —$(CH_2)_nC(O)SR^e$, —$C(O)R^e$, —$C(O)N(H)R^e$, —$C(O)N(H)(CH_2CH_2O)_m(CH_2)_nC(O)R^e$, —$N(H)C(O)R^e$, —$N(H)R^e$, or —$SR^e$ where m is an integer $\geq 1$, n is an integer $\geq 1$, and $R^e$ is a conjugatable moiety or targeting agent.

Suitable conjugatable moieties include, but are not limited to,

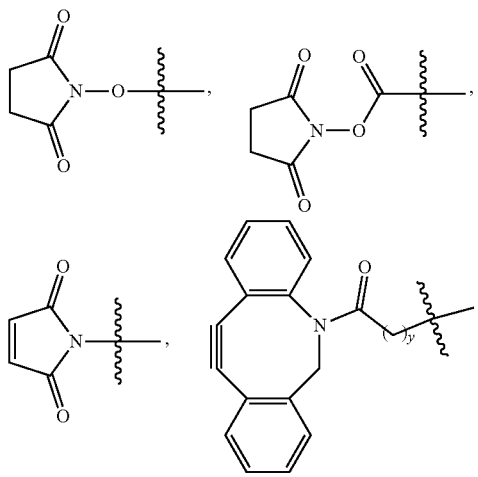

where y is an integer $\geq 1$, and phosphoramidites. In some examples, the phosphoramidite has a formula —$(CH_2)_3OP(O(CH_2)CN)(N(i-Pr)_2)$ where i-Pr is isopropyl. In certain embodiments, when the compound includes a phosphoramidite group on one half of the molecule, the compound may also include a trityl group on the other half of the molecule. For example, if $Y^1$ is substituted with a phosphoramidite group, then $Y^2$ may be substituted with a trityl group.

Exemplary targeting agents include, but are not limited to, antibodies, ligands, peptides, nucleic acid strands, and the like. In some examples, the targeting agent is phalloidin, a bicyclic heptapeptide that binds to F-actin. In certain examples, the targeting agent is an antibody. Exemplary antibodies include antibodies capable of recognizing and binding to a target molecule, such as a biomarker associated with a disease, infection, or environmental exposure. Biomarkers include, but are not limited to, proteins, peptides, lipids, metabolites, and nucleic acids. In some embodiments, the antibody is capable of recognizing and binding to a tumor biomarker, such as a protein only found in or on tumor cells or to a cell-surface receptor associated with one or more cancers. For example, panitumumab is a human monoclonal antibody that recognizes and binds to human epidermal growth factor receptor 1 (HER1); HER1 is overexpressed in numerous tumor types and is also associated with some inflammatory diseases. Trastuzumab and pertuzumab are monoclonal antibodies that bind to the HER2/neu receptor, which is over-expressed in some breast cancers. Brentuximab is a monoclonal antibody that targets a cell-membrane protein CD30, which is expressed in classical Hodgkin lymphoma and systemic anaplastic large cell lymphoma.

Exemplary groups comprising a drug include, but are not limited to, groups having a formula -$L_1$-C(O)—$X^1$-drug, where $L_1$ is a linker moiety or is absent and $X^1$ is O, N(H), or N(CH$_3$). In one embodiment, $L_1$ is absent. In another embodiment, $L_1$ is O. In an independent embodiment, $L_1$ is aryl or heteroaryl substituted with at least one substituent comprising a substituted or unsubstituted aliphatic or heteroaliphatic moiety, wherein the aryl or heteroaryl ring is the site of attachment to the remainder of the conformationally restricted cyanine fluorophore and the substituent is bonded to the —C(O)—$X^1$-drug moiety.

In some embodiments, the group comprising a drug is:

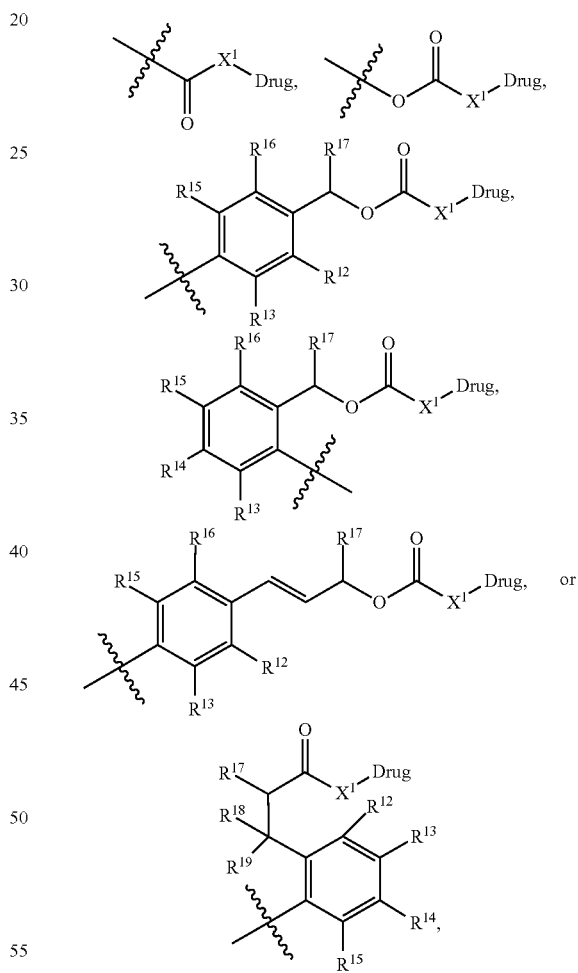

where $X^1$ is O, N(H), or N(CH$_3$), and $R^{12}$-$R^{19}$ independently are H, alkyl, —$NO_2$, —$NR'_2$, —$NR'_3{}^+$, alkoxy, or sulfonate, wherein each $R^f$ independently is H, halo, or alkyl. In certain embodiments, $R^{12}$-$R^{23}$ are H. In some examples, the group comprising a drug is —C(O)—$X^1$-Drug. The drug can be any drug capable of conjugation to the remainder of the group. In some embodiments, the drug is a small-molecule drug, e.g., a drug having a molecular weight <1,000 Daltons. In certain embodiments, the drug moiety is an anti-cancer drug.

Nonlimiting examples of compounds according to Formula I include:
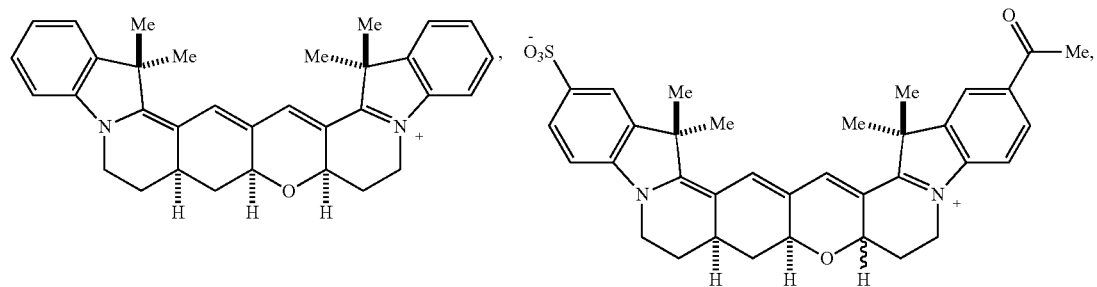
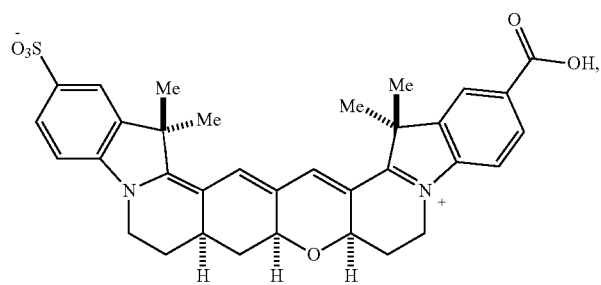
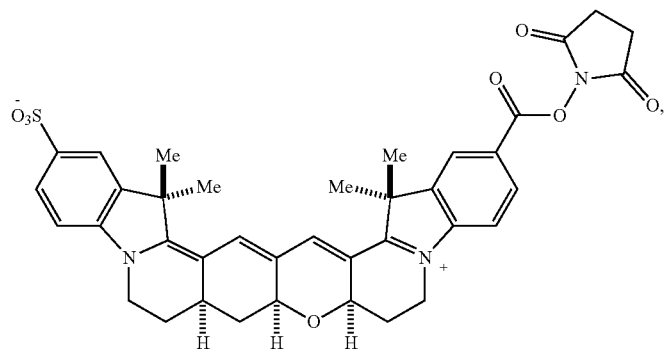
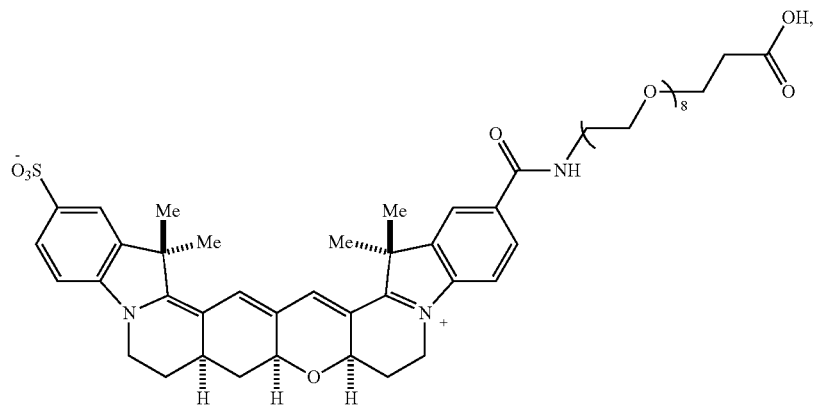

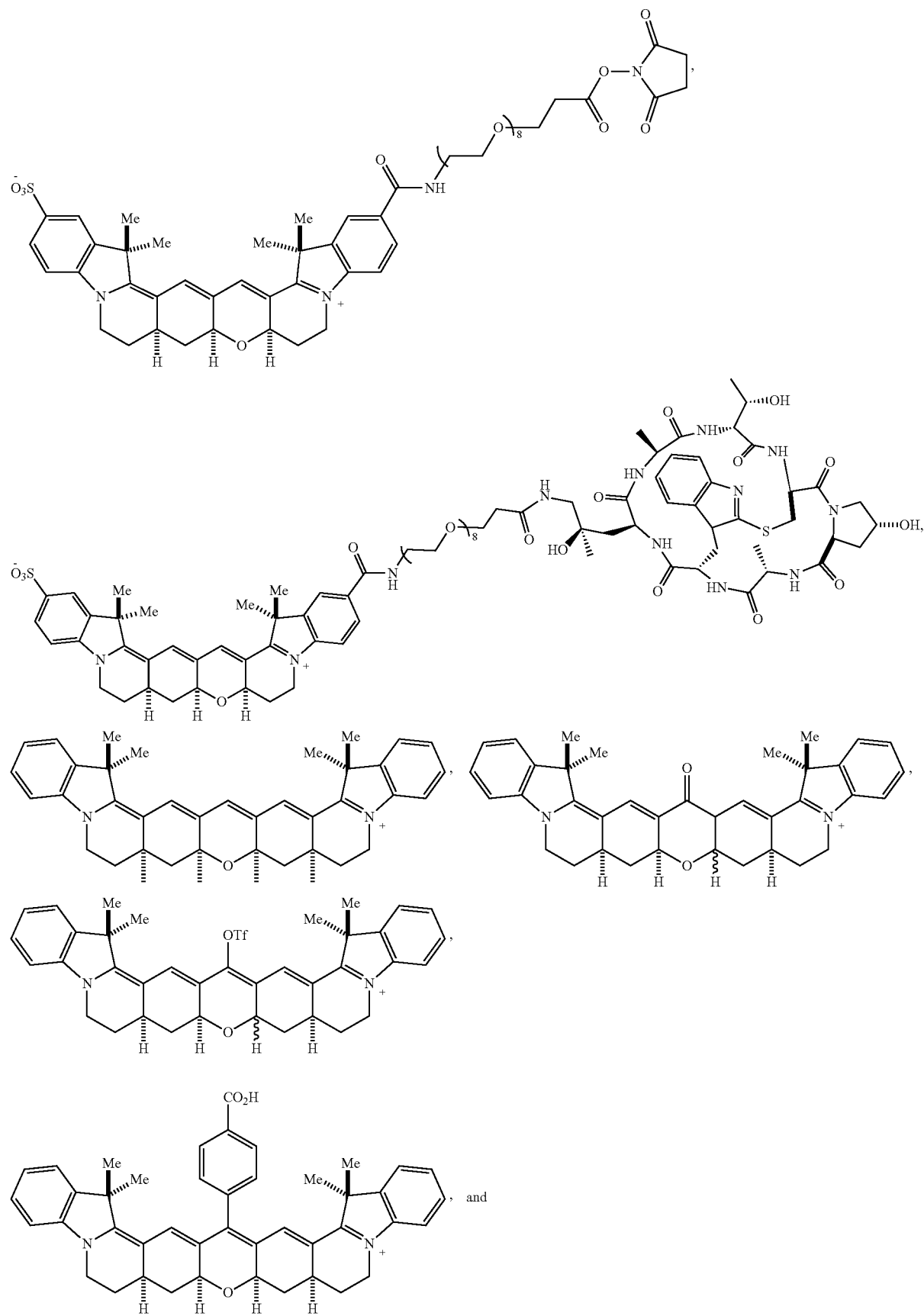

-continued

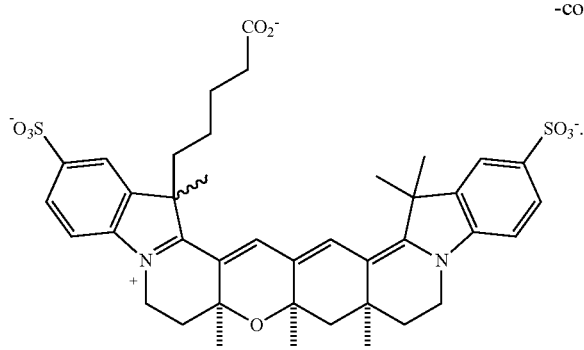

Embodiments of the disclosed conformationally restricted cyanine fluorophores exhibit improved quantum yields and/or extended fluorescence lifetimes relative to corresponding unrestrained pentamethine and heptamethine cyanines. In some embodiments, the quantum yield and/or fluorescence lifetime is at least 1.1×, at least 1.5×, at least 2×, at least 3×, at least 4×, or at least 5× greater than the quantum yield and/or fluorescence lifetime of the corresponding non-restricted cyanine fluorophore. The quantum yield and/or fluorescence lifetime may be 1.1-10×, such as 1.5-8×, 1.5-5×, or 2-5× greater than the quantum yield and/or fluorescence lifetime of the corresponding non-restricted cyanine fluorophore. Advantageously, the maximum wavelengths for absorption and emission may be red-shifted compared to the corresponding non-restricted cyanine fluorophore. In certain embodiments, $\lambda_{max}$ and/or $\lambda_{em}$ are red-shifted by at least 10 nm, at least 20 nm, or at least 30 nm, such as from 10-50 nm, 10-40 nm, 10-30 nm, or 10-20 nm relative to the $\lambda_{max}$ and/or $\lambda_{em}$ values of the corresponding non-restricted cyanine fluorophore. Additionally, some embodiments of the disclosed conformationally restricted cyanine fluorophores recover from hydride reduction with superior efficiency relative to existing far-red and/or near-IR cyanines. In certain embodiments, these properties enable PALM-like SMLM, providing excellent photon counts without recourse to high thiol, deoxygenated buffer.

III. PHARMACEUTICAL COMPOSITIONS

This disclosure also includes pharmaceutical compositions comprising at least one conformationally restricted cyanine fluorophore as disclosed herein. Some embodiments of the pharmaceutical compositions include a pharmaceutically acceptable carrier and at least one conformationally restricted cyanine fluorophore. Useful pharmaceutically acceptable carriers and excipients are known in the art.

The pharmaceutical compositions comprising one or more conformationally restricted cyanine fluorophores may be formulated in a variety of ways depending, for example, on the mode of administration and/or on the location to be imaged. Parenteral formulations may comprise injectable fluids that are pharmaceutically and physiologically acceptable fluid vehicles such as water, physiological saline, other balanced salt solutions, aqueous dextrose, glycerol or the like. Excipients may include, for example, nonionic solubilizers, such as Cremophor®, or proteins, such as human serum albumin or plasma preparations. If desired, the pharmaceutical composition to be administered may also contain non-toxic auxiliary substances, such as wetting or emulsifying agents, preservatives, and pH buffering agents and the like, for example, sodium acetate or sorbitan monolaurate.

The form of the pharmaceutical composition will be determined by the mode of administration chosen. Embodiments of the disclosed pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation. Generally, embodiments of the disclosed pharmaceutical compositions will be administered by injection, systemically, or orally.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. The composition may take such forms as suspension, solutions or emulsions in oily or aqueous vehicles, and may contain formulatory agents such as suspending, stabilizing and/or dispersing agents. For example, parenteral administration may be done by bolus injection or continuous infusion. Alternatively, the conformationally restricted cyanine fluorophore may be in powder form for reconstitution with a suitable vehicle, e.g. sterile water, before use.

Systemic formulations include those designed for administration by injection, e.g., subcutaneous, intravenous, intramuscular, intrathecal or intraperitoneal injection, as well as those designed for transdermal, transmucosal, oral or pulmonary administration.

Oral formulations may be liquid (e.g., syrups, solutions or suspensions), or solid (e.g., powder, tablets, or capsules). Oral formulations may be coupled with targeting ligands for crossing the endothelial barrier. Some conformationally restricted cyanine fluorophore formulations may be dried, e.g., by spray-drying with a disaccharide, to form conformationally restricted cyanine fluorophore powders. Solid compositions prepared by conventional means with pharmaceutically acceptable excipients such as binding agents (e.g., pregelatinised maize starch, polyvinylpyrrolidone or hydroxypropyl methylcellulose); fillers (e.g., lactose, mannitol, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings. Actual methods of preparing such dosage forms are known, or will be apparent, to those skilled in the art.

Liquid preparations for oral administration may take the form of, for example, elixirs, solutions, syrups or suspensions. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophor® or fractionated vegetable oils); and preservatives (e.g., methyl or propyl-p-hydroxybenzoates or sorbic acid). The preparations may also contain buffer salts, preservatives, flavoring, coloring and sweetening agents as appropriate. Preparations for oral administration may be suitably formulated to give controlled release of the fluorophore, as is well known.

For rectal and vaginal routes of administration, the conformationally restricted cyanine fluorophore(s) may be formulated as solutions (for retention enemas) suppositories or ointments containing conventional suppository bases such as cocoa butter or other glycerides.

For nasal administration or administration by inhalation or insufflation, the conformationally restricted cyanine fluorophore(s) can be conveniently delivered in the form of an aerosol spray or mist from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount.

Certain embodiments of the pharmaceutical compositions comprising conformationally restricted cyanine fluorophores as described herein may be formulated in unit dosage form suitable for individual administration of precise dosages. The pharmaceutical compositions may, if desired, be presented in a pack or dispenser device which may contain one or more unit dosage forms containing the conformationally restricted cyanine fluorophore. The pack may, for example, comprise metal or plastic foil, such as a blister pack. The pack or dispenser device may be accompanied by instructions for administration.

The amount of conformationally restricted cyanine fluorophore administered will depend at least in part on the subject being treated, the target (e.g., the size, location, and characteristics of a tumor), and the manner of administration, and may be determined as is known to those skilled in the art of pharmaceutical composition and/or contrast agent administration. Within these bounds, the formulation to be administered will contain a quantity of the conformationally restricted cyanine fluorophore disclosed herein in an amount effective to enable visualization of the conformationally restricted cyanine fluorophore by suitable means after administration to the subject. In certain embodiments, the conformationally restricted cyanine fluorophore comprises a drug bound to the molecule, and the formulation to be administered will contain a quantity of the drug bound to the conformationally restricted cyanine fluorophore effective to provide a therapeutically effective dose of the drug to the subject being treated.

In some embodiments, the pharmaceutical composition includes a second agent other than the conformationally restricted cyanine fluorophore. The second agent may be, for example, an anti-tumor agent or an angiogenesis inhibitor.

IV. SYNTHESIS

Conformationally restricted trimethine cyanine dyes have been synthesized previously by treating a trimethine cyanine dye in mild acid solution (e.g., acetic acid) under refluxing conditions or in a stronger mineral acid solution under milder conditions whereupon a "rigidized" carbocyanine dye precipitates from solution (see, e.g., WO99/31181). This synthetic strategy, however, cannot be extended to far-red and near-IR cyanines such as pentamethine and heptamethine cyanines. Heretofore, no synthetic strategy for making conformationally restricted cyanine fluorophores according to Formula I was known.

Disclosed herein are embodiments of methods for making conformationally restricted pentamethine and heptamethine cyanine fluorophores. Embodiments of a method for making conformationally restricted pentamethine cyanine fluorophores, i.e., compounds according to Formula I wherein A is

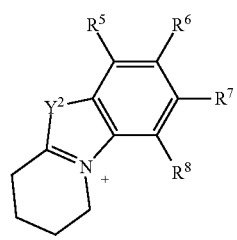

proceed via a cyclization cascade of a protected dialdehyde precursor, which is accessed through chemoselective olefin metathesis. FIG. 1 illustrates one embodiment of a retrosynthetic pathway for making a conformationally restricted pentamethine cyanine fluorophore. In the key reaction, a protected dialdehyde undergoes intramolecular Michael addition followed by a dihydropyran ring-forming cascade. As the cyanine polyene is incompatible with nucleophilic olefination methods, a critical challenge is the chemoselective introduction of the sensitive α,β-unsaturated aldehyde motif (or synthetic equivalent). A cross-metathesis reaction was ultimately found to provide a suitable method to install an unsaturated acetal.

Figure 2:
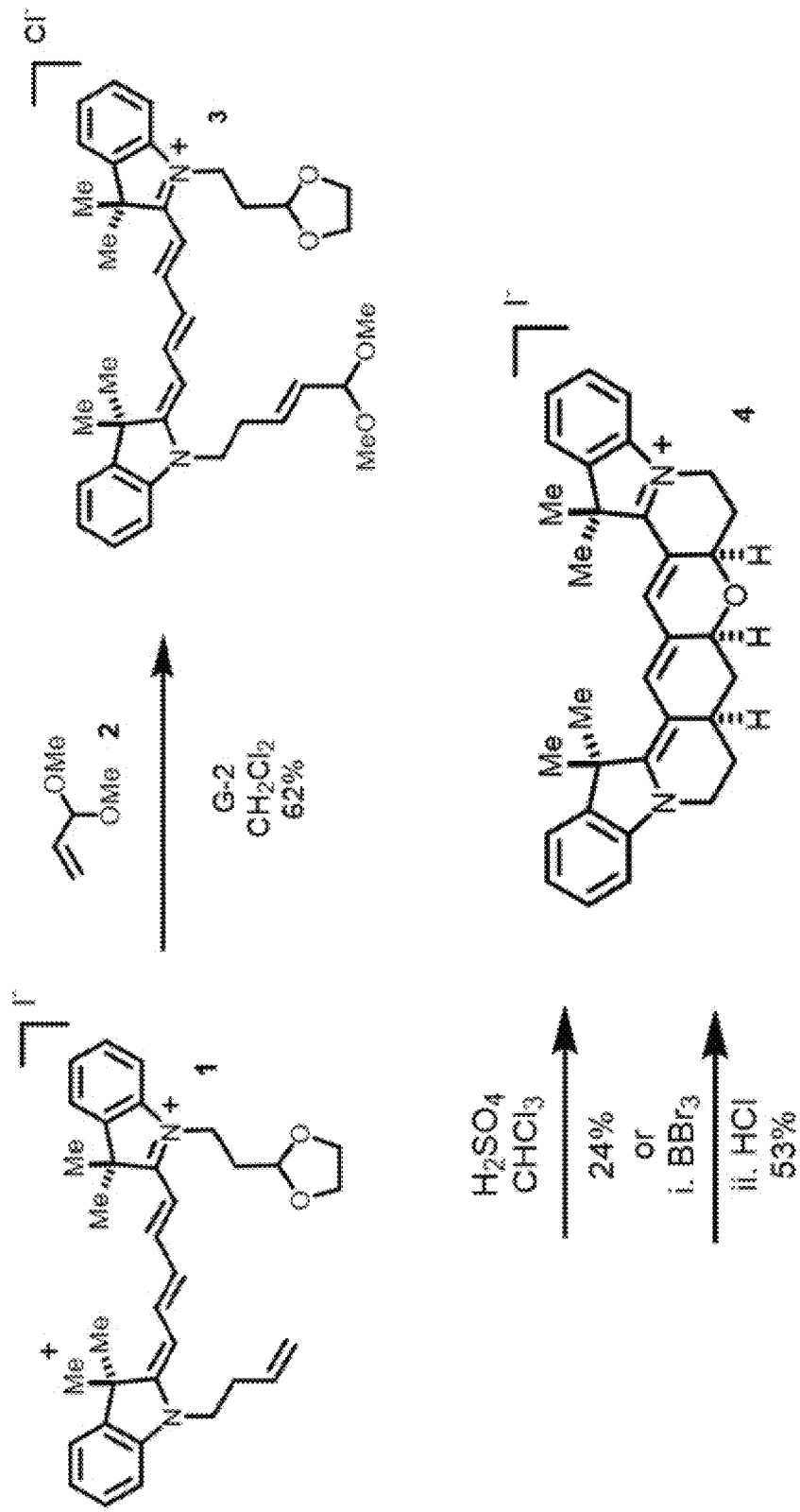
FIG. 2 is an exemplary synthetic scheme for preparing an unsubstituted, conformationally restricted pentamethine cyanine fluorophore.

FIG. 2 shows an exemplary synthetic scheme for preparing one embodiment of an unsubstituted, conformationally restricted pentamethine cyanine fluorophore. Precursor 1 is prepared from N-alkylated indolenines as described in more detail below. Cross-metathesis using Grubbs second generation catalyst and acrolein dimethyl acetal in dichloromethane provided compound 3 following purification. Compound 3 undergoes tetracyclization in a heated (e.g., 70° C.) acidified chloroform solution to provide compound 4 as a single diastereomer. Alternatively, reaction of compound 3 in a cold (e.g., −78° C.) solution of boron tribromide in dichloromethane provides compound 4 and another compound, which can be converted to compound 4 in a heated (e.g., 60° C.) solution of 1:3 methanol:0.3 M HCl.

Figure 3:
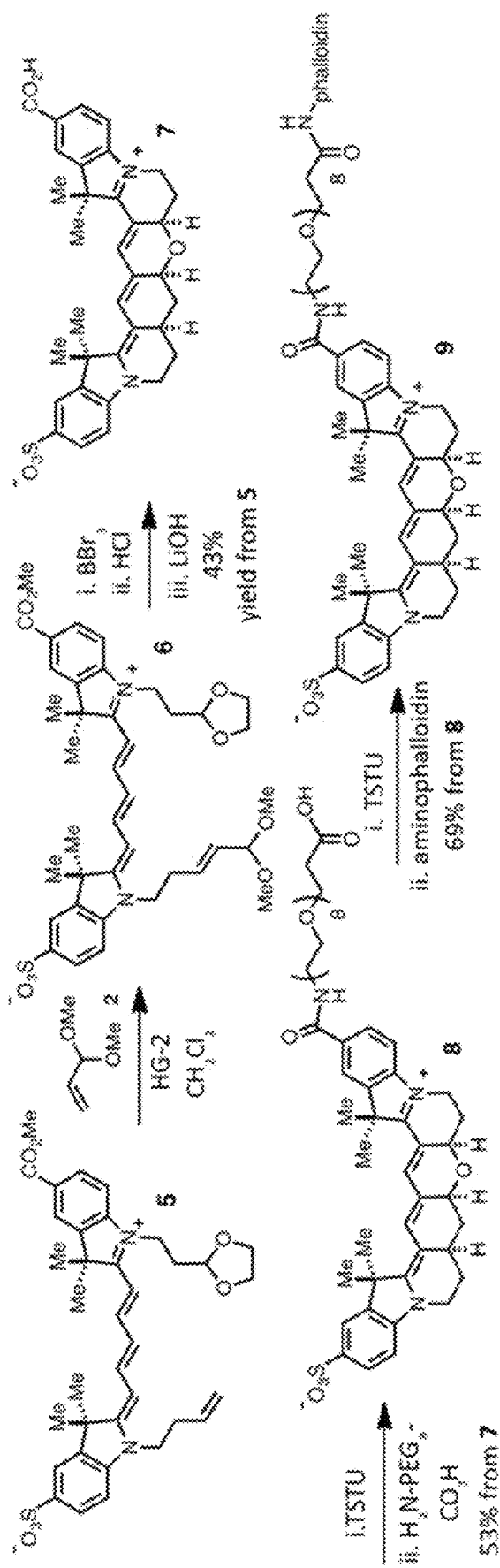
FIG. 3 is an exemplary synthetic scheme for preparing a conjugatable, conformationally restricted pentamethine cyanine fluorophore.

FIG. 3 shows an exemplary synthetic scheme for making a conjugatable variant of a conformationally restricted pentamethine cyanine fluorophore. Cross-metathesis using Hoyveda-Grubbs second generation catalyst proceeds efficiently between compound 5 and compound 2 at room temperature to provide compound 6, which can be used without extensive purification. Tetracyclization of compound 6 proceeds in a cold (e.g., −78° C.) solution of boron tribromide in dichloromethane to provide a mixture including compound 7. Equilibration in a heated (e.g., 60° C.) solution of 1:3 methanol:0.3 M HCl provides a methyl ester 6, which after saponification and purification provides compound 7. To prepare a compound suitable for bioconjugation, compound 7 may be converted to a carboxylic acid 8 through an amide coupling sequence. In the example of FIG. 3, phalloidin was conjugated to the molecule by N-hydroxysuccinimide-ester generation and amide bond formation to provide a phalloidin conjugate 9.

In some embodiments, the method includes combining a solution comprising a compound according to Formula IV with 3-buten-1-yl trifluoromethanesulfonate to produce a compound according to Formula V

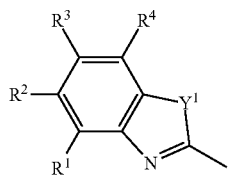

(IV)

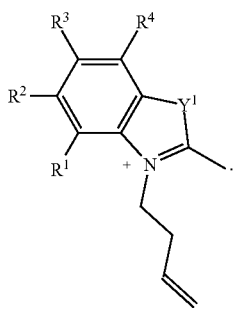

(V)

A solution comprising the compound according to Formula V and a compound according to Formula VI is combined with N-((1E,3Z)-3-(phenylamino)propo-1-en-1-yl)aniline or N-((1E,3E)-3-(phenylimino)prop-1-en-1-yl)aniline (e.g., malonaldehyde bis(phenylimine) monohydrochloride) to form a compound according to Formula VII

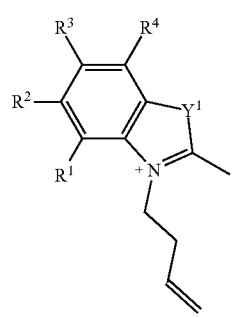

(V)

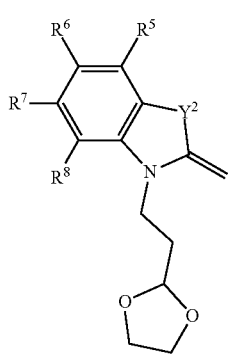

(VI)

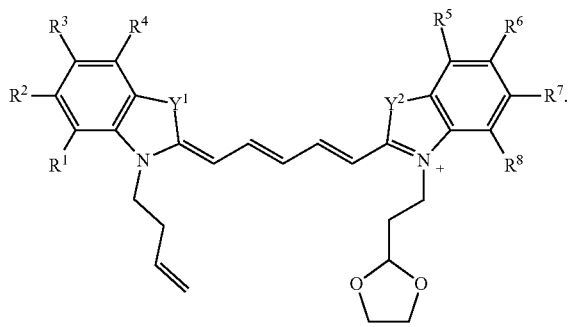

(VII)

A solution comprising the compound according to Formula VII is combined with 3,3-dimethoxy-1-propene in the presence of a ruthenium catalyst (e.g., Grubbs second generation catalyst—1,3-bis(2,4,6-trimethylphenyl)-2-imidazolidinylidene)-dichloro(phenylmethylene)(tricyclohexylphosphine)ruthenium, or Hoyveda-Grubbs second generation catalyst—1,3-bis-(2,4,6-trimethylphenyl)-2-imidazolidinylidene)-dichloro(o-isopropoxyphenylmethylene)ruthenium) to provide a compound according to Formula VIII

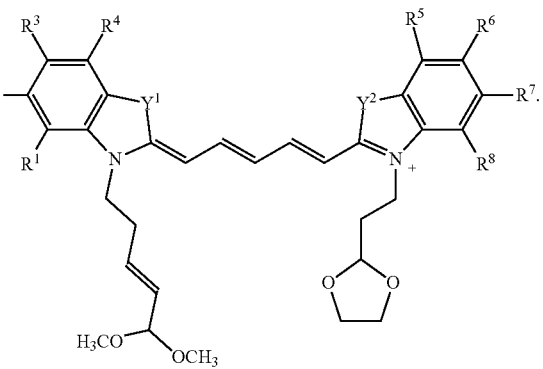

(VIII)

The compound according to Formula VIII is combined with (i) a mixture of CHCl$_3$ and H$_2$SO$_4$ or (ii) BBr$_3$ in CH$_2$Cl$_2$ to provide a compound according to Formula IX:

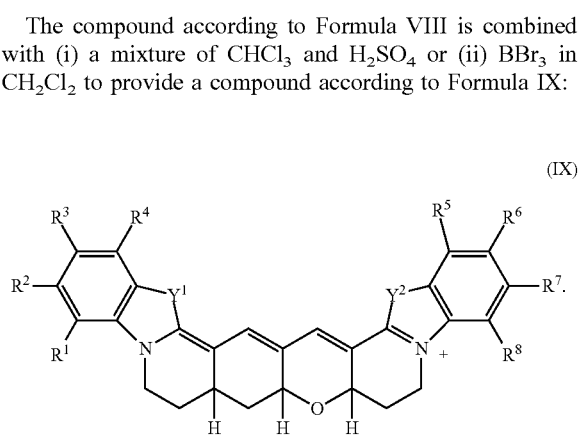

(IX)

Embodiments of a method for making conformationally restricted heptamethine cyanine fluorophores, i.e., compounds according to Formula I wherein A is

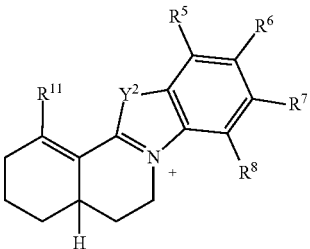

include combining a solution comprising a compound according to Formula IV with 3-buten-1-yl trifluoromethanesulfonate to produce a compound according to Formula V, and combining a solution comprising a compound according to Formula X with 3-buten-1-yl trifluoromethanesulfonate to produce a compound according to Formula XI:

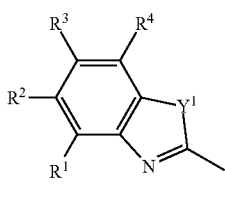
(IV)

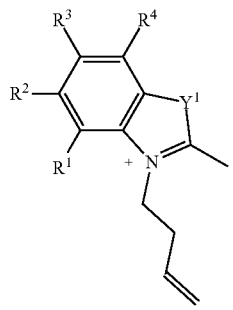
(V)

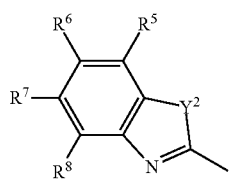
(X)

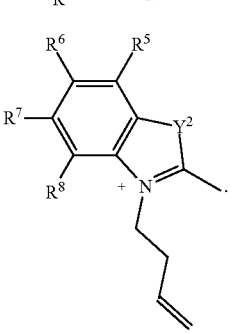
(XI)

In some embodiments, it may be desirable to produce a symmetrical conformationally restricted cyanine fluorophore. In such embodiments, the compounds according to Formula IV and X are the same, thereby producing compounds according to Formulas V and XI that are the same. In these embodiments, a single step of combining a solution comprising a compound according to Formula IV/X with 3-buten-1-yl trifluoromethanesulfonate to produce a compound according to Formula V/XI may be performed.

A solution comprising the compound according to Formula V and the compound according to Formula XI (if different than the compound according to Formula V) is combined with (1E,4E)-1,5-bis(dimethylamino)-penta-1,4-dien-3-one to produce a compound according to Formula XII:

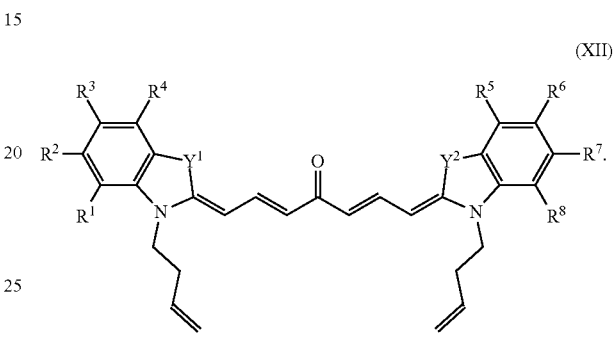
(XII)

A solution comprising the compound according to Formula XII is combined with 3,3-dimethoxy-1-propene in the presence of a ruthenium catalyst (e.g., Grubbs second generation catalyst—1,3-bis(2,4,6-trimethylphenyl)-2-imidazolidinylidene)-dichloro(phenylmethylene)(tricyclohexylphosphine)ruthenium, or Hoyveda-Grubbs second generation catalyst—1,3-bis-(2,4,6-trimethylphenyl)-2-imidazolidinylidene)-dichloro(o-isopropoxyphenylmethylene) ruthenium) to provide a compound according to Formula XIII:

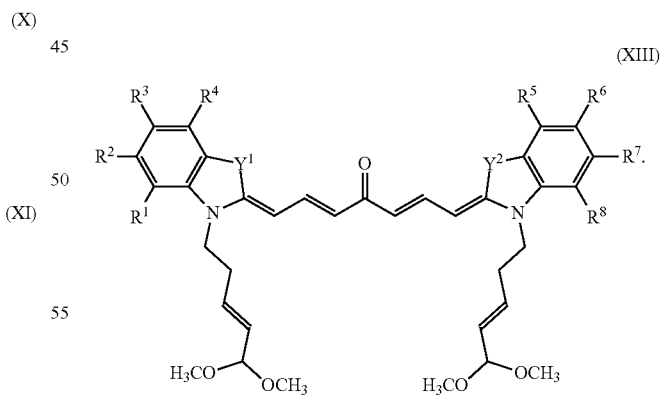
(XIII)

A solution comprising the compound according to Formula XIII is combined with an acidic tetrahydrofuran solution (e.g., 1 N HCl in tetrahydrofuran) to provide a compound according to Formula XIV:

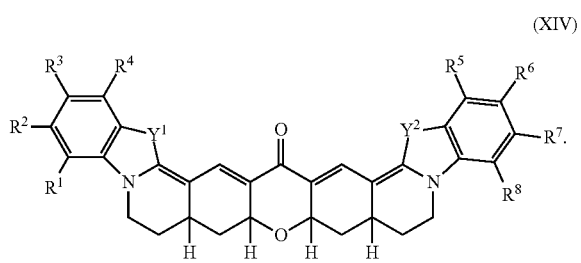

(XIV)

The ketone group of Formula XIV can be modified as desired to provide variations in the structure. Several variations can be made following an initial conversion of the ketone group to triflate. The triflate group is introduced by combining a solution comprising the compound according to Formula XIV with trifluoromethanesulfonic anhydride (Tf$_2$O) to provide a compound according to Formula XV:

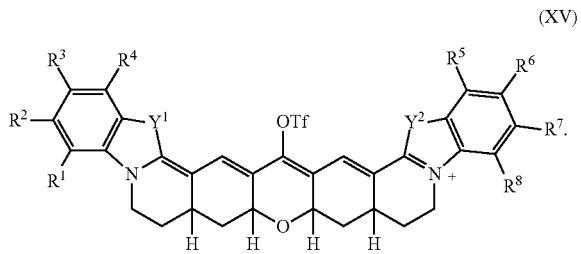

(XV)

In one embodiment, the triflate group is replaced with an aryl group by combining a solution comprising the compound according to Formula XV with R$^g$—C$_6$H$_4$—B(OH)$_2$ in the presence of a palladium catalyst to provide a compound according to Formula XVI:

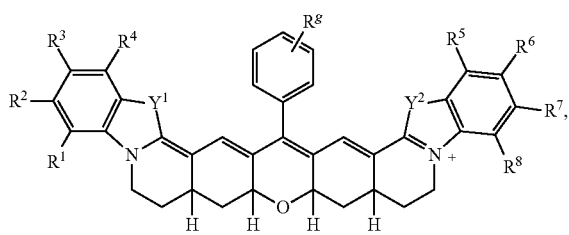

(XVI)

where R$^g$ is R$^a$, —COOR$^a$, or —OR$^a$, and R$^a$ is H, deuterium, alkyl or heteroalkyl.

In another embodiment, the triflate group is replaced with an amino group by combining a solution comprising the compound according to Formula XV with an amine having a formula NH(R$^{20}$)(R$^{21}$) to provide a compound according to formula XVII:

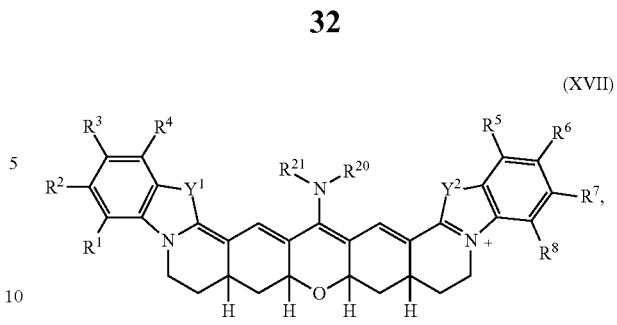

(XVII)

where R$^{20}$ and R$^{21}$ independently are H, deuterium, alkyl, heteroalkyl, aryl or heteroaryl. This process can be performed in the presence or absence of a palladium catalyst.

In some examples, R$^{20}$ is —(CR$^h_2$)$_n$—CH$_2$OH where each R$^h$ independently is H, deuterium, halo, alkyl, or aryl, and n is 1, 2, 3, or 4; and R$^{21}$ is H, deuterium, alkyl, heteroalkyl, aryl, or heteroaryl. Such compounds have a structure according to Formula XVIIa:

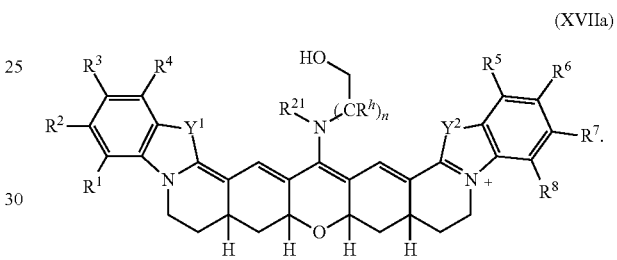

(XVIIa)

In certain embodiments, each R$^h$ is H and/or R$^{21}$ is H. In any or all of the foregoing embodiments, n may be 1 or 2.

In some embodiments, a compound according to Formula XVIIa can undergo an N- to O-rearrangement when reacted with an electrophile under basic conditions. Thus, in certain examples, a solution comprising a compound according to Formula XVIIa is combined with a compound comprising an electrophilic group R$^{22}$ under basic conditions to provide a compound according to Formula XVIII:

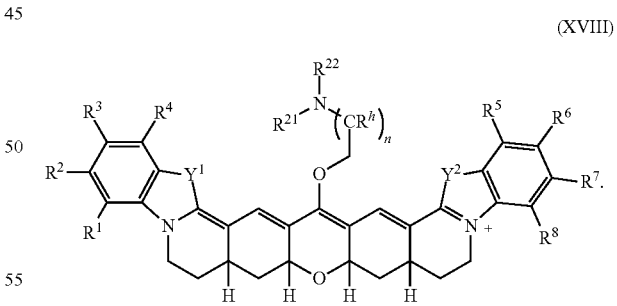

(XVIII)

Suitable electrophilic groups R$^{22}$ include, but are not limited to, a maleimidyl-containing group, a succinimidyl-containing group, optionally substituted alkoxy, optionally substituted alkyl carbonyl, optionally substituted alkoxy carbonyl, a biomolecule-containing group, or a combination thereof. Exemplary maleimidyl- and succinimidyl-containing groups may further include a carbonyl, alkyl carbonyl, alkoxy, or alkoxy carbonyl group attached to the ring nitrogen. In some embodiments, R$^{22}$ is formed by a combination of two groups that participate in the rearrangement, e.g., glutaric anhydride and N-hydroxysuccinimide may combine to form the succinimidyl-containing group —(O)C(CH$_2$)$_3$C(O)O—NC$_4$H$_4$O$_2$.

Exemplary solvents for the reaction include, but are not limited to, tetrahydrofuran (THF), N,N-dimethylformamide (DMF), dichloromethane (DCM), water, and combinations thereof.

Suitable bases include inorganic and organic bases. Exemplary bases include, but are not limited to, carbonates (e.g., K$_2$CO$_3$, Na$_2$CO$_3$), hydrogen carbonates (e.g., KHCO$_3$, NaHCO$_3$), hydroxides (e.g., KOH, NaOH), and organic amines (e.g., 4-dimethylaminopyridine (DMAP), N,N-diisopropylethylamine (DIPEA), 1-ethyl-3-(3-dimethylaminopropyl)carbodiimide (EDC, EDAC, or EDCI), and N-[(dimethylamino)-1H-1,2,3-triazolo-[4,5-b]pyridin-1-ylmethylene]-N-methylmethanaminium hexafluorophosphate N-oxide (HATU)).

Exemplary compounds comprising R$^{22}$ include, but are not limited to chloroformates, cyclic anhydrides, alkyl halides, carboxylic acids, and tetrafluoroborates. In some embodiments, the carboxylic acids are activated carboxylic acids, such as carboxylic acids preactivated with HATU and DIPEA before addition to the solution comprising the compound according to Formula XVIIa.

Effective conditions may include reacting at a reaction temperature ranging from room temperature (20-26° C.) to 100° C. for a time ranging from a few minutes to several hours. In certain examples, the reaction temperature ranges from room temperature to 90° C., and the time ranges from 10 minutes to 18 hours. In one example, the solution is irradiated with microwave irradiation at the reaction temperature. In various embodiments, the solution is stirred gently, stirred vigorously, or not stirred. The reaction may proceed in a sealed vessel under an inert atmosphere (e.g., argon, nitrogen). Completion of the reaction may be monitored by any suitable means including, but not limited to, a visual color change or LC/MS. The compound according to Formula XVIII is recovered, and optionally purified, by suitable means. In some embodiments, the compound is recovered and/or purified by extraction, precipitation, evaporation, ion exchange, chromatography (e.g., silica gel chromatography, HPLC), and combinations thereof.

Some embodiments of the compounds disclosed herein are suitable for further conjugation to a targeting agent, such as a biomolecule. For example, when R$^{22}$ terminates in a succinimidyl moiety, a maleimidyl moiety, —COOH, or —COO$^-$, a biomolecule may be conjugated to the conformationally restricted cyanine fluorophore by methods known to a person of ordinary skill in the art, e.g., via a bioconjugation reaction mediated by N,N'-disuccinimidyl carbonate. Suitable biomolecules include, but are not limited to, antibodies, peptides, amino acids, proteins, and haptens.

V. METHODS OF USE

Embodiments of the disclosed compounds according to Formula I may be useful for live-cell localization and tracking applications. Additionally, some embodiments of the disclosed compounds may be useful for sensing reactive oxygen species (ROS). In certain embodiments, inclusion of sulfonate or other polar functional groups may facilitate antibody labeling. Furthermore, some embodiments of the disclosed compounds may be cell-permeable, an advantage for live-cell studies. Investigative, diagnostic, and theranostic uses are within the scope of the disclosure.

Compounds according to Formula I may be utilized in in vitro, ex vivo, and in vivo localization and tracking applications. In some embodiments, a compound according to Formula I that comprises at least one targeting agent at any of R$^1$-R$^{11}$, Y$^1$, or Y$^2$ is combined with a sample comprising a target capable of binding with the targeting agent, and the target is imaged by visualizing the compound. The sample may be, for instance, a tissue sample, a biological fluid (e.g., blood, urine, saliva), or a target area within a subject such as a location of a known or suspected tumor. Advantageously, combining the compound with the sample is performed under conditions (temperature, pH, concentration, etc.) effective to provide binding of the targeting agent and target. After a period time effective for binding to occur, which may range from a few seconds to several days, the compound is visualized. Prior to visualization, excess, unbound compound may be removed from the sample, e.g., by washing the sample under conditions effective to remove unbound compound without disrupting compound molecules bound to the target or by waiting a sufficient period of time (such as a few hours or days) for unbound compound to be eliminated from the target area in vivo. In certain embodiments, the compound according to Formula I is reduced prior to visualization. Suitable reducing agents include, but are not limited to, hydrides such as sodium borohydride (NaBH$_4$). The reduction occurs in moiety A as shown below.

reduced A:

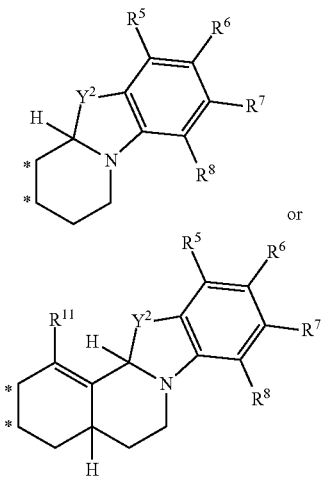

In some embodiments, visualization comprises irradiating the sample or a targeted portion of a subject with targeted application of a quantity of light having a wavelength in the visible, far-red, or near-infrared range and a selected intensity, wherein the quantity of light is sufficient to produce fluorescence of the compound, and detecting any fluorescence emitted by the compound. Advantageously, the light has a wavelength at or near a maximum absorption wavelength of the compound according to Formula I. For example, the sample may be irradiated with light having a wavelength within a range of 600 nm to 2500 nm, such as from 600-900 nm, or 600-700 nm. In some embodiments, the light source is a laser. Suitable light intensities may range from 1 mW/cm$^2$ to 1000 mW/cm$^2$, such as 1-750 mW/cm$^2$ or 300-700 mW/cm$^2$, depending on the target site and method of application. Near-infrared light sources can be obtained from commercial sources, including Thorlabs (Newton, N.J.), Laser Components, USA (Hudson, N.H.), ProPhotonix (Salem, N.H.) and others. In some embodiments, the effective quantity of far-red or NIR light is 10-250 J, such as 10-200 J, 10-150 J, or 10-100 J.

In some embodiments, visualization may include techniques such as fluoroscopy, single-molecule localization microscopy (SMLM), photo-activated localization microscopy (PALM), stochastic optical reconstruction microscopy (STORM), direct stochastic optical reconstruction microscopy (dSTORM), biplane imaging (BP), temporal radial-aperture based intensity estimation (TRABI), fluorescence resonance energy transfer (FRET), and combinations thereof.

In some embodiments, an effective amount of a compound according to Formula I or a pharmaceutical composition comprising the compound is administered to a subject suspected of having a condition that may be detected and/or evaluated by visualizing a fluorophore bound to a target (e.g., a tumor) within the subject. Advantageously, the compound according to Formula I may include a targeting agent capable of binding to the target within the subject. Administration is performed by any suitable method, e.g., intravenous, intra-arterial, intramuscular, intratumoral, or subcutaneous injection, or oral, intranasal, or sublingual administration. The administered compound is subsequently irradiated by targeted application of a quantity of light having a wavelength in the far-red or near-infrared range and a selected intensity to a target area of the subject, wherein the quantity of light is sufficient to excite the compound according to Formula I. When irradiating a target area (e.g., an area proximate a tumor), the effective quantity of far-red or NIR light may be 1-250 $J/cm^2$, such as 1-250 $J/cm^2$, such as 5-250 $J/cm^2$, 10-250 $J/cm^2$, 10-200 $J/cm^2$, 10-150 $J/cm^2$, 10-100 $J/cm^2$, or 30-100 $J/cm^2$. Any fluorescence from the compound in the targeted portion of the subject is detected, thereby diagnosing the subject as having the condition.

In certain theranostic embodiments, the condition is a tumor and the targeted portion of the subject includes the tumor site. The administered compound is visualized by exposing the tumor to light having a wavelength and intensity sufficient to induce fluorescence of the compound. Irradiation may be performed by external application of light to a targeted area of a subject. Far-red or NIR light is capable of penetrating transcutaneously into tissue to a depth of several centimeters. In other embodiments, irradiation may be performed by internal application of light, such as by using an endoscope, a fiber optic catheter, or an implantable fluorescence device. Internal application may be used when the target tissue, such as a tumor, is located at a depth that is unsuitable for external light application. For example, an endoscope may be used for light delivery into the lungs, stomach, or bladder. In some examples, the tumor site is exposed by surgical incision prior to exposing the tumor to light. The tumor may be excised using the area of fluorescence as guidance. In one embodiment, at least a portion of the tumor is excised from the subject before administering the therapeutically effective amount of the compound or the pharmaceutical composition comprising the compound to the subject. In an independent embodiment, the therapeutically effective amount of the compound or the pharmaceutical composition comprising the compound is administered to the subject before surgical excision of the tumor or a portion thereof.

The surface area for light application is generally selected to include target tissue, e.g., a tumor or portion of a tumor, or an area of skin external to the target tissue. When targeted application of external light is desired for an in vivo biological sample, the surface area can be controlled by use of an appropriate light applicator, such as a micro-lens, a Fresnel lens, or a diffuser arrangement. For targeted internal light application, a desired endoscope or fiber optic catheter diameter can be selected. In some applications, an indwelling catheter filled with a light scattering solution may be internally placed proximate the target tissue, and an optical fiber light source may be inserted into the catheter (see, e.g., Madsen et al., *Lasers in Surgery and Medicine* 2001, 29, 406-412).

In another embodiment, an in vitro or ex vivo evaluation may be performed to determine whether a compound according to Formula I will effectively bind to a tissue sample obtained from a subject having, or suspected of having, a condition that may be visualized by the compound. The compound comprises a targeting agent thought to be capable of binding to or associating with a target molecule indicative of or associated with the condition. In one non-limiting example, the targeting agent is a receptor ligand or antibody capable of binding to a target receptor. The compound is combined with the tissue sample, and the sample is subsequently irradiated with an effective amount of near-IR light.

In one embodiment, the tissue sample is washed to remove excess, unbound compound, and fluorescence of the tissue sample is assessed. Fluorescence indicates that the compound has bound to the tissue sample.

In certain embodiments, a compound according to Formula I may be utilized to visualize shapes and/or structures within a cell. A compound according to Formula I may include a targeting agent capable of binding to a desired component within a cell, e.g., a fixed or permeabilized cell. For example, the compound may include phalloidin as a targeting agent that binds to F-actin. Visualization of F-actin is useful for showing the overall shape and structure of a cell.

In an independent embodiment, a compound according to Formula I may be utilized to detect and/or measure the presence of reactive oxygen species (ROS) including superoxide and hydroxide radicals, in a sample. ROS have been implicated in a variety of inflammatory diseases, such as cancer and atherosclerosis. ROS detection can be performed in vitro, ex vivo, or in vivo. In certain embodiments, the compound may be reduced prior to contacting a sample with the compound. ROS present in the sample may oxidize the compound to recreate the fluorophore, which is detected by any suitable method. Fluorescence indicates the presence of ROS in the sample. The intensity of the fluorescence may be correlated to the concentration of ROS in the sample.

VI. EXAMPLES

General Materials and Methods

All commercially obtained reagents were used as received. 2,3,3-trimethyl indoline (S1), malonaldehyde bis (phenylimine) monohydrochloride, Grubb's $2^{nd}$ generation and Hoyveda-Grubbs $2^{nd}$ generation catalysts were purchased from Sigma-Aldrich (St. Louis, Mo.). Acrolein dimethyl acetal (2) was purchased from TCI America (Portland, Oreg.). 4-hydrazinylbenzoic acid (S5) was ordered from Oakwood Chemical (Estill, S.C.). 2-(2-bromoethyl)-1,3-dioxolane was purchased from Acros Organics (Geel, Belgium). $NH_2$-$PEG_8$-COOH was purchased from Thermo Scientific (Waltham, Mass.). Aminophalloidin tosylate was purchased from Enzo, Inc. (Farmingdale, N.Y.). Compounds S2, S4, and S8 were synthesized according to known procedures (Hanessian et al., *J. Am. Chem. Soc.* 2004, 126 (19), 6064-71; Hall et al., *Nucleic Acids Res.* 2012, 40 (14), e108; Park et al., *Bioconjugate Chem.* 2012, 23 (3), 350-362).

Normal phase (60 Å, 20-40 m, RediSep® Rf Gold® silica or 60 Å, 35-70 m, RediSep® Rf silica) and reversed phase (100 Å, 20-40 micron particle size, RediSep® Rf Gold® Reversed-phase C18 or C18Aq) flash column chromatography was performed on a CombiFlash© Rf 200i (Teledyne Isco, Inc., Lincoln, Nebr.). Reversed-phase preparative HPLC was performed using an Agilent 1260 Infinity II LC system utilizing a SunFire Prep C18 column (100 Å, 5 m, 10×150 mm) obtained from Waters, Co (Milford, Mass.). High-resolution LC/MS analyses were conducted on a Thermo-Fisher LTQ-Orbitrap-XL hybrid mass spectrometer system with an Ion MAX API electrospray ion source in negative ion mode. Analytical LC/MS was performed using a Shimadzu LCMS-2020 Single Quadrupole utilizing a Kinetex C18 column (100 Å, 2.6 m, 2.1×50 mm) obtained from Phenomenex, Inc (Torrance, Calif.). Runs employed a gradient of 0-90% MeCN/0.1% aqueous formic acid over 4.5 min at a flow rate of 0.2 mL/min. $^1$H NMR and $^{13}$C NMR spectra were recorded on Bruker spectrometers (at 400 or 500 MHz or at 100 or 125 MHz) and are reported relative to deuterated solvent signals. Data for $^1$H NMR spectra are reported as follows: chemical shift (6 ppm), multiplicity, coupling constant (Hz), and integration. Data for $^{13}$C NMR spectra are reported in terms of chemical shift. Absorbance curves were obtained on a Shimadzu UV-2550 spectrophotometer operated by UVProbe 2.32 software. Molar absorption coefficients (F) were determined in PBS (50 mM, pH 7.4) or methanol (MeOH) using Beer's law, from plots of absorbance vs. concentration. Measurements were performed in 10 mm path length quartz cuvettes (Hellma 111-QS) that were maintained at room temperature, and reported values are averages (n≥3). Fluorescence traces were recorded on a PTI QuantaMaster steady-state spectrofluorimeter operated by FelixGX 4.2.2 software, with 4 nm excitation and emission slit widths, and a 0.1 s integration rate. A Quantaurus-QY spectrometer (Hamamatsu, model C11374) was used to determine absolute fluorescence quantum yields ($\Phi_F$) (Suzuki et al., *Phys. Chem. Chem. Phys.* 112009, 9850-9860). This instrument uses an integrating sphere to measure photons absorbed and emitted by a sample. Measurements were carried out at a concentration of 250 nM in either MeOH or PBS (50 mM, pH 7.4) and self-absorption corrections were performed using the instrument software. Reported values are averages (n≥5). Data analysis and curve fitting were performed using MS Excel 2011 and GraphPad Prism 7. Light intensity measurements were performed with a Thorlabs PM200 optical power and energy meter fitted with an S120VC standard Si photodiode power sensor (200-1100 nm, 50 nW-50 mW). See *JOC Standard Abbreviations and Acronyms* for abbreviations (http://pubs.acs.org/paragonplus/submission/joceah/-joceah_abbreviations.pdf).

Single-molecule imaging was performed on a custom-built objective-type TIRF setup as described elsewhere (van de Linde et al., *Nature Protocols* 2011, 6:991), employing highly inclined illumination. An inverted microscope (IX71, Olympus) equipped with a nosepiece stage (IX2-NPS, Olympus) and a 60× oil objective (NA 1.45 PlanApo, Olympus) was used. TRABI-Biplane imaging was performed as described elsewhere (Franke et al., *Nature Methods* 2017 14:41). In brief, a two-channel image splitter with twofold magnification (TwinCam, Cairn Research) equipped with a 50/50 beamsplitter (Cairn Research) and two EMCCD cameras (Ixon 897 and Ixon Ultra 897, Andor), whose focal planes were separated by 300 nm were used. Cameras were synchronized by a pulse generator (DG535, Stanford Research Systems). 3D calibration experiments were performed by moving the objective with a piezo scanner (Pifoc, Physik Instrumente) driven with a LVPZT servo controller (E-662, Physik Instrumente). Z-coordinates from TRABI-Biplane imaging were corrected for the refractive index mismatch by a scaling factor of 0.71 (refractive index of buffer $n_b$=1.34 and substrate (glass) $n_s$=1.52, numerical aperture of NA=1.45).

Example 1

Exemplary Syntheses for Conformationally Restricted Pentamethine Cyanine Fluorophores

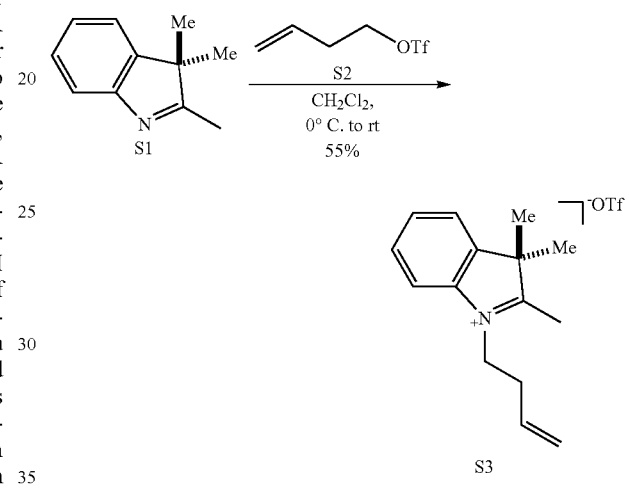

(S3): To a solution of 2,3,3-trimethyl indoline (S1, 2.0 g, 12.5 mmol, 1.0 eq) in CH$_2$Cl$_2$ (50 mL, 0.25M) at 0° C. was added S2 (3.0 g, 15 mmol, 1.2 eq). The solution was allowed to warm to room temperature and stand for 1 hour. The reaction volume was reduced to approximately 10 mL, and then purified by normal phase chromatography (24 g silica column, 0-15% MeOH/CH$_2$Cl$_2$) to afford S3 (2.5 g, 6.9 mmol, 55%) as a dark purple solid. $^1$H NMR (400 MHz, CDCl$_3$) δ 7.71-7.65 (m, 1H), 7.62-7.54 (m, 3H), 5.82 (ddt, J=17.3, 10.1, 7.3 Hz, 1H), 5.07 (ddd, J=10.1, 1.5, 0.9 Hz, 1H), 4.90 (dq, J=17.0, 1.4 Hz, 1H), 4.65 (t, J=6.7 Hz, 2H), 2.82 (s, 3H), 2.74 (q, J=6.9 Hz, 2H), 1.57 (s, 6H). $^{13}$C NMR (101 MHz, CDCl$_3$) δ 196.7, 141.6, 140.7, 132.2, 130.1, 129.5, 123.2, 120.3, 115.4, 54.6, 47.6, 32.2, 23.2, 14.9. HRMS (ESI) calculated for C$_{15}$H$_{20}$N (M$^+$) 214.1590, observed 214.1588.

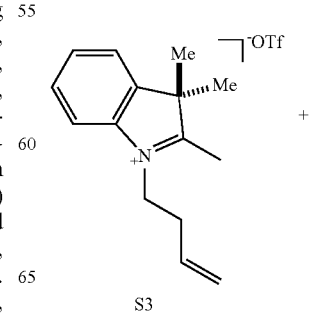

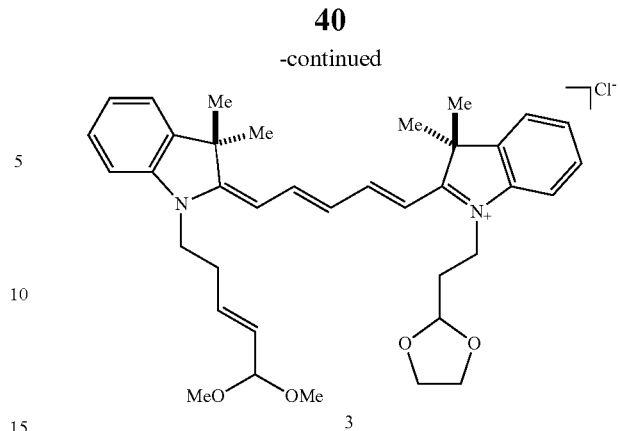

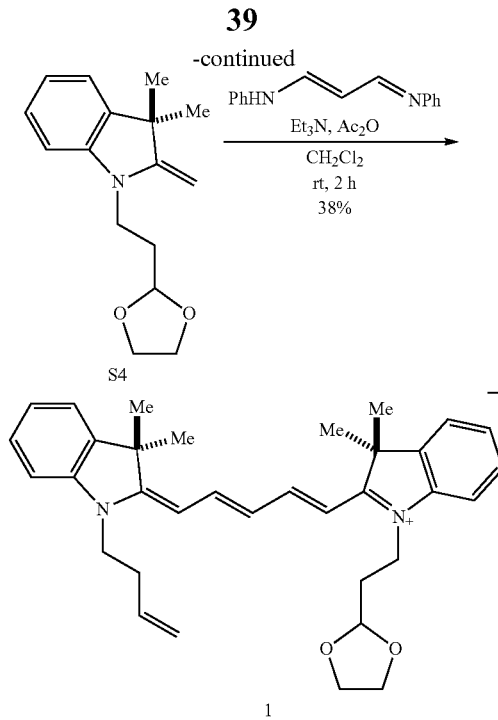

(1): To a solution of S3 (1.0 g, 5.0 mmol, 1.0 eq), S4 (1.3 g, 5.0 mmol, 1.0 eq), malonaldehyde bis (phenylimine) monohydrochloride (1.3 g, 5.0 mmol, 1.0 eq), and Et$_3$N (3.6 mL, 25 mmol, 5 eq) in CH$_2$Cl$_2$ (50 mL) was added Ac$_2$O (1.4 mL, 15 mmol, 3 eq). The solution was allowed to stand for 2 hours at room temperature. To the dark blue solution was then added aqueous NaI (50 mL, 0.4 M). The mixture was stirred vigorously for 18 hours and separated with CH$_2$Cl$_2$ (2×100 mL), dried over NaHSO$_4$ and concentrated under reduced pressure. The resulting blue residue was purified by normal phase column chromatography (40 g silica column, 25-75% ethyl acetate/CH$_2$Cl$_2$) to provide 1 (2$^{nd}$ eluting peak) as a blue solid (1.20 g, 1.9 mmol, 38%). $^1$H NMR (400 MHz, CD$_3$OD) δ 8.27 (td, J=13.1, 3.0 Hz, 2H), 7.51 (d, J=7.4 Hz, 2H), 7.43 (t, J=7.7 Hz, 2H), 7.32 (d, J=8.0 Hz, 2H), 7.28 (t, J=7.5 Hz, 2H), 6.65 (t, J=12.4 Hz, 1H), 6.34 (dd, J=13.7, 6.1 Hz, 2H), 5.92 (ddt, J=17.2, 10.1, 7.1 Hz, 1H), 5.14-5.03 (m, 2H), 5.01 (t, J=3.9 Hz, 1H), 4.25 (dt, J=14.6, 7.0 Hz, 4H), 4.02-3.81 (m, 4H), 2.62 (q, J=7.0 Hz, 2H), 2.21 (td, J=7.1, 3.9 Hz, 2H), 1.74 (s, 12H). $^{13}$C NMR (101 MHz, CD$_3$OD) δ 173.6, 173.2, 154.1, 154.0, 142.1, 142.1, 141.2, 141.2, 133.7, 128.3, 128.2, 125.2, 124.8, 124.8, 120.0, 122.0, 117.4, 110.9, 110.6, 103.5, 103.1, 101.6, 64.7, 49.2, 49.2, 42.7, 38.6, 31.6, 30.2, 26.7, 26.3. HRMS (ESI) calculated for C$_{34}$H$_{41}$N$_2$O$_2$ (M$^+$) 509.3163, observed 509.3157.

(3): To a dark blue solution of 1 (80 mg, 0.13 mmol, 1.0 eq) and Grubb's 2″a generation catalyst (33 mg, 0.039 mmol, 0.3 eq) in CH$_2$Cl$_2$ (16 mL, 0.01 M) was added acrolein dimethyl acetal (2, 149 μL, 1.3 mmol, 10 eq) under argon after degassing with vacuum. This reaction was refluxed at 40° C. for 5.5 hours under argon and static vacuum, which was reapplied approximately once per hour. After cooling to room temperature, saturated aqueous NaCl (20 mL) was added and stirred vigorously for 18 hours. The biphasic mixture was then separated, extracted with CH$_2$Cl$_2$ (3×20 mL), dried over Na$_2$SO$_4$, and evaporated under reduced pressure. The dark blue residue was purified by normal phase chromatography (12 g silica column, 0-20% MeOH/CH$_2$Cl$_2$) to provide 3 (2$^{nd}$ eluting peak, 37 mg, 0.060 mmol, 48%). The first eluting peak, which contained impure product, was combined and again stirred overnight with saturated aqueous NaCl (20 mL). The organic extraction in CH$_2$Cl$_2$ and normal phase purification was repeated to yield 3 (11 mg, 0.018 mmol, 14%). The purified product from both columns was combined to afford 3 (48 mg, 0.078 mmol, 62%) as a blue solid. $^1$H NMR (500 MHz, CD$_3$OD) δ 8.27 (td, J=13.1, 5.9 Hz, 2H), 7.53-7.49 (m, 2H), 7.46-7.40 (m, 2H), 7.36-7.25 (m, 4H), 6.64 (t, J=12.4 Hz, 1H), 6.33 (d, J=13.7 Hz, 2H), 5.91 (dt, J=14.9, 7.2 Hz, 1H), 5.44 (dd, J=15.6, 5.1 Hz, 1H), 5.00 (t, J=3.8 Hz, 1H), 4.59 (d, J=5.1 Hz, 1H), 4.26 (dt, J=10.8, 7.0 Hz, 4H), 3.92 (dt, J=51.0, 7.0 Hz, 4H), 3.16 (s, 6H), 2.65 (q, J=6.7 Hz, 2H), 2.21 (q, J=7.0 Hz, 2H), 1.74 (d, J=3.2 Hz, 12H). $^{13}$C NMR (101 MHz, CD$_3$OD) δ 173.5, 173.4, 154.1, 142.2, 142.1, 141.2, 141.2, 130.4, 130.0, 128.3, 128.3, 125.3, 124.8, 124.8, 122.0, 122.0, 110.9, 110.7, 103.5, 103.1, 103.0, 101.6, 64.7, 51.9, 49.2, 49.2, 42.5, 38.6, 30.2, 30.0, 26.6, 26.3. HRMS (ESI) calculated for C$_{37}$H$_{47}$N$_2$O$_4$ (M$^+$) 583.3530, observed 583.3536.

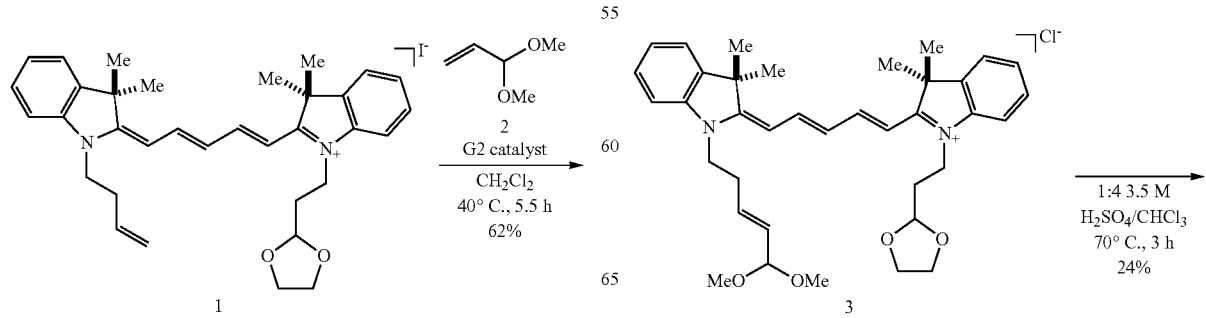

-continued

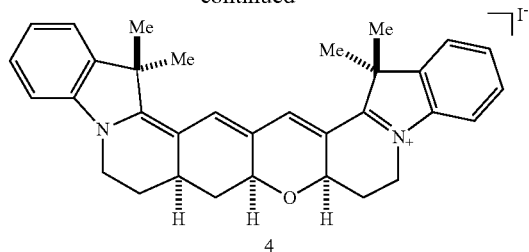

4

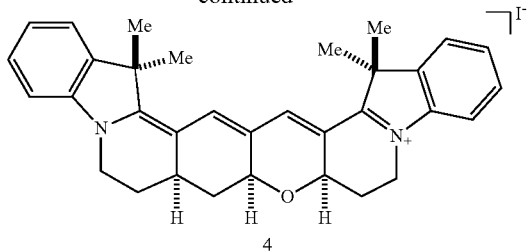

4

Figure 4:
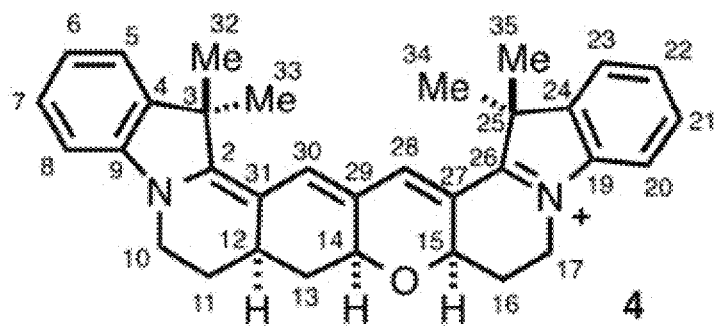
FIG. 4 shows a chemical structure and NMR analysis of an exemplary conformationally restricted pentamethine cyanine fluorophore (compound 4).

(4): In a sealed vial, aqueous $H_2SO_4$ (3.5 M, 1.3 mL) was added to a dark blue solution of 3 (37 mg, 0.059 mmol) in $CHCl_3$ (5.0 mL). This biphasic mixture (1:4 20% $H_2SO_4$/$CHCl_3$) was stirred at 70° C. for 3 hours, at which time LC/MS analysis revealed complete consumption of starting material. The resulting solution was quenched with saturated aqueous $NaHCO_3$ (20 mL), extracted with $CH_2Cl_2$ (4×10 mL), and dried over $Na_2SO_4$. The solvent was evaporated under reduced pressure and the blue-green residue was purified with normal phase chromatography (12 g silica gold column, 0-15% $MeOH/CH_2Cl_2$). The resulting product was dissolved in 1:1 aqueous NaI (1.0 M, 15 mL) and $CH_2Cl_2$ (15 mL), and stirred vigorously at room temperature for 5 hours. The biphasic mixture was separated, extracted with $CH_2Cl_2$ (3×10 mL $CH_2Cl_2$), and dried in vacuo. The resulting residue was eluted from a pipet packed with silica (10% $MeOH/90\% CH_2Cl_2$) and evaporated under reduced pressure to afford 4 (8.64 mg, 0.014 mmol, 24%) as a blue solid. Compound 4 was a single diastereomer with syn-syn ring junction stereochemistry assigned by NMR analysis (FIG. 4). The calculations were performed using Spartan '14 (Wavefunction, Inc., Irvine, Calif.). Except for molecular mechanics and semi-empirical models, the calculation methods used in Spartan have been documented in Shao et al. (*Phys. Chem. Chem. Phys.* 2016, 8:3172). Conformational distribution was performed at the MMFF level. The three lowest energy conformers (within 20 kJ/mol of the lowest energy) in the previous step were subjected to geometry optimization using B3LYP/6-31G(d), EtOH solvent. (1 for syn-syn, 2 for syn-anti, 3 for anti-syn, 3 for anti-anti). The resulting minima are shown in FIG. 4. All three methine protons which are located at the ring junctions (positions 12, 14, and 15) exhibited 1D-NOESY interactions with the upfield axial α-nitrogen protons (3.88 (tq, J=13.3, 4.5 Hz, 2H)—position 10 and 17), consistent with the syn, syn diastereomer. Furthermore, none of these protons displayed an NOE to the downfield equatorial α-nitrogen protons (4.40-4.24 (m, 2H)—positions 10 and 17), which would be expected for at least one methine proton in any other diastereomeric structure. Also, consistent with the formation of the syn-syn diastereomer, the α-oxygen protons (positions 14 and 15) displayed nearly identical coupling constants, indicating these protons are in similar ring systems.

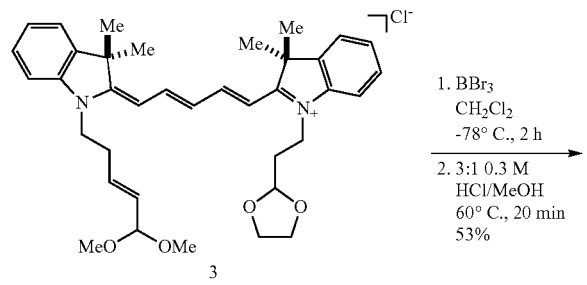

3

1. $BBr_3$
$CH_2Cl_2$
-78° C., 2 h 2. 3:1 0.3 M
HCl/MeOH
60° C., 20 min
53%

Figure 5:
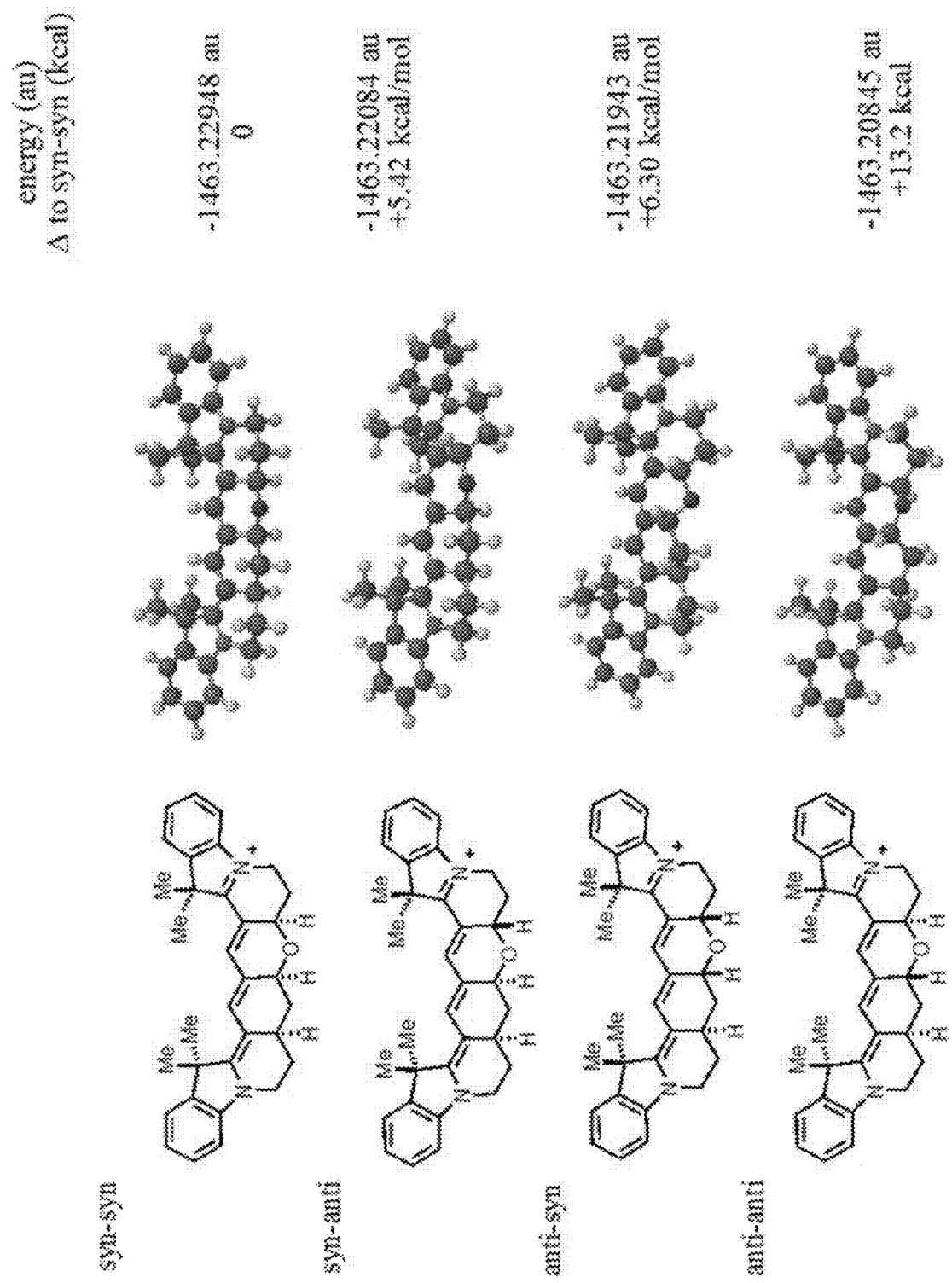
FIG. 5 shows diastereomers of compound 4 and their associated energies.

(4): To a solution of 3 (11.0 mg, 0.018 mmol, 1 eq) in anhydrous $CH_2Cl_2$ (1.8 mL, 0.01 M), degassed under argon and cooled to -78° C. (dry ice and acetone bath), $BBr_3$ (0.21 mL of a 1.0 M $CH_2Cl_2$ solution, 0.21 mmol, 12 eq) was slowly added. The reaction color rapidly transitioned from dark blue to red-brown upon $BBr_3$ addition. After stirring for 2 hours under argon at -78° C., the reaction was quenched with the addition of aqueous $NaHCO_3$ (0.5 M, 5 mL) and the blue color rapidly returned. Once warmed to room temperature, additional $CH_2Cl_2$ (10 mL) was provided and the biphasic mixture was stirred vigorously for 45 min. The light green/yellow aqueous layer was then extracted with $CH_2Cl_2$ (3×5 mL), and the combined dark blue organic solution was dried over $Na_2SO_4$ and evaporated under reduced pressure. This blue residue contained a diastereomeric mixture of 4 and a second compound (obtained in a variable ratio of ~1:1 to ~2:1). The inseparable mixture exhibited a single $[M]^+$ ion signal, complex NMR signals in the dihydropyran region, and a single far-red UV-vis absorbance maximum. The mixture was equilibrated to homogenous compound 4 as follows. The mixture was dissolved in MeOH (0.9 mL) and aqueous HCl (0.3 M, 2.7 mL), and stirred at 60° C. for 20 min. After cooling to room temperature, aqueous $NaHCO_3$ (0.5 M, 5 mL) and $CH_2Cl_2$ (10 mL) were added to form a biphasic mixture, which was stirred vigorously for 30 min. The light green/yellow aqueous layer was extracted with $CH_2Cl_2$ (10×5 mL), and the combined organic solution was dried over $Na_2SO_4$, and concentrated under reduced pressure. The blue residue was dissolved in $CH_2Cl_2$ (15 mL) and aqueous NaI (0.5 M, 10 mL) and stirred vigorously for 13 hours at room temperature. The biphasic mixture was separated, extracted with $CH_2Cl_2$ (2×10 mL), and dried over $Na_2SO_4$. After drying in vacuo, the residue was purified by normal phase chromatography (4 g silica gold column, 0-10% $MeOH/CH_2Cl_2$) to afford a blue solid of 4 as a single diastereomer (5.7 mg, 0.0095 mmol, 53%). $^1H$ NMR (400 MHz, $CD_3OD$) δ 7.93 (s, 1H), 7.86 (s, 1H), 7.57-7.36 (m, 4H), 7.37-7.16 (m, 4H), 4.67 (dd, J=11.5, 5.0 Hz, 1H), 4.61 (dd, J=11.4, 5.0 Hz, 1H), 4.40-4.24 (m, 2H), 3.88 (tq, J=13.3, 4.5 Hz, 2H), 2.84 (tt, J=12.3, 4.1 Hz, 1H), 2.58 (dt, J=11.7, 4.5 Hz, 1H), 2.49 (dt, J=11.7, 4.5 Hz, 1H), 2.41 (dt, J=13.3, 4.2 Hz, 1H), 2.01 (qd, J=12.6, 5.4 Hz, 1H), 1.82 (dd, J=12.6, 5.0 Hz, 1H), 1.78-1.74 (m, 12H), 1.48 (q, J=11.8 Hz, 1H). $^{13}C$ NMR (126 MHz, $CD_3OD$) δ 169.2, 165.8, 143.3, 142.0, 142.0, 141.5, 141.1, 140.3, 128.7, 128.3, 128.3, 125.3, 124.5, 121.9, 121.9, 114.0, 111.4, 110.2, 109.6, 72.2, 70.2, 49.1, 48.3, 42.9, 40.7, 35.1, 31.1, 27.2, 26.7, 26.7, 26.6, 26.1, 26.0. HRMS (ESI) calculated for $C_{33}H_{35}N_2O$ $(M^+)$ 475.2737, observed 475.2744. Computational analysis indicates the lowest energy diastereomer containing an anti-ring junction was diastereomeric to compound 4 adjacent to C5' of the polyene (FIG. 5). It was noted that simply subjecting compound 3 to the MeOH:HCl equilibration conditions provided only trace quantities of compound 4.

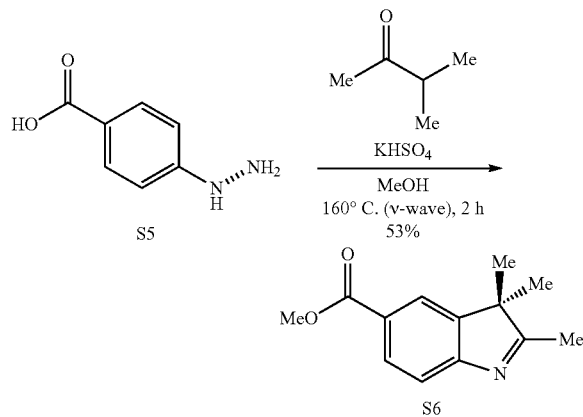

(S6): The following was placed in three separate sealed vials: 4-hydrazinyl-benzoic acid (S5, 610 mg, 4.0 mmol, 1.0 eq), 3-methyl-2-butanone (430 µL, 4.0 mmol, 1.0 eq), KHSO$_4$ (1.5 g, 12 mmol, 3.0 eq) and MeOH (15 mL). Each vial was heated to 160° C. for 2 hours by microwave. The combined contents of three vials were separated between saturated aqueous NaHCO$_3$ (100 mL) and CH$_2$Cl$_2$ (2×100 mL), dried (NaHSO$_4$) and concentrated under reduced pressure. The resulting residue was purified by normal phase chromatography (40 g silica column, 30-100% ethyl acetate/hexanes) to provide S6 (1.4 g, 6.3 mmol, 53%) as a tan oil. $^1$H NMR (400 MHz, CDCl$_3$) δ 8.06 (dd, J=8.1, 1.7 Hz, 1H), 7.99 (d, J=1.6 Hz, 1H), 7.58 (d, J=8.1 Hz, 1H), 3.95 (s, 3H), 2.34 (s, 3H), 1.36 (s, 6H). $^{13}$C (126 MHz, CDCl$_3$) δ 191.7, 167.3, 157.7, 145.7, 130.1, 126.9, 122.7, 119.6, 53.9, 52.1, 22.9, 15.7. HRMS (ESI) calculated for C$_{13}$H$_{16}$NO$_2$ (MH$^+$) calculated 218.1176, observed 218.1173.

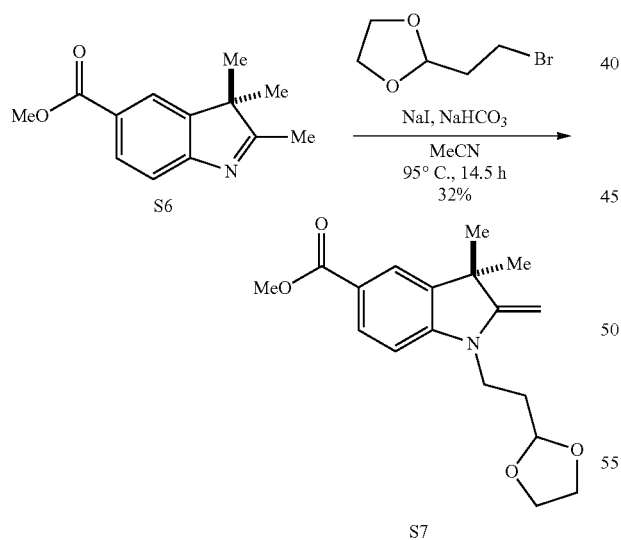

(S7): In a sealed vessel, S6 (6.0 g, 28 mmol, 1.0 eq) was combined with 2-(2-bromoethyl)-1,3-dioxolane (5.0 mL, 41 mmol, 1.5 eq), NaHCO$_3$ (4.6 g, 55 mmol, 2.0 eq), and NaI (6.2 g, 41 mmol, 1.5 eq) in MeCN (80 mL). The reaction was stirred at 95° C. for 14.5 hours as the solution color transitioned from orange to brown. The crude product was filtered over celite and concentrated under reduced pressure and the residue was purified by reversed-phase column chromatography (150 g C18 gold column, 0-80% MeCN/H$_2$O) to afford S7 (2.8 g, 8.9 mmol, 32%) as a dark green oil. $^1$H NMR (400 MHz, CDCl$_3$) δ 7.90 (dd, J=8.3, 1.8 Hz, 1H), 7.75 (d, J=1.7 Hz, 1H), 6.62 (d, J=8.3 Hz, 1H), 4.93 (t, J=4.5 Hz, 1H), 4.09 (d, J=2.3 Hz, 1H), 4.04-3.84 (m, 8H), 3.72 (t, J=7.2 Hz, 2H), 2.03 (td, J=7.5, 4.5 Hz, 2H), 1.36 (s, 6H). $^{13}$C NMR (126 MHz, CDCl$_3$) δ 167.6, 160.7, 149.8, 137.6, 131.1, 123.3, 120.2, 104.7, 102.5, 76.4, 65.1, 51.79, 43.81, 37.39, 30.23, 30.01. HRMS (ESI) calculated for C$_{18}$H$_{23}$NO$_4$ (MH$^+$) 318.1700, observed 318.1695.

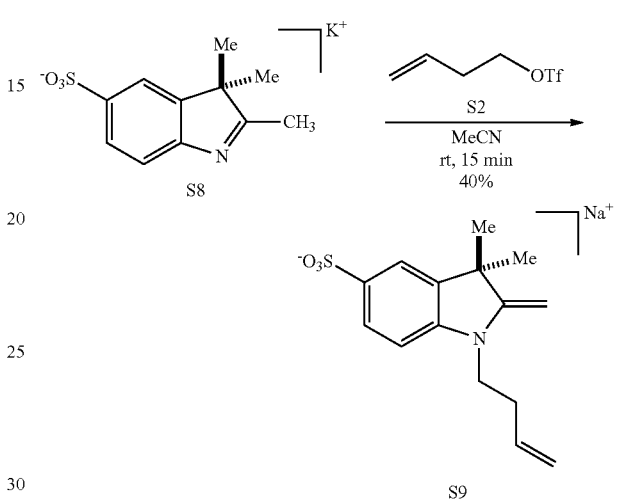

(S9): To a heterogenous mixture of S8 (4.6 g, 19 mmol, 1.0 eq) in MeCN (50 mL, 0.38 M) at room temperature was slowly added freshly-prepared neat 3-butenyl triflate (S2, 5.1 g, 25 mmol, 1.3 eq). After 15 min, the resulting dark mixture was treated with saturated aqueous NaHCO$_3$ (50 mL). The resulting mixture was filtered through celite and the volume of the resulting solution was reduced on a rotary evaporator (~50 mL). This solution was purified with reversed phase chromatography (150 g C18Aq gold column, 0-15% MeCN/H$_2$O) to provide clean S9 (2.2 g, 7.4 mmol, 40%) as a pink solid. $^1$H NMR (400 MHz, DMSO-d$_6$) δ 7.35 (dd, J=8.0, 1.7 Hz, 1H), 7.33 (d, J=1.5 Hz, 1H), 6.57 (d, J=8.1 Hz, 1H), 5.83 (ddt, J=17.1, 10.2, 7.0 Hz, 1H), 5.06 (dq, J=17.2, 1.4 Hz, 1H), 4.98 (dd, J=10.1, 2.1 Hz, 1H), 3.94 (d, J=1.8 Hz, 1H), 3.90 (d, J=1.8 Hz, 1H), 3.60 (t, J=7.1 Hz, 2H), 2.31 (q, J=6.9 Hz, 2H), 1.26 (s, 6H). $^{13}$C NMR (126 MHz, DMSO-d$_6$) δ 160.9, 145.9, 139.5, 136.3, 136.1, 125.9, 120.0, 117.3, 104.4, 75.2, 44.0, 41.2, 30.5, 30.2. HRMS (ESI) calculated for C$_{15}$H$_{19}$NO$_3$S (MH$^+$) 294.1158, observed 294.1155.

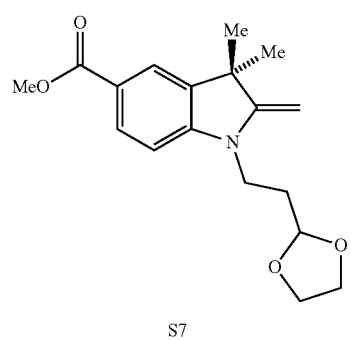

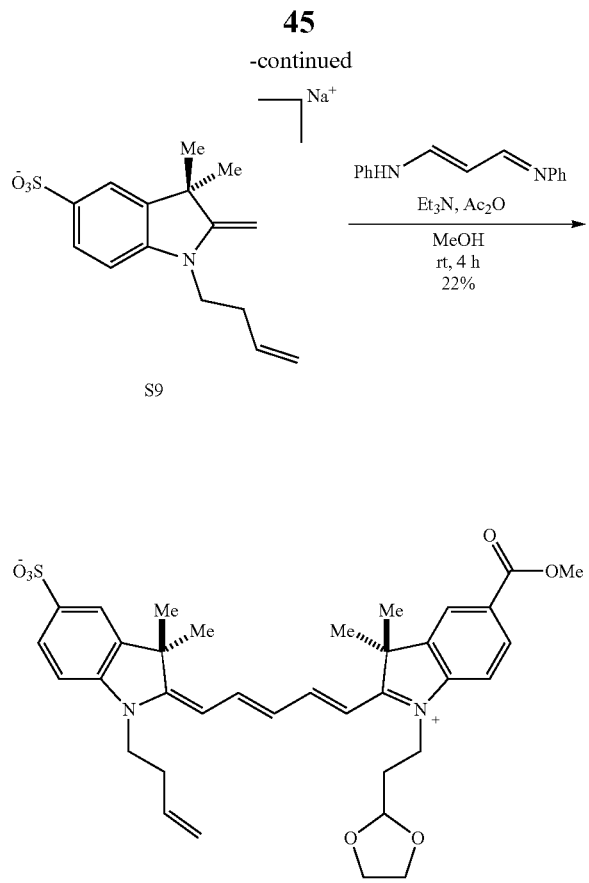

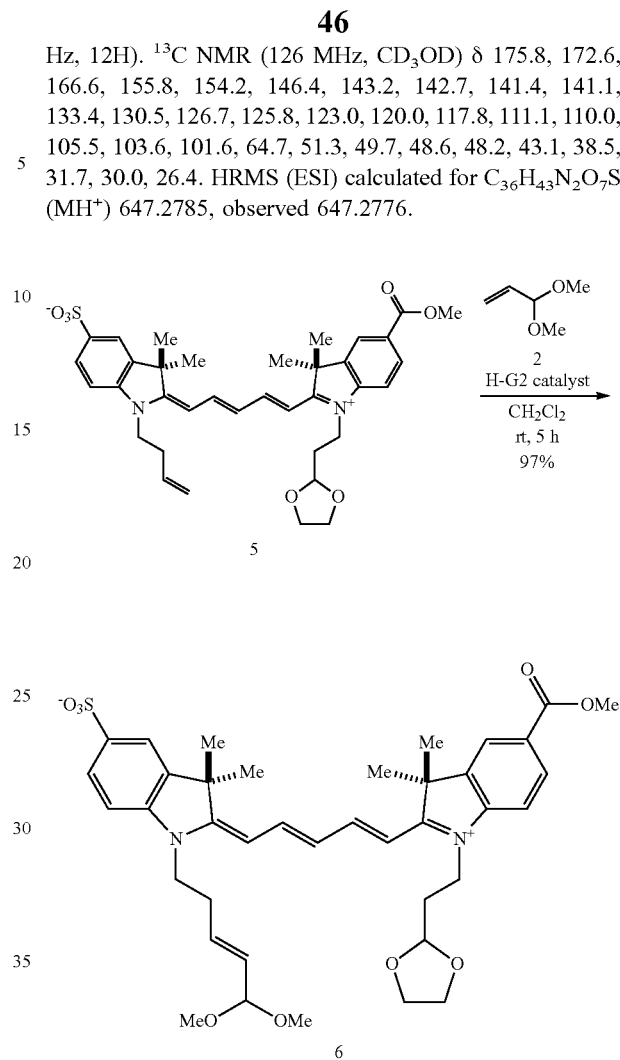

(9): To a solution of S9 (2.4 g, 7.7 mmol, 1.5 eq), S7 (1.5 g, 5.1 mmol, 1 eq), malonaldehyde bis(phenylimine) monohydrochloride (1.6 g, 6.1 mmol, 1.2 eq), and Et$_3$N (3.6 mL, 26 mmol, 5 eq) in MeOH (26 mL) was added acetic anhydride (1.0 mL, 10 mmol, 2 eq). While stirring at room temperature, additional acetic anhydride (1.0 mL, 10 mmol, 2 eq) was added over the first 1.5 hours of reaction approximately every 30 min. to total 3.9 mL (41 mmol, 8 eq). During the reaction, the solution color transitioned from red to green to purple and finally to dark blue. After 4 hours of total reaction time, LC/MS analysis revealed complete consumption of S7, and a mixture of the 3 possible cyanine products in an approximately 2:1:1 ratio of the unsymmetrical desired product to the undesired symmetrical cyanines. The dark blue solution was precipitated in 2:1 diethyl ether/hexanes (180 mL), centrifuged (6800 rpm, 8 min), and the supernatant was removed. This trituration was performed three times, and after drying in vacuo the dark blue residue was purified with reverse-phase chromatography (150 g gold C18 column, 0-80% MeCN/H$_2$O) to provide 5 (0.72 g, 1.1 mmol, 22%) as a dark blue solid. $^1$H NMR (400 MHz, CD$_3$OD) δ 8.35 (dt, J=17.0, 13.0 Hz, 2H), 8.14-8.06 (m, 2H), 7.97-7.89 (m, 2H), 7.44 (d, J=8.3 Hz, 1H), 7.34 (d, J=8.3 Hz, 1H), 6.72 (t, J=12.4 Hz, 1H), 6.48 (d, J=13.9 Hz, 1H), 6.34 (d, J=13.4 Hz, 1H), 5.90 (ddt, J=17.2, 10.2, 7.1 Hz, 1H), 5.10-5.02 (m, 2H), 4.99 (t, J=3.8 Hz, 1H), 4.30 (t, J=6.9 Hz, 2H), 4.26 (t, J=7.0 Hz, 2H), 3.98-3.84 (m, 7H), 2.64 (q, J=7.1 Hz, 2H), 2.21 (td, J=7.0, 3.8 Hz, 2H), 1.77 (d, J=5.6 Hz, 12H). $^{13}$C NMR (126 MHz, CD$_3$OD) δ 175.8, 172.6, 166.6, 155.8, 154.2, 146.4, 143.2, 142.7, 141.4, 141.1, 133.4, 130.5, 126.7, 125.8, 123.0, 120.0, 117.8, 111.1, 110.0, 105.5, 103.6, 101.6, 64.7, 51.3, 49.7, 48.6, 48.2, 43.1, 38.5, 31.7, 30.0, 26.4. HRMS (ESI) calculated for C$_{36}$H$_{43}$N$_2$O$_7$S (MH$^+$) 647.2785, observed 647.2776.

(10): To a solution of 5 (120 mg, 0.19 mmol, 1.0 eq) and Hoyveyda-Grubbs catalyst 2$^{nd}$ generation (58 mg, 0.093 mmol, 0.5 eq) in anhydrous CH$_2$Cl$_2$ (9.3 mL) was added acrolein dimethyl acetal (2, 110 μL, 0.95 mmol, 5.0 eq) under argon. The blue solution was stirred at room temperature for 5 hours with a closed reflux condenser under argon and static vacuum, which was reapplied approximately every 30 min. The resulting blue mixture was precipitated in 1:1 diethyl ether/hexanes (45 mL), centrifuged (7500 rpm, 5 min.), and decanted. After repeating this precipitation, the pellet was dried under high vacuum to afford 6 (130 mg, 0.18 mmol, 97%) as a dark blue solid that was used without further purification. $^1$H NMR (500 MHz, CD$_3$OD) δ 8.36 (q, J=13.7 Hz, 2H), 8.13-8.08 (m, 2H), 7.95-7.90 (m, 2H), 7.46-7.41 (m, 1H), 7.35 (dd, J=8.3, 2.2 Hz, 1H), 6.72 (t, J=12.4 Hz, 1H), 6.48 (d, J=13.8 Hz, 1H), 6.35 (d, J=13.4 Hz, 1H), 5.90 (ddd, J=14.6, 7.6, 6.5 Hz, 1H), 5.49-5.37 (m, 1H), 4.99 (t, J=3.8 Hz, 1H), 4.58 (dd, J=5.3, 1.0 Hz, 1H), 4.32 (t, J=6.9 Hz, 2H), 4.26 (t, J=7.1 Hz, 2H), 4.01-3.79 (m, 7H), 3.37 (s, 3H), 2.66 (td, J=8.0, 7.4, 5.3 Hz, 2H), 2.21 (td, J=7.0, 4.0 Hz, 2H), 1.81-1.75 (m, 12H). $^{13}$C NMR (126 MHz, MeOD) δ 175.7, 172.7, 166.6, 155.7, 154.2, 146.3, 143.3, 142.7, 141.4, 141.2, 130.8, 130.6, 129.7, 126.7, 126.7, 125.9, 123.0, 120.0, 111.1, 110.1, 105.6, 103.7, 102.8, 101.6, 64.7, 51.3, 49.6, 48.6, 48.4, 48.2, 43.1, 38.6, 30.0, 26.3. HRMS (ESI) calculated for $C_{39}H_{48}N_2O_9S$ (MH+) 721.3153, observed 721.3144.

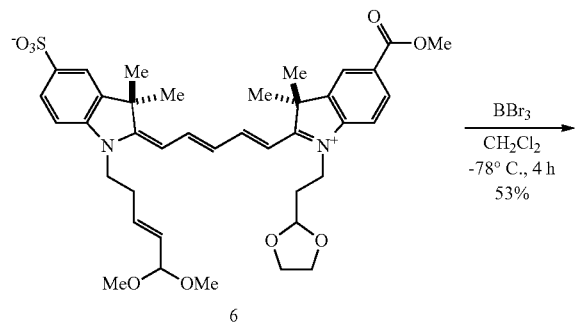

(S10): A dark blue solution of 6 (0.13 g, 0.18 mmol, 1 eq) in $CH_2Cl_2$ (12 mL, 0.015 M) was cooled to −78° C. (dry ice and acetone bath) and degassed under argon. $BBr_3$ (2.1 mL of a 1.0 M $CH_2Cl_2$ solution, 2.1 mmol, 12 eq) was added slowly and the reaction color transitioned to red-brown. The reaction was stirred under argon with the temperature maintained at −78° C. over 4 hours at which time the reaction was quenched with the addition of $H_2O$ (10 mL) and immediately returned to a blue color. LC/MS analysis revealed complete consumption of starting material. After warming to room temperature, the organic solvent was evaporated under reduced pressure. The remaining blue aqueous solution was purified by reverse-phase chromatography (30 g C18 gold column, 0-60% $MeCN/H_2O$) to yield a diastereomeric mixture of compound S10 (57 mg, 0.094 mmol, 53%) as a dark blue solid. HRMS (ESI) calculated for $C_{35}H_{36}N_2O_6S$ (MH+) 613.2367, observed 613.2360.

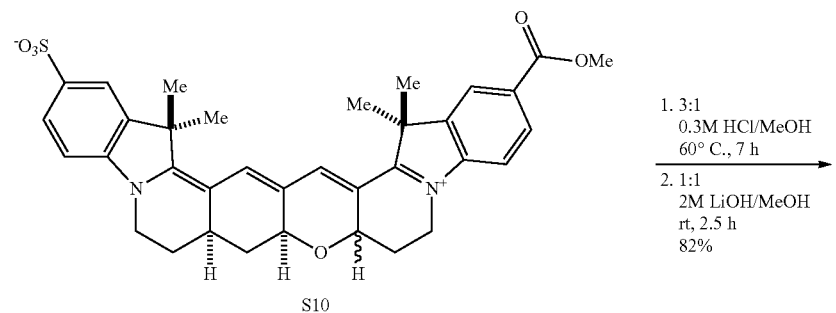

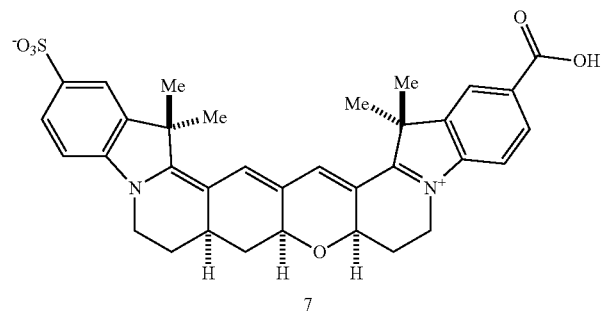

-continued

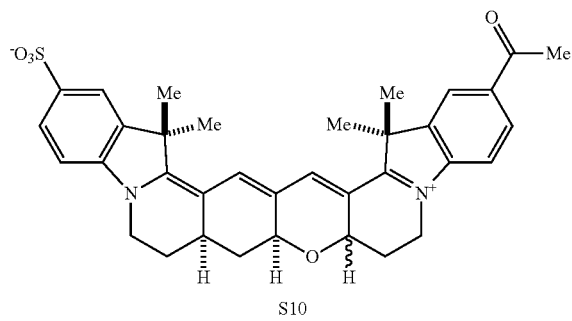

Figure 6:
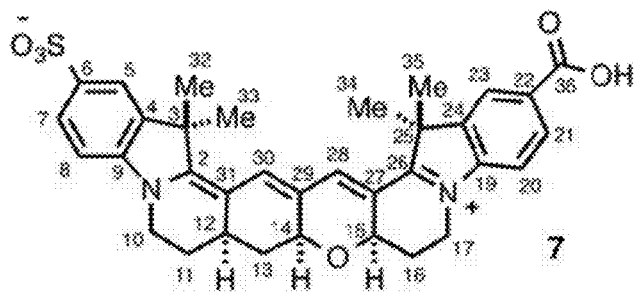
FIG. 6 shows a chemical structure and NMR analysis of an exemplary conformationally restricted, phalloidin-conjugated pentamethine cyanine fluorophore (compound 7).

(7): A diastereomeric mixture of S10 (43 mg, 0.070 mmol) was dissolved in MeOH (5.8 mL) and aqueous HCl (0.30 M, 17 mL). This reaction mixture was heated to 60° C. for 7 hours over which time the color transitioned from dark blue to a green-blue color. After cooling to room temperature, the reaction was dried under reduced pressure to yield a single diastereomer of S10 as confirmed by NMR analysis. This crude solid of the equilibrated methyl ester intermediate was redissolved in MeOH (3.5 mL) and aqueous LiOH (2.0 M, 3.5 mL). The resulting blue solution was stirred at room temperature for 2.5 hours, at which time LC/MS analysis revealed complete conversion to 7. Saturated aqueous $NaHCO_3$ (3.0 mL) was added to quench the reaction. After the removal of MeOH in vacuo, the crude aqueous mixture was purified by reverse-phase chromatography (30 g C18 gold column, 0-70% MeCN with 0.05% formic acid/H₂O with 0.05% formic acid), to afford 7 (34 mg, 0.057 mmol, 82%) as a blue solid. $^1$H NMR (500 MHz, DMSO-$d_6$) δ 8.08 (s, 1H), 8.04 (s, 1H), 7.99 (s, 1H), 7.95 (d, J=8.2 Hz, 1H), 7.89 (s, 1H), 7.69 (d, J=8.1 Hz, 1H), 7.36 (d, J=8.2 Hz, 1H), 7.23 (d, J=8.3 Hz, 1H), 4.57 (dd, J=11.4, 4.7 Hz, 1H), 4.51 (dd, J=11.3, 4.6 Hz, 1H), 4.34 (d, J=10.3 Hz, 1H), 4.24 (d, J=9.5 Hz, 1H), 3.89 (t, J=11.7 Hz, 1H), 3.80 (t, J=12.9 Hz, 1H), 2.75 (t, J=12.4 Hz, 1H), 2.43 (d, J=12.2 Hz, 1H), 2.35 (dd, J=7.0, 4.5 Hz, 1H), 2.28 (d, J=12.9 Hz, 1H), 1.88 (dd, J=12.2, 5.0 Hz, 1H), 1.77-1.62 (m, 13H), 1.34 (q, J=11.8 Hz, 1H). $^{13}$C NMR (126 MHz, DMSO-$d_6$) δ 169.4, 166.3, 162.4, 145.1, 143.9, 142.9, 140.4, 140.0, 139.3, 138.6, 129.2, 128.4, 124.9, 122.1, 118.8, 114.4, 109.7, 109.3, 107.9, 70.2, 68.4, 48.2, 46.3, 42.1, 39.4, 33.5, 29.2, 26.3, 25.9, 25.6, 25.4. HRMS (ESI) calculated for $C_{35}H_{36}N_2O_6S$ (MH$^+$) 599.2210, observed 599.2204. Compound 7 was a single diastereomer with syn-syn ring junction stereochemistry assigned by NMR analysis (FIG. 6). All three methine protons which are located at the ring junctions (positions 12, 14, and 15) exhibited 1D-NOESY interactions with the upfield axial α-nitrogen protons (3.88 (tq, J=13.3, 4.5 Hz, 2H))—position 10 and 17, consistent with the syn, syn diastereomer. Furthermore, none of these protons displayed an NOE to the downfield equatorial α-nitrogen protons (4.40-4.24 (m, 2H)—positions 10 and 17), which would be expected for at least one methine proton in any other diastereomeric structure. Also, consistent with the formation of the syn-syn diastereomer, the α-oxygen protons (positions 14 and 15) displayed nearly identical coupling constants, indicating these protons are in similar ring systems.

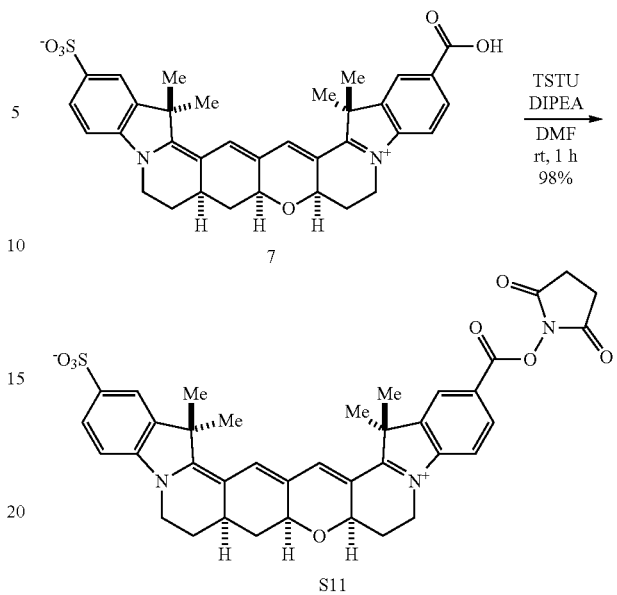

(S11): To a solution of 7 (6.0 mg, 0.010 mmol, 1 eq) in DMF (0.20 mL, 0.05 M) was added TSTU (4.5 mg, 0.015 mmol, 1.5 eq) and DIPEA (1.8 μL, 0.020 mmol, 2 eq). This blue solution was stirred at room temperature for 1.5 hours at which time LC/MS analysis revealed complete conversion to S11. The mixture was then precipitated in ether (14 mL), centrifuged (6000 rpm, 5 min), and the supernatant was decanted. After repeating this ether wash, the dark blue solid was dried in vacuo to afford S11 (6.9 mg, 0.0098 mmol, 98%), which was used without further purification.

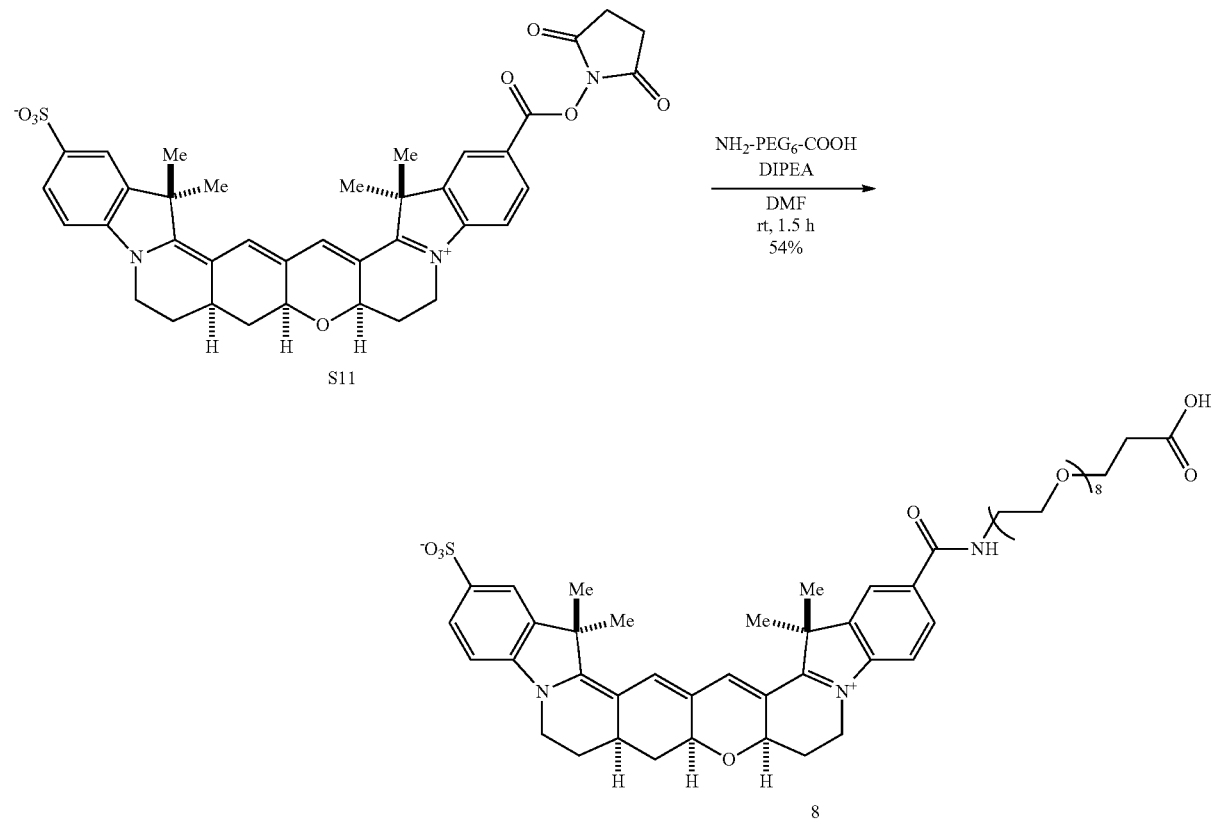

(8): To a solution of S11 (3.0 mg, 0.0043 mmol, 1 eq) in DMF (0.15 mL, 0.03 M) was added NH$_2$—PEG$_8$-COOH (2.3 mg, 0.0053 mmol, 1.2 eq) and DIPEA (N,N-diisopropylethylamine, 3.8 μL, 0.022 mmol, 5 eq). This blue solution was stirred at room temperature for 1.5 hours at which time LC/MS analysis revealed complete consumption of S12. The resulting solution was precipitated in 1:1 ether and hexanes (14 mL), centrifuged (4000 rpm, 5 min), and the supernatant was removed. This trituration was repeated, and the resulting blue residue was purified by reverse-phase chromatography (5.5 g C18Aq gold column, 0-70% MeCN/H$_2$O with 0.05% formic acid) to afford 8 (2.3 mg, 0.0023 mmol, 54%) as a blue solid. HRMS (ESI) calculated for C$_{53}$H$_{71}$N$_3$O$_{15}$S (MH$^+$) 1022.4679, observed 1022.4679.

(S12): To a solution of 8 (3.4 mg, 0.0033 mmol, 1 eq) in DMF (0.17 mL, 0.02 M) was added TSTU (1.5 mg, 0.0050 mmol, 1.5 eq) and DIPEA (1.7 μL, 0.010 mmol, 3 eq). This blue reaction mixture was stirred at room temperature for 2 hours at which time LC/MS analysis revealed complete conversion. The solution was precipitated in 1:1 ether/hexanes (14 mL), centrifuged (6500 rpm, 5 min), and the supernatant decanted. After repeating this precipitation, the blue residue was dried under reduced pressure to yield S12 (3.4 mg, 0.0030 mmol, 91%), which was used without further purification.

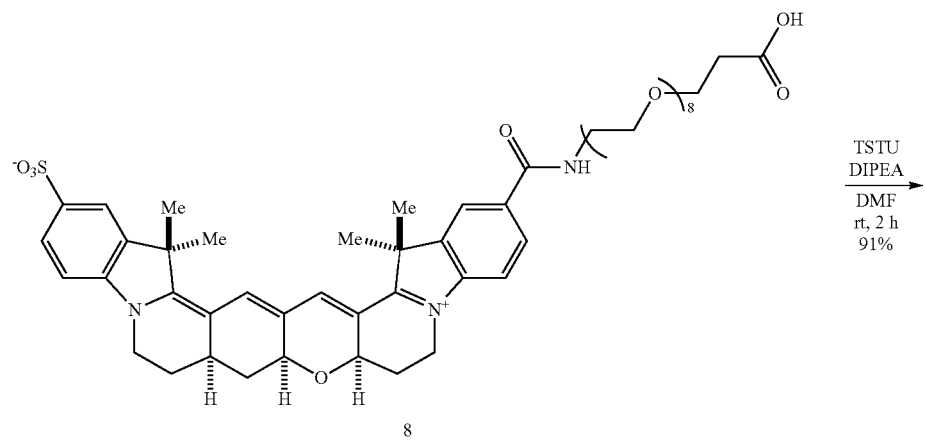

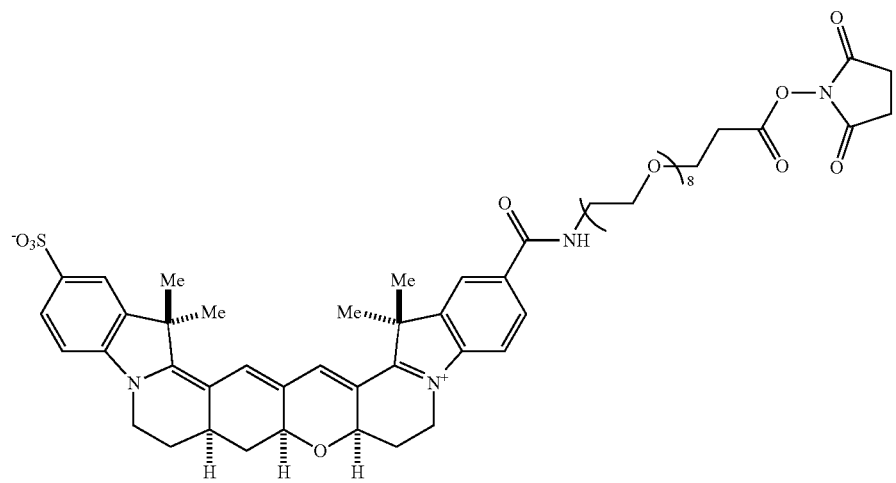

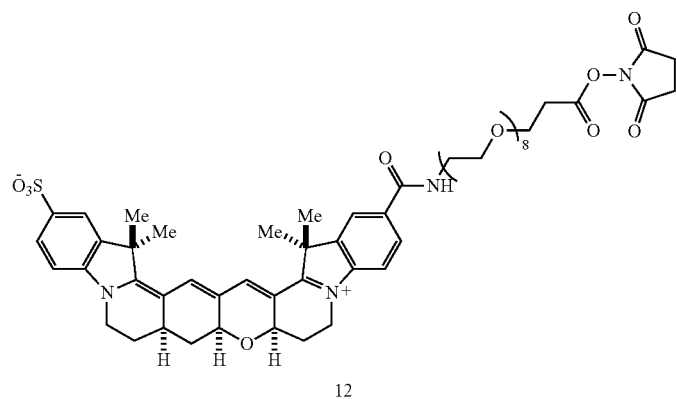

12

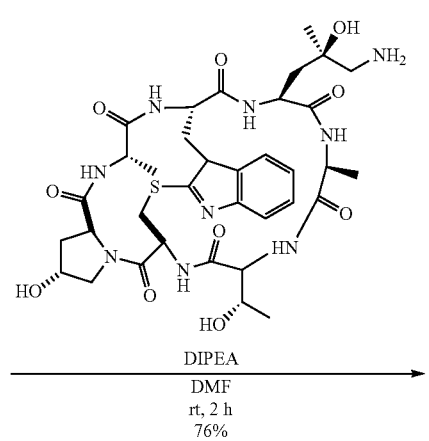

DIPEA
DMF
rt, 2 h
76%

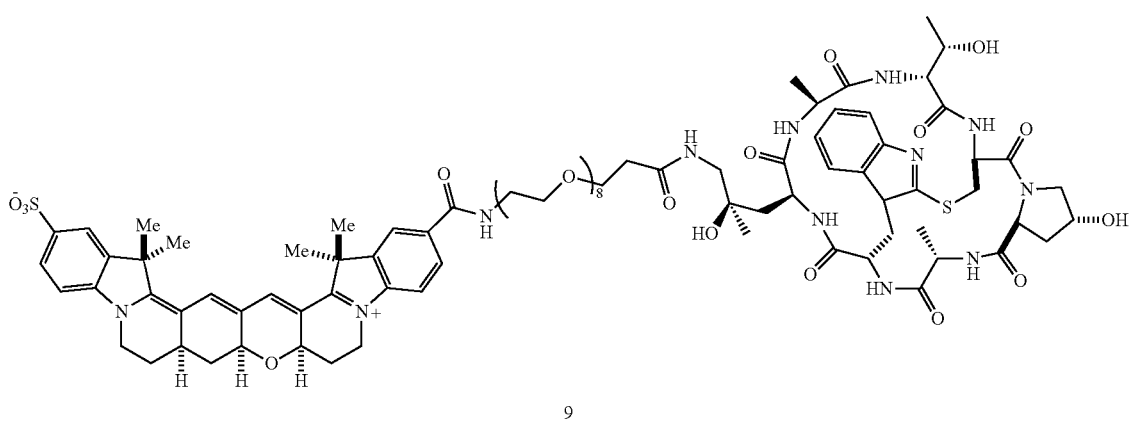

9

(9): To a solution of S12 (0.98 mg, 8.8×10⁻⁴ mmol, 1 eq) in DMSO (0.12 μL, 0.008 M) was added aminophalloidin tosylate (0.80 mg, 8.8×10⁻⁴ mmol, 1 eq) and DIPEA (0.73 L, 0.0042 mmol, 5 eq). This solution was stirred at room temperature for 1 hour at which time LC/MS analysis revealed consumption of aminophalloidin tosylate. The blue reaction mixture was precipitated in 1.5:1 ether/hexanes (1.4 mL), centrifuged (6000 rpm, 30 sec.), and the supernatant was removed. This trituration was performed a total of 3 times. After drying under reduced pressure, the blue residue was purified by reverse-phase preparative HPLC (20-95% MeCN/H$_2$O with 0.1% formic acid) and lyophilized to yield 9 (1.2 mg, 6.6×10⁻⁴ mmol, 76%) as a blue solid. HRMS (ESI) calculated for C$_{88}$H$_{118}$N$_{12}$O$_{24}$S$_2$ ([M+2H$^+$]$^{+2}$) 896.3984, observed 896.3971.

Example 2

Exemplary Syntheses for Conformationally Restricted Heptamethine Cyanine Fluorophores

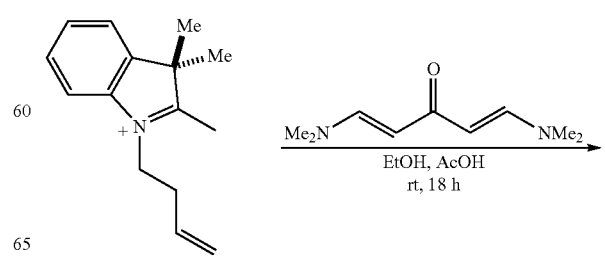

EtOH, AcOH
rt, 18 h

-continued

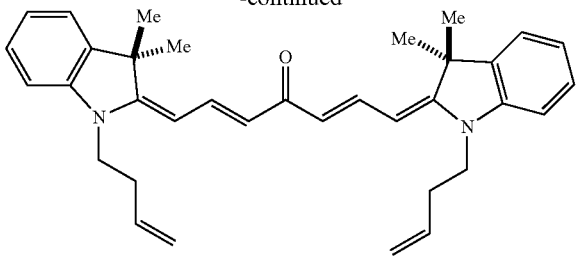

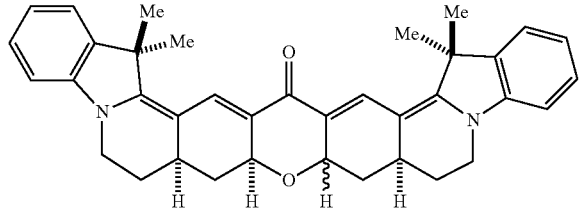

The indolenine and bis vinylogous amide were combined in 10:1 EtOH/AcOH and heated to 70° C. After 2 h, the mixture was extracted with $CH_2Cl_2$ and saturated sodium bicarbonate. The organic layers were dried with sodium sulfate, concentrated, and then purified with normal phase chromatography to provide the product.

A solution of the ketone in THF was treated with 1 N HCl. After 30 min, the mixture was extracted with $CH_2Cl_2$ and saturated sodium bicarbonate. The organic layers were dried with sodium sulfate, concentrated, and then used in the next step without purification.

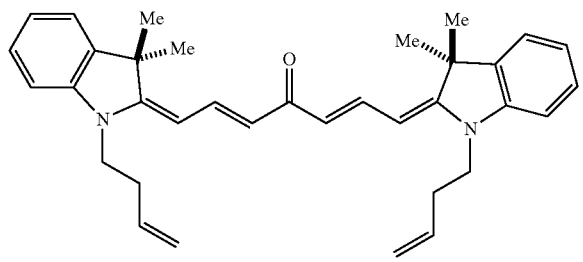

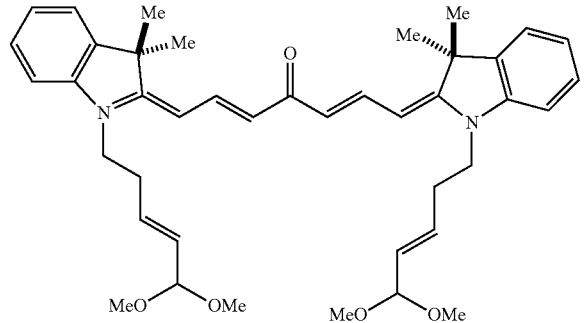

To a solution of the ketone in $CH_2Cl_2$ was added 10 equiv. of acrolein dimethyl acetal and 0.4 equiv. of HG-2. The solution was maintained at room temperature for 18 h, concentrated and purified by normal phase chromatography to provide the product.

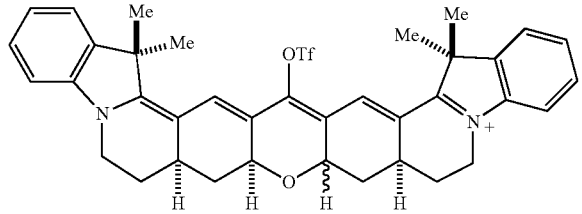

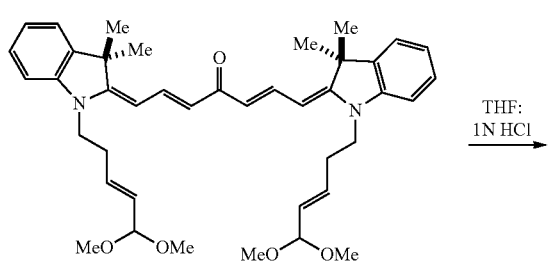

The ketone, $CH_2Cl_2$, and pyridine were cooled to −78° C. and $Tf_2O$ (trifluoromethanesulfonic anhydride) was added. The solution was allowed to warm to room temperature, and extracted with $CH_2Cl_2$ and saturated sodium bicarbonate. Purification with normal phase chromatography provided the product.

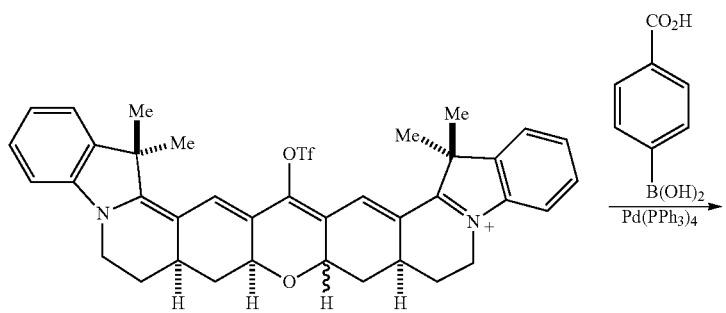

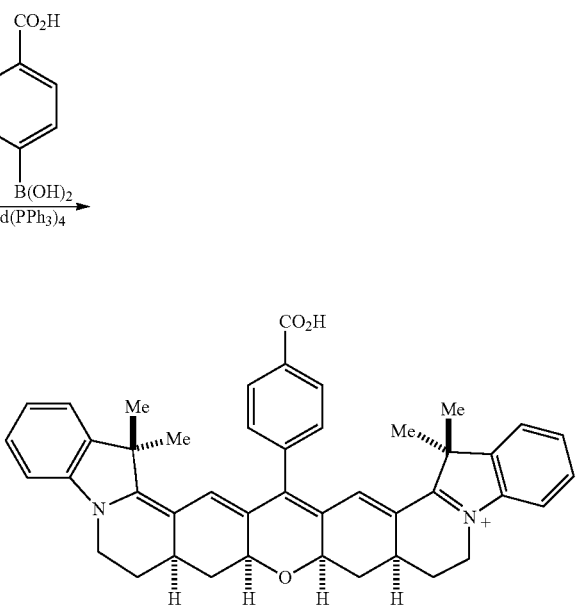

The triflate, boronic acid, and Pd(PPh$_3$)$_4$ were dissolved in 1:1 iPrOH:H$_2$O and heated to 90° C. After 18 h, the mixture was extracted with CH$_2$Cl$_2$ and saturated sodium bicarbonate. The organic layers were dried with sodium sulfate, concentrated, and then purified with normal phase chromatography to provide the product.

Example 3

Characterization of Conformationally Restricted Cyanine Fluorophores

The spectroscopic properties of conformationally restricted compounds 4 and 7 were compared to those of unrestricted compound 10.

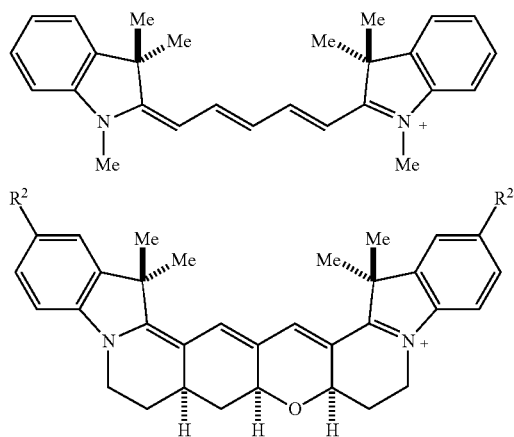

4: R$^1$ = R$^2$ = H
7: R$^1$ = SO$_3$, R$^2$ = CO$_2$H

TABLE 1

Spectroscopic Properties

| Cpd | $\lambda_{max}$ (nm) | $\varepsilon$ (M$^{-1}$cm$^{-1}$) | $\lambda_{em}$ (nm) | $\Phi_F$ | $\tau$ (ns) |
|---|---|---|---|---|---|
| 10[a] | 638 | 214,000 | 657 | 0.15 | 0.7 |
| 4[a] | 662 | 206,000 | 677 | 0.69 | 2.5 |
| 7 | 670[b] | 190,000 | 683[b] | 0.55[b] | 1.7[c] |

[a]in methanol;
[b]in pH 7.4 PBS;
[c]in H$_2$O

Compounds 4 and 7 exhibited the characteristic features of conformational restriction. The quantum yield is increased from 0.15 (MeOH) with compound 10 to 0.69 (MeOH) and 0.55 (PBS) with compounds 4 and 7, respectively (Table 1). This occurs with a shift in $\lambda_{max}$ of approximately 25 nm in both cases. Both fluorescence lifetime and quantum yield are largely solvent viscosity insensitive, unlike with the conventional pentamethine cyanine 10 that is subject to photoisomerization (Table 2).

TABLE 2

Fluorescence Lifetime ($\tau$) and Quantum Yield ($\Phi_F$) of Compounds 4 and 10

| | 4 | | 10 | |
|---|---|---|---|---|
| Solvent | $\tau$ (ns) | $\Phi_F$ | $\tau$ (ns) | $\Phi_F$ |
| MeCN | 2.8 | 0.92 | 0.7 | 0.13 |
| MeOH* | 2.5 | 0.69 | 0.7 | 0.15 |
| EtOH | 2.5 | 0.68 | 0.8 | 0.18 |
| Acetone | 2.9 | 0.90 | 0.8 | 0.19 |
| Glycerol | 2.3 | 0.66 | 1.8 | 0.24 |

Figure 7:
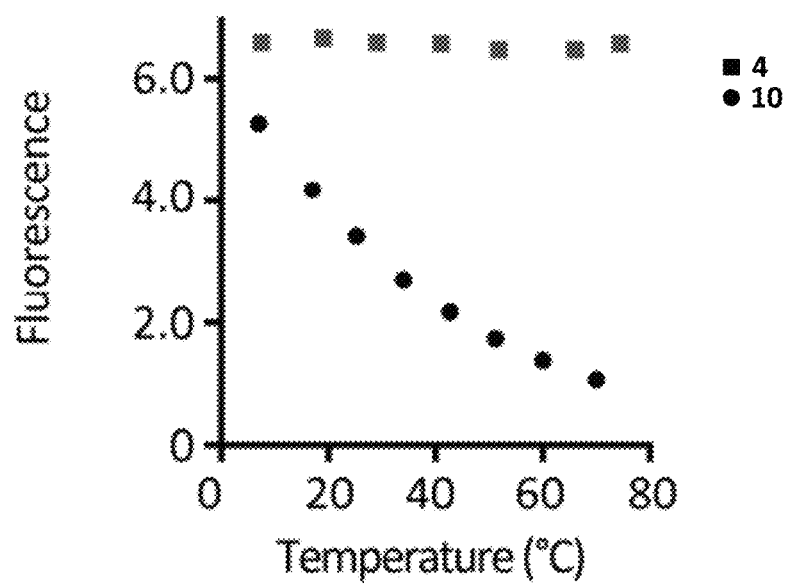
FIG. 7 is a graph showing the temperature dependence of fluorescence emission from compounds 4 (squares) and 10 (circles) in ethanol.

*Reference $\Phi_F$ by Integrating Sphere—other $\Phi_F$ values calculated by relative method Moreover, also unlike with compound 10 (circles), the emission of compound 4 (squares) is insensitive to temperature (FIG. 7). This is also due to photoisomerization in compound 10, which becomes more efficient at higher temperatures. The substantially longer lifetimes of compounds 4 and 7 relative to the unrestrained cyanine 10 point to significant potential for fluorescence lifetime imaging microscopy (FLIM).

Example 4

Single-Molecule Localization Microscopy with Conformationally Restricted Cyanine Fluorophores A central feature of single-molecule localization microscopy (SMLM) is the photoactivation or conversion of fluorophores between fluorescent and nonfluorescent states. Three modes of cyanine reactivity have been applied in this context: reversible formation of (1) thiol- and (2) phosphine-polyene adducts, as well as (3) sequential reduction/oxidation of the imine-like C2-N double bond.

Figure 8:
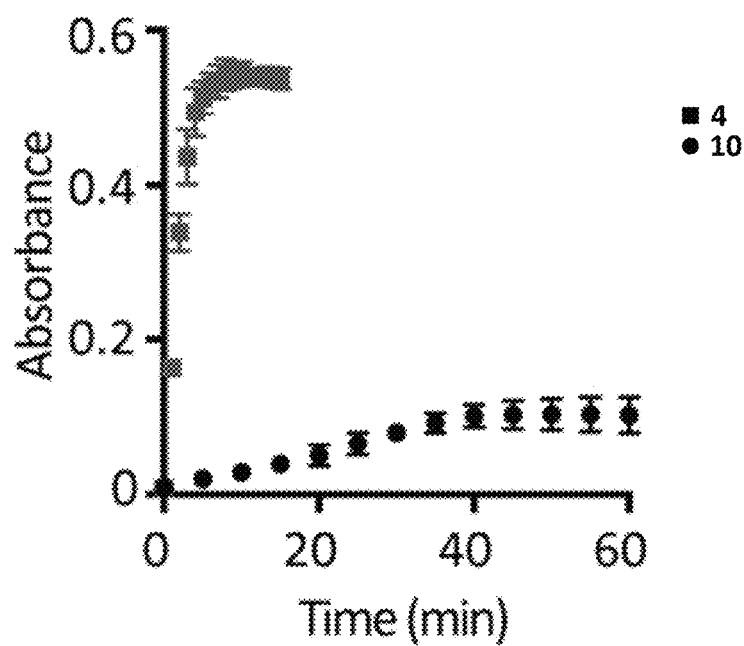
FIG. 8 is a graph showing ultraviolet recovery of 20 µM solutions of compound 4 (squares) and 10 (circles) in 4:1 PBS (50 mM, pH 7.4):DMSO following $NaBH_4$ reduction (2.5 mM in 1:1 DMSO:MeOH). Absorbance was measured at $\lambda_{max}$ (compound 4 at 640 nm and compound 10 at 660 nm as a function of time of 365 nm irradiation (5 mW/cm$^2$).

Compounds 4, 7, and 10 of Example 3 were evaluated. Most strikingly, the UV-light induced regeneration of compound 4 following $NaBH_4$ reduction was dramatically enhanced relative to unrestrained cyanines. Reduction of compound 4 with 2.0 equiv. of $NaBH_4$ (2.5 mM in 1:1 DMSO:MeOH) followed by photolysis of a 20 M solution in 4:1 PBS (50 mM, pH 7.4):DMSO with UV light (365 nm, 5 mW/cm$^2$) provided 38% maximal cyanine absorbance recovery with compound 4 (squares) after 5 min, but only a 6% maximal recovery after 30 minutes with compound 10 (circles) (FIG. 8). Absorbance was measured at $\lambda_{max}$ (compound 4 at 640 nm and compound 10 at 660 nm as a function of time of 365 nm irradiation (5 mW/cm$^2$).

Figure 9:
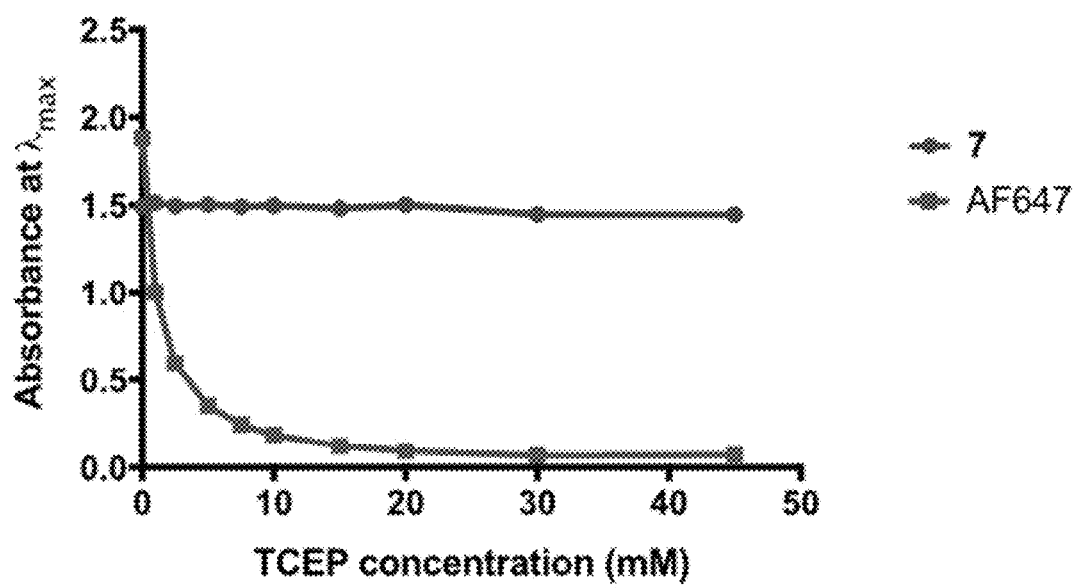
FIG. 9 is a graph showing the effect of TCEP addition on absorbance of compound 7 and AF647 (10 µM each). Absorbance at $\lambda_{max}$ (compound 7 at 670 nm and AF647 at 650 nm) as a function of TCEP concentration in Tris (0.20 M, pH 9.0).

The formation of phosphine and thiol adducts in chemical and single molecule imaging contexts was also evaluated. TCEP (tris(2-carboxyethyl)phosphine) was add to compound 7 and AF647 (Alexa Fluor 647, available through ThermoFisher Scientific) (10 μM each) (Vaughan et al., *JACS* 2013, 135(4):1197-1200). Absorbance at $\lambda_{max}$ (compound 7 at 670 nm and AF647 at 650 nm) as a function of TCEP concentration in Tris (0.20 M, pH 9.0). Compound 7 (circles) appeared resistant to the formation of polyene-heteroatom adducts (FIG. 9).

Example 5

Binding and Visualization of a Conformationally Restricted Phalloidin Conjugate The phalloidin conjugate 9 of Example 3 was applied to visualize cellular F-actin in initial wide-field studies. These efforts included comparisons to the commercially available Alexa Fluor 647-phalloidin conjugate (AF647-phalloidin), which has been used extensively. Reduction and UV-activation (370 nm) of compound 9 provided dramatically improved recovery relative to AF647-phalloidin. Photostability of compound 9 was nearly indistinguishable from that of AF647-phalloidin.

Figure 10:
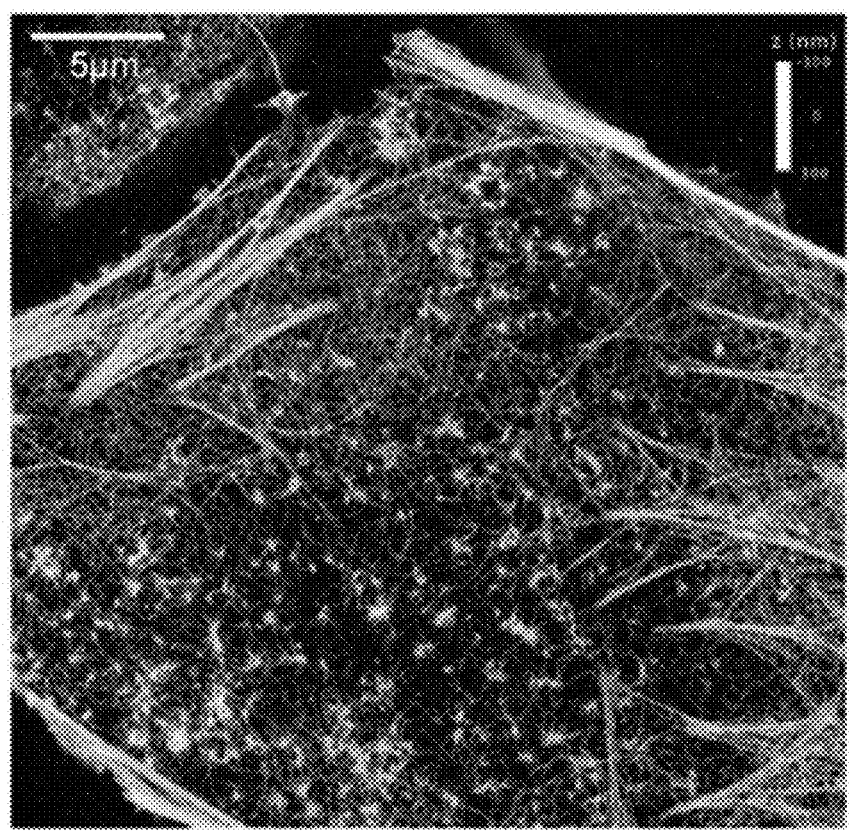
FIG. 10 is a color 3D TRABI_BP SMLM image of F-actin in a U2OS (human bone osteosarcoma epithelial) cell with compound 9, a conformationally restricted phalloidin-pentamethine cyanine fluorophore conjugate.
Figure 11:
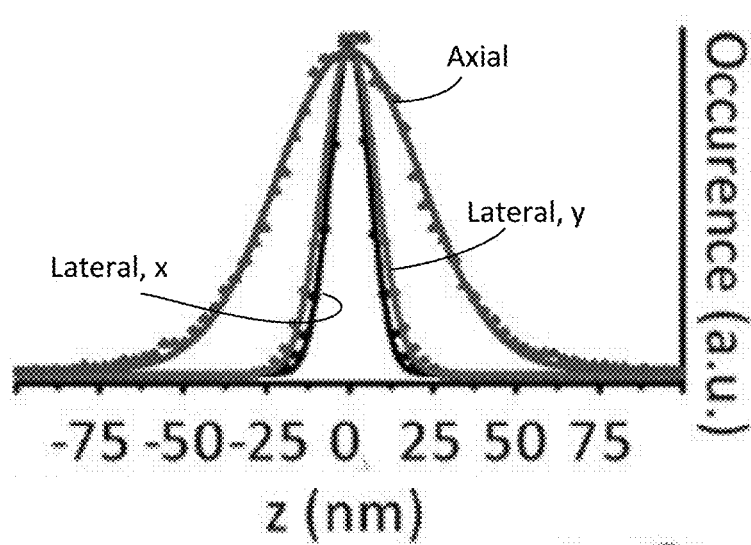
FIG. 11 shows lateral and axial localization precisions calculated from the image of FIG. 10. Marks indicate data points and solid lines indicate Gaussian fits to the data.
Figure 12:
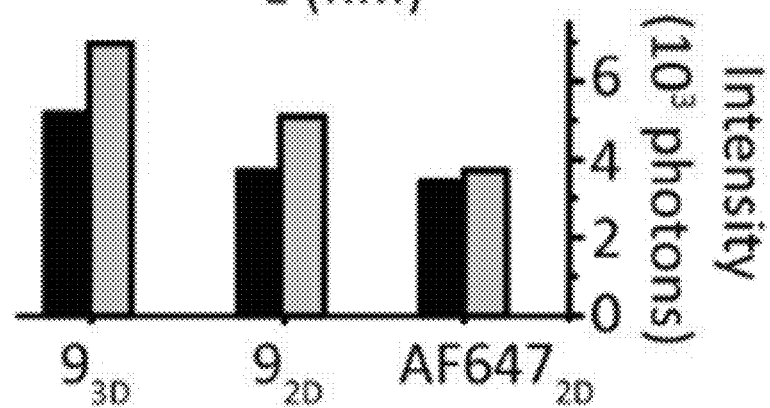
FIG. 12 is a bar graph showing a comparison of single molecule photon intensities regarding single frame (black) and tracked (grey) median values of data illustrated for compound $9_{3D}$ (left) and comparable measurements in 2D imaging modes of compound 9 (center) and AF647 (right) in standard dSTORM photoswitching buffer.
Figure 13:
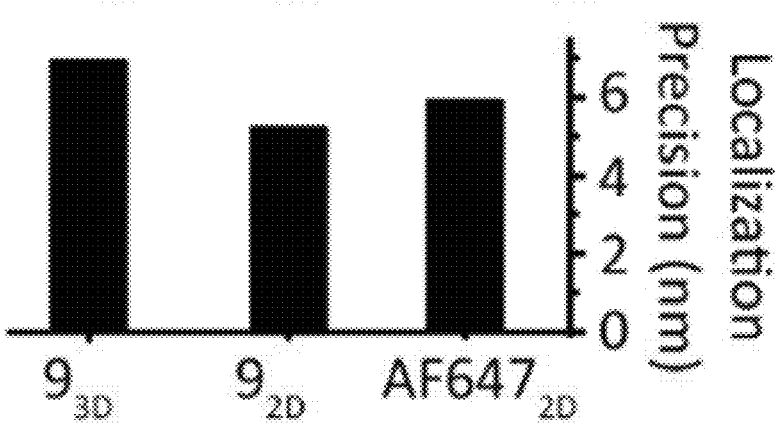
FIG. 13 is a bar graph showing experimentally determined lateral localization precisions of compound $9_{3D}$ (6.9 nm), compound $9_{2D}$ (5.2 nm) and AF647$_{2D}$ (5.9 nm).

The phalloidin conjugate 9 was evaluated with 3D PALM-like super-resolution imaging utilizing a biplane imaging scheme (BP) (Ram et al., *J., Biophys J* 2008, 95:6025) in combination with TRABI (Franke et al. *Nat Methods* 2017, 14:41) to simultaneously precisely quantify single molecule intensities and perform TRABI-BP imaging. Labeling and reduction (26 mM $NaBH_4$) with subsequent imaging in non-degassed phosphate buffered saline (PBS) provided high quality 3D super-resolved images of the actin cytoskeleton in a U2OS (human bone osteosarcoma epithelial) cell (FIG. 10). An average of 5181 photons per frame (median) were detected from single activated dyes, while tracking emitters that are active in consecutive frames yielded a conflated photon count of 6961 (median) before photobleaching or conversion to a nonfluorescent form. This corresponds to experimentally measured localization precisions of 5-7 nm laterally and ~20 nm axially. Excitation with either 640 or 660 nm can be employed, with the later providing somewhat improved photon yield. While the UV-laser can accelerate the recovery, the photoactivation rate obtained using solely the excitation laser (either 640 or 660) was sufficient to generate an emitter density suitable for SMLM. In SMLM experiments recovery of the reduced state proceeded almost quantitatively if 405 nm light was applied only for very short time periods. By contrast, when AF647-phalloidin was subjected to the reduction/recovery sequence, no reconstruction could be obtained. The images obtained with compound 9 using the reductive method were compared with AF647 under standard dSTORM buffer conditions. Conjugate 9 gave similar, if slightly improved, photon counts relative to AF647-phalloidin (9: 3721 per frame, 5107 tracked, AF647: 3422 per frame, 3737 tracked) and localization precisions of 5.2 & 5.9 nm respectively (FIGS. 11-13). FIG. 11 shows lateral and axial localization precisions calculated from the image of FIG. 10. FIG. 12 is a bar graph showing a comparison of single molecule photon intensities regarding single frame (black) and tracked (grey) median values of data illustrated for compound $9_{3D}$ (left) and comparable measurements in 2D imaging modes of compound 9 (center) and AF647 (right) in standard dSTORM photoswitching buffer. FIG. 13 is a bar graph showing experimentally determined lateral localization precisions of compound $9_{3D}$ (6.9 nm), compound $9_{2D}$ (5.2 nm) and AF647$_{2D}$ (5.9 nm).

Example 6

Tumor Visualization with Conformationally Restricted Cyanine Fluorophores

A subject having a tumor is identified and selected for treatment. The subject may be selected based on a clinical presentation and/or by performing tests to demonstrate presence of a tumor.

The subject is treated by administering a compound according to Formula I, a pharmaceutically acceptable salt thereof, or a pharmaceutical composition thereof at a dose determined by a clinician to be effective. The compound is administered by any suitable means, such as intravenous or subcutaneous injection. In some instances, the compound is injected directly into the tumor.

Visualization may be performed after a period of time sufficient to allow binding of the compound to the tumor. For example, irradiation may be performed several hours to several days after administration of the compound, such as from 1-7 days after administration of the compound. The administered compound is irradiated by targeted application of an effective quantity of light having a wavelength and a selected intensity suitable for inducing fluorescence of the cyanine fluorophore to a targeted portion of the subject, thereby exciting the cyanine fluorophore. Advantageously, the portion of the subject targeted for irradiation is proximate the tumor. Fluorescence of the compound is detected by any suitable method known to a person of ordinary skill in the art of fluorescence imaging. Fluorescence-guided surgery is used to determine the location and extent of tissue excision.

In some cases, the subject is suspected of having a tumor and presence of a tumor is confirmed by administering the compound to the subject and monitoring the compound's fluorescence at a suspected tumor site. Accumulation of the compound and fluorescence at the suspected tumor site diagnoses presence of a tumor.

Figure 14:
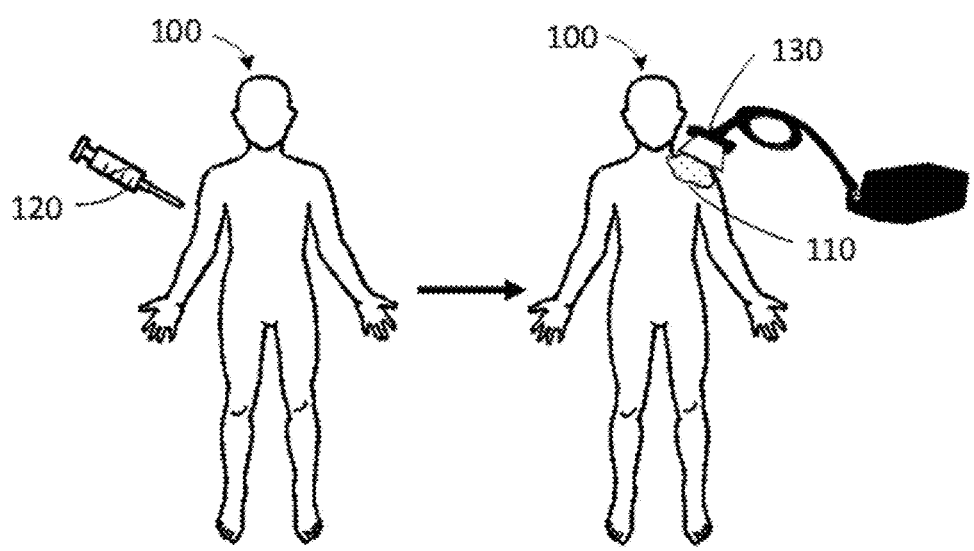
FIG. 14 is a schematic diagram illustrating one embodiment of a method for using the disclosed compounds according to Formula I by injection of the compound followed by targeted delivery of light of a desired wavelength to the external surface of the skin.

With reference to FIG. 14, a subject 100 with a tumor 110 may be treated with a compound according to Formula I that comprises an antibody or ligand capable of recognizing and binding to an antigen or receptor on a tumor cell surface. In the example shown in FIG. 14, the compound 120 is administered via intravenous injection. A period of time is allowed to elapse during which the compound preferentially accumulates at the tumor site as the antibody or ligand moiety binds to the tumor. A target portion of the subject subsequently is selectively irradiated with an effective amount of far-red or NIR light energy of a desired wavelength using an external light applicator 130. The light applicator 130 applies the light to a target area limited to the region of the tumor 110, thereby producing fluorescence of the compound. The tumor is visualized by detecting the fluorescence.

A therapeutically effective amount of a second agent may be co-administered with the compound according to Formula I or salt thereof. The compound (or salt thereof) and the second agent may be administered either separately or together in a single composition. The second agent may be administered by the same route or a different route. If administered concurrently, the compound (or salt thereof) and the second agent may be combined in a single pharmaceutical composition or may be administered concurrently as two pharmaceutical compositions. The second agent may be, for example, an anti-tumor agent or an angiogenesis inhibitor.

Example 6

Synthesis of a bis-Sulfonated Conformationally Restricted Cyanine Fluorophore

Figure 15:
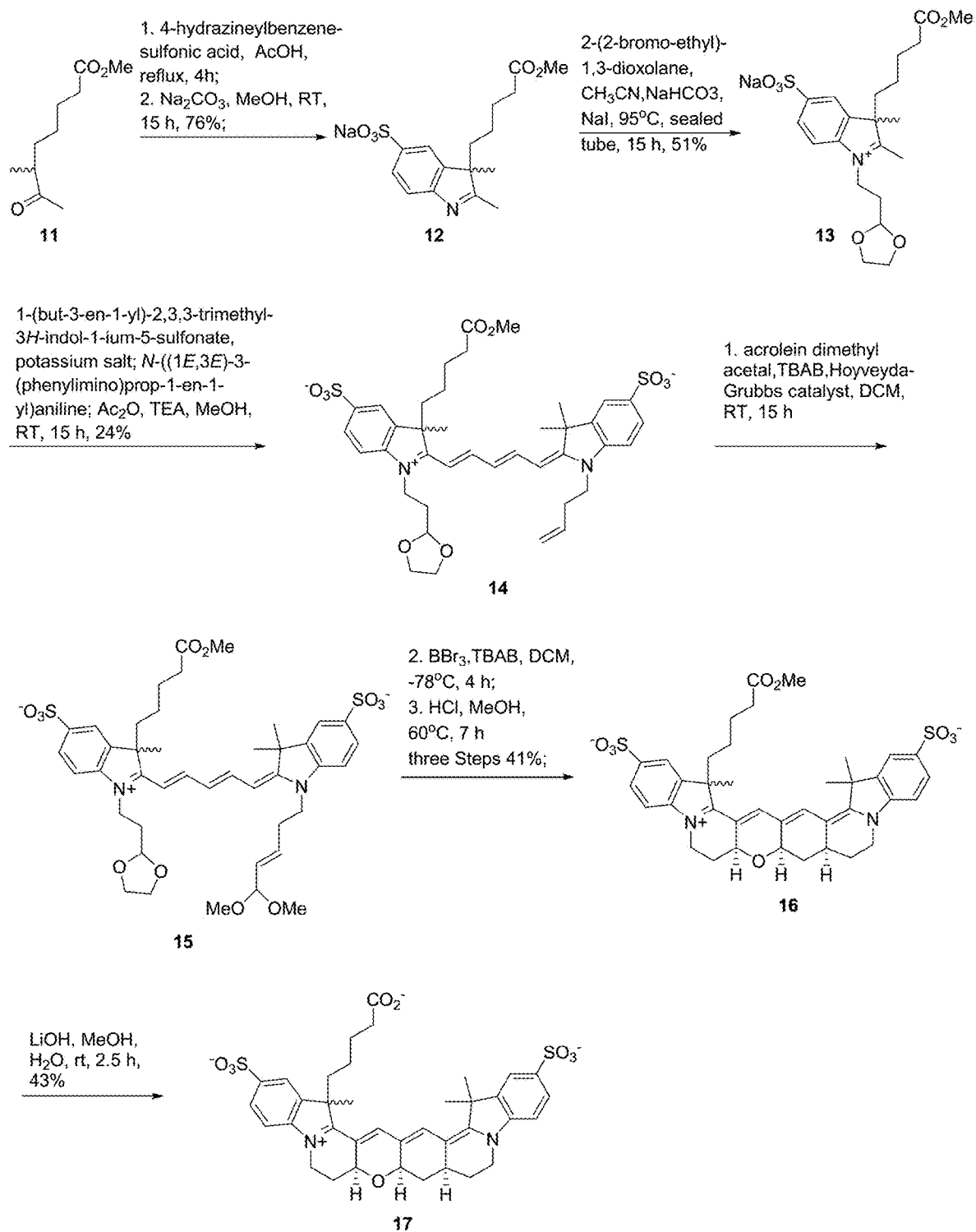
FIG. 15 is an exemplary synthetic scheme for preparing a bis-sulfonated, conformationally restricted pentamethine cyanine fluorophore.

The synthesis of conformational restricted cyanine dye 17 is described in FIG. 15. Starting from the racemic methyl 6-methyl-7-oxooctanoate 11, a Fisher indole synthesis was carried out with 4-hydrazineylbenzenesulfonic acid to produce 12 in 76% yield. The subsequent N-alkylation was performed in the presence of 2-(2-iodoethyl)-1,3-dioxolane at 95° C. to provide the product 3 in 51% yield. The cyanine skeleton was formed by reacting three moieties: compound 13, 1-(but-3-en-1-yl)-2,3,3-trimethyl-3H-indol-1-ium-5-sulfonate potassium salt, and N-((1E,3E)-3-(phenylimino)prop-1-en-1-yl)aniline to afford the desired product 14 in 24% yield. Cross metathesis was performed with acrolein dimethyl acetal under Hoyveyda-Grubbs catalyst and Bu$_4$NBr to produce 15. The key intramolecular Michael addition associated annulation cascade proceeded in the presence of BBr$_3$ and Bu$_4$NBr to yield diastereomeric mixtures, which was converted to two diastereomers 16 under the equilibration condition of HCl/MeOH at 60° C. The yield was 41% in the three steps. Hydrolysis of methyl ester with LiOH gave the final product 17 in 43% yield after the reverse phase C-18 column purification.

Experimental Details

Sodium 3-(5-methoxy-5-oxopentyl)-2,3-dimethyl-3H-indole5-sulfonate (12)

Methyl 6-methyl-7-oxooctanoate (1.86 g, 10 mmol) was added to a stirred solution of p-hydrazinobenzenesulfonic acid (2.24 g, 10 mmol) in acetic acid (6 mL). The solution was heated to reflux for 4 h, then cooled to room temperature. The solvents were evaporated. Na$_2$CO$_3$ (1.06 g, 10 mmol) was added to the residue dissolved in methanol (15 mL). The resulting mixture was stirred at room temperature for 15 h. The solvents were evaporated, and the residue was purified by reverse phase column chromatography to provide 12 (2.72 g, 7.6 mmol, 76%). $^1$H NMR (400 MHz, CD$_3$OD): δ 7.84-7.80 (m, 2H), 7.46 (d, 1H, J=7.8 Hz), 3.57 (s, 3H), 2.28 (s, 3H), 2.16 (dt, 2H, J=7.4, 2.3 Hz), 2.04-1.84 (m, 2H), 1.50-1.41 (m, 2H), 1.34 (s, 3H), 0.74-0.56 (m, 2H). LC-MS (ESI) 340 (M$^+$).

1-(2-(1,3-Dioxolan-2-yl)ethyl)-3-(5-methoxy-5-oxopentyl)-2,3-dimethyl-3H-indol-1-ium-5-sulfonate, Sodium Salt (13)

In a sealed vessel, compound 12 (2.25 g, 6.23 mmol) was combined with 2-(2-bromoethyl)-1,3-dioxolane (1.1 mL, 9.34 mmol), NaHCO$_3$ (1.57 g, 18.6 mmol), and NaI (1.40 g, 9.34 mmol) in CH$_3$CN (20 mL). The reaction was stirred at 95° C. under argon atmosphere for 15 h as the solution color turned into brown. The crude product was concentrated under reduced pressure and the residue was purified by reversed-phase column chromatography to afford 13 (1.45 g, 3.14 mmol, 51%). $^1$H NMR (400 MHz, CD$_3$OD): δ 7.61 (d, 1H, J=7.8 Hz), 7.50 (s, 1H), 6.62 (d, 1H, J=7.8 Hz), 4.97 (m, 1H), 4.03-3.93 (m, 4H), 3.71-3.65 (m, 2H), 3.58 (s, 3H), 2.19-2.10 (m, 3H), 2.06-2.20 (m, 2H), 1.96-1.90 (m, 2H), 1.56-1.46 (m, 2H), 1.43 (s, 3H), 1.05-0.82 (m, 2H). LC-MS (ESI) 440 (M$^+$).

1-(2-(1,3-Dioxolan-2-yl)ethyl)-2-((1E,3E)-5-((E)-1-(but-3-en-1-yl)-3,3-dimethyl-5-sulfonatoindolin-2-ylidene)penta-1,3-dien-1-yl)-3-(5-methoxy-5-oxopentyl)-3-methyl-3H-indol-1-ium-5-sulfonate (14)

Acetic anhydride (0.87 mL, 9.21 mmol) was added to a solution of 13 (2.10 g, 4.54 mmol), 1-(but-3-en-1-yl)-2,3,3-trimethyl-3H-indol-1-ium-5-sulfonate, potassium salt (1.51 g, 4.54 mmol), malonaldehyde bis(phenylimine) monohydrochloride (1.21 g, 5.45 mmol), and Et$_3$N (3.2 mL, 22.7 mmol) in MeOH (23 mL). While stirring at room temperature, additional acetic anhydride (0.87 mL, 9.21 mmol) was added every 30 minutes during the first 1.5 hours for a total of 3.48 mL (36.8 mmol). During the reaction, the solution color transitioned from red to green to purple and finally to dark blue. After 15 hours of total reaction time, LC/MS analysis revealed a mixture of the 3 possible cyanine products in an approximately 2:1:1 ratio of the unsymmetrical desired product to the undesired symmetrical cyanines. A solution of 2:1 diethyl ether/hexanes (180 mL) was added and a precipitate formed, which was collected by centrifugation. This solid was triturated three times with of 2:1 diethyl ether/hexanes and after drying in vacuo the dark blue residue was purified with reverse-phase chromatography to provide 14 (946 mg, 1.09 mmol, 24%) as a dark blue solid. $^1$H NMR (400 MHz, CD$_3$OD): δ 8.35-8.25 (m, 2H), 7.89-7.85 (m, 4H), 7.35 (dd, 2H, J=20.1, 8.4 Hz), 6.72 (m, 1H), 6.40 (t, 2H, J=12.9 Hz), 5.89 (m, 1H), 5.04-4.95 (m 3H), 4.26-4.23 (m, 4H), 3.96-3.93 (m, 2H), 3.85-3.81 (m, 2H), 3.53 (s, 3H), 2.62-2.57 (m, 2H), 2.47 (s, 1H), 2.23-2.12 (m, 5H), 1.74 (s, 3H), 1.73 (s, 3H), 1.70 (s, 3H), 1.50-1.42 (m, 2H), 0.93 (m, 1H), 0.63 (m, 1H). LC-MS (ESI) 769 (M$^+$).

(7aS,8aR,9aS)-20-(5-Methoxy-5-oxopentyl)-17,17,20-trimethyl-6,7,7a,8a,9,9a,10,11,17,20-decahydrobenzo[2',3']indolizino[8',7':5,6]pyrano[2,3-g]indolo[2,1-a]isoquinolin-5-ium-2,15-disulfonate (16)

Acrolein dimethyl acetal (1.16 mL, 0.98 mmol) was added to a solution of 4 (850 mg, 0.98 mmol), Hoyveyda- Grubbs catalyst 2$^{nd}$ generation (313 mg, 0.50 mmol) and tetrabutylammonium bromide (946 mg, 2.94 mmol) in anhydrous $CH_2Cl_2$ (50 mL). The flask was vacuumed and flushed with argon approximately every 30 min for 5 h. The solution was stirred for an additional 10 h. A solution of 1:1 diethylether/hexanes (360 mL) was added to the blue mixture and the precipitate was collected by centrifugation. After the second precipitation and centrifugation, the pellet was dried under high vacuum to afford 15 (694 mg, 75% yield) as a dark blue solid that was used without further purification. A dark blue solution of 15 (694 mg, 0.74 mmol) and tetrabutylammonium bromide (714 mg, 2.22 mmol) in $CH_2Cl_2$ (49 mL) was degassed and cooled to −78° C. under argon. $BBr_3$ solution (8.6 mL, 8.6 mmol, 1.0 M in $CH_2Cl_2$) was added slowly and the reaction color transitioned to red-brown. The reaction was stirred under argon with the temperature at −78° C. for 4 hours, at which time the reaction was quenched with the addition of $H_2O$ (40 mL) and immediately returned to a blue color. After warming to room temperature, the organic solvent was evaporated under reduced pressure. The remaining blue aqueous solution was purified by reverse-phase chromatography to yield a diastereomeric mixture product (367 mg). A diastereomeric mixture (367 mg, 0.50 mmol) was dissolved in MeOH (41 mL) and aqueous HCl (0.30 M, 120 mL). This reaction mixture was heated to 60° C. for 7 h over which time the color transitioned from dark blue to a green-blue color. After evaporation of solvents, the crude mixture was purified by reverse-phase chromatography to afford 6 (294 mg, 0.40 mmol, 41% yield) as a blue solid. $^1$H NMR (400 MHz, d6-DMSO): δ 8.00 (s, 1H), 7.93 (s, 1H), 7.82 (d, 1H, J=1.2 Hz), 7.72 (m, 1H), 7.64 (dd, 1H, J=8.2, 1.6 Hz), 7.60 (dd, 1H, J=8.2, 1.6 Hz), 7.26 (d, 1H, J=8.2 Hz), 7.16 (dd, 1H, J=8.2, 2.0 Hz), 4.56 (dd, 1H, J=11.3, 5.1 Hz), 4.48 (m, 1H), 4.30-4.18 (m, 2H), 3.84-3.77 (m, 2H), 3.26 (s, —OMe), 3.45 (s, —OMe), 2.70 (m, 1H), 2.46-2.30 (m, 3H), 2.28-2.12 (m, 4H), 1.83 (m, 1H), 1.70 (s, 3H), 1.69 (s, 3H), 1.65 (s, 3H), 1.45-1.28 (m, 3H), 0.82 (m, 1H), 0.57 (m, 1H). LC-MS (ESI) 735 (M$^+$).

5-((7aS,8aR,9aS)-17,17,20-trimethyl-2,15-disulfonato-6,7,7a,8a,9,9a,10,11,17,20-decahydrobenzo[2',3']indolizino[8',7':5,6]pyrano[2,3-g]indolo[2,1-a]isoquinolin-5-ium-20-yl)pentanoate (17)

Compound 16 (239 mg, 0.32 mmol) was dissolved in MeOH (14 mL) and aqueous LiOH (2.0 M, 14 mL). The resulting blue solution was stirred at room temperature for 2.5 hours. Saturated aqueous $NaHCO_3$ (12.0 mL) was added to quench the reaction. After the removal of MeOH in vacuo, the crude aqueous mixture was purified by reverse-phase chromatography to afford 17 (101 mg, 0.14 mmol, 43% yield) as a blue solid. $^1$H NMR (400 MHz, d6-DMSO): δ 8.01 (d, 1H, J=3.9 Hz), 7.92 (s, 1H), 7.82 (d, 1H, J=1.2 Hz), 7.72 (m, 1H), 7.63 (dd, 1H, J=8.2, 1.6 Hz), 7.60 (dd, 1H, J=8.2, 1.6 Hz), 7.25 (d, 1H, J=8.2 Hz), 7.16 (dd, 1H, J=8.4, 3.7 Hz), 4.56 (m, 1H), 4.48 (td, 1H), 4.30-4.19 (m, 2H), 3.84-3.76 (m, 2H), 2.70 (m, 1H), 2.42-2.30 (m, 3H), 2.26-2.17 (m, 2H), 2.08-2.01 (m, 2H), 1.84 (m, 1H), 1.69 (s, 3H), 1.68 (s, 3H), 1.65 (s, 3H), 1.40-1.30 (m, 1H), 0.83 (m, 1H), 0.63 (m, 1H). LC-MS (ESI) 721 (M).

VII. REPRESENTATIVE EMBODIMENTS

Certain representative embodiments are disclosed in the following numbered clauses.

1. A compound having a chemical structure according to Formula I, or a stereoisomer or pharmaceutically acceptable salt thereof:

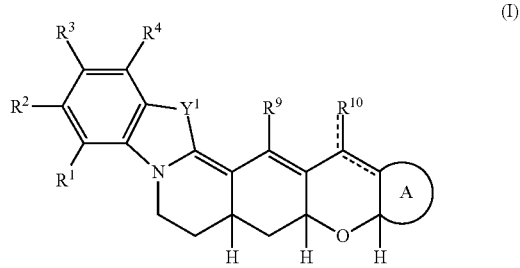

wherein A is

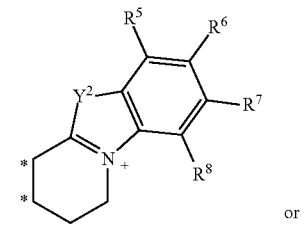

or

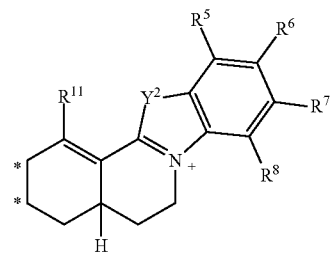

or H wherein each "*" designates an attachment point of A; the bonds represented by " ---- " are single or double bonds as needed to satisfy valence requirements; $R^1$-$R^9$ and $R^{11}$ independently are H, deuterium, alkyl, heteroalkyl, —N($R^a$)$_2$, sulfonate, alkyl sulfonate, amino, aminoalkyl, —C(O)O$R^a$, or a group comprising a conjugatable moiety, a targeting agent, or a drug, where $R^a$ is H, deuterium, alkyl or heteroalkyl; $R^{10}$ is H, deuterium, O, alkyl, aryl, amino, sulfonate, triflate, —C(O)O$R^b$, —O$R^b$, —N($R^b$)$_2$, heteroalkyl, heteroaryl, or a group comprising a conjugatable moiety, a targeting agent, or a drug, where each $R^b$ independently is H, deuterium, alkyl, heteroalkyl, aryl, or heteroaryl; and $Y^1$ and $Y^2$ independently are C($R^c$)$_2$, N($R^d$), S, O, or Se, wherein each $R^c$ independently is H, deuterium, alkyl, —(OCH$_2$CH$_2$)$_x$OH where x is an integer ≥2, or a group comprising a conjugatable moiety, a targeting agent, or a drug, and each $R^d$ independently is H, deuterium, alkyl, or heteroalkyl.

2. The compound of clause 1, having a chemical structure according to Formula IA, IB, IC, or ID:

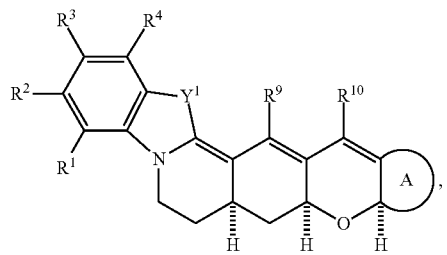
(IA)

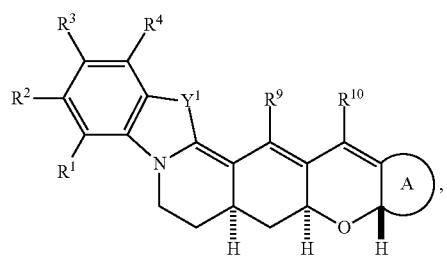
(IB)

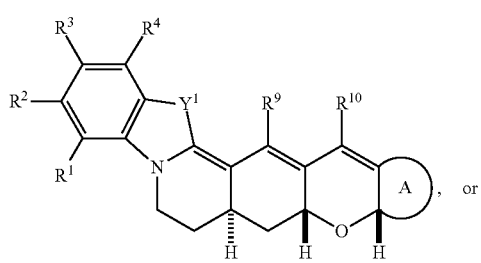
(IC), or

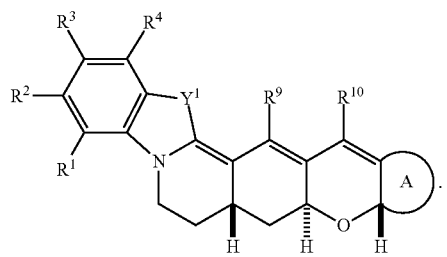
(ID).

3. The compound of clause 1 or clause 2, wherein at least one of $R^3$ and $R^6$ is sulfonate, —C(O)OR$^a$, or a group comprising a conjugatable moiety, a targeting agent, or a drug.

4. The compound of any one of clauses 1-3, wherein $Y^1$ and $Y^2$ are C(R$^c$)$_2$ and each R$^c$ independently is $C_1$-$C_3$ alkyl, —(CH$_2$)C(O)R, or H, wherein n is an integer ≥1 and R$^e$ is a conjugatable moiety, a targeting agent, or a drug.

5. The compound of clause 4, wherein $Y^1$ and $Y^2$ are C(CH$_3$)$_2$.

6. The compound of any one of clauses 1-5, wherein $R^1$, $R^2$, $R^4$, $R^5$, $R^7$, and $R^8$ are H.

7. The compound of any one of clauses 1-6, having a chemical structure according to Formula II or Formula III:

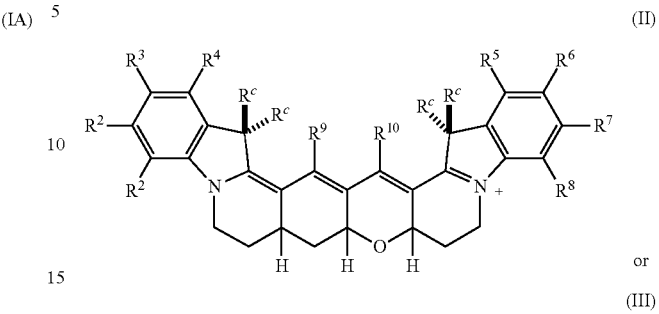
(II)

or

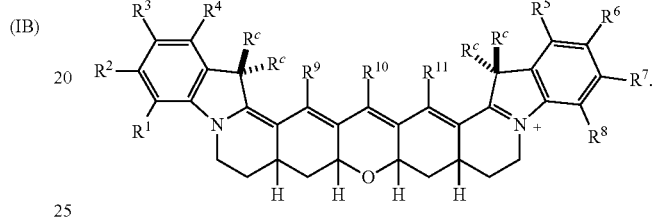
(III)

8. The compound of clause 7, wherein each R$^c$ is —CH$_3$.

9. The compound of clause 7 or clause 8, wherein the compound has a chemical structure according to Formula II and $R^1$-$R^{10}$ are H.

10. The compound of clause 7 or clause 8, wherein $R^1$, $R^2$, $R^4$, $R^5$, and $R^7$-$R^{11}$ are H, and $R^3$ and $R^6$ independently are —SO$_3$ or —CO$_2$R$^a$.

11. The compound of clause 7 or clause 8, wherein the compound has a chemical structure according to Formula II, $R^9$ and $R^{10}$ are H, and at least one of $R^3$ and $R^6$ is a group comprising a conjugatable moiety, a targeting agent, or a drug.

12. The compound of clause 7 or clause 8, wherein the compound has a chemical structure according to Formula III, $R^1$-$R^9$ and $R^{11}$ are H, and $R^{10}$ is H, O, triflate, aryl, —OR$^b$, or —N(R$^b$)$_2$.

13. The compound of clause 7 or clause 8, wherein the compound has a chemical structure according to Formula III, $R^9$ and $R^{11}$ are H, and at least one of $R^3$, $R^6$, and $R^{10}$ is a group comprising a conjugatable moiety, a targeting agent, or a drug.

14. A pharmaceutical composition comprising a compound according to any one of clauses 1-13 and a pharmaceutically acceptable carrier.

15. A method for making a compound according to clause 1 wherein A is

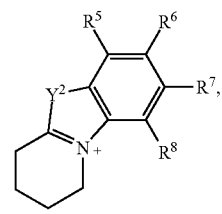

the method comprising: combining a solution comprising a compound according to Formula IV with 3-buten-1-yl trifluoromethanesulfonate to produce a compound according to Formula V

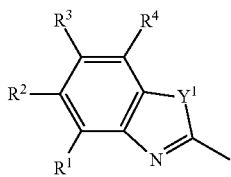
(IV)

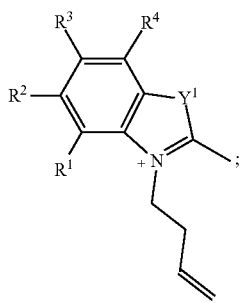
(V)

combining a solution comprising the compound according to Formula V and a compound according to Formula VI with N-((1E,3Z)-3-(phenylamino)propo-1-en-1-yl)aniline to form a compound according to Formula VII

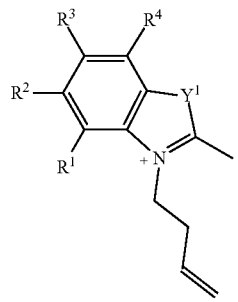
(V)

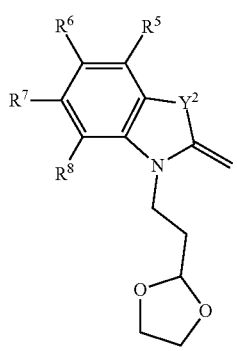
(VI)

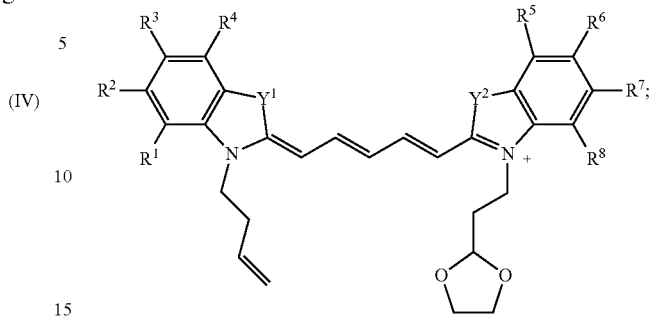
(VII)

combining a solution comprising the compound according to Formula VII with 3,3-dimethoxy-1-propene in the presence of a ruthenium catalyst to provide a compound according to Formula VIII

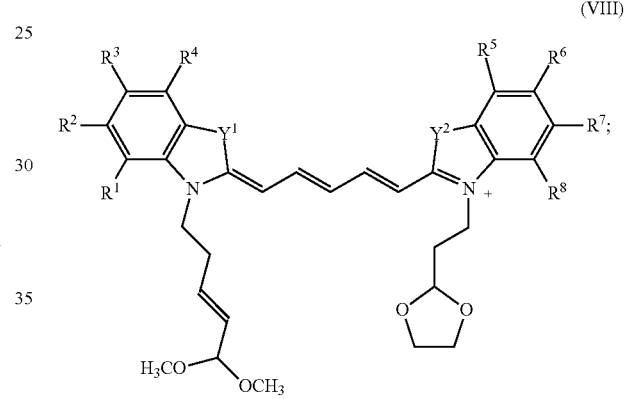
(VIII)

and combining the compound according to Formula VIII with (i) a mixture of CHCl$_3$ and H$_2$SO$_4$ or (ii) BBr$_3$ in CH$_2$Cl$_2$ to provide a compound according to Formula IX:

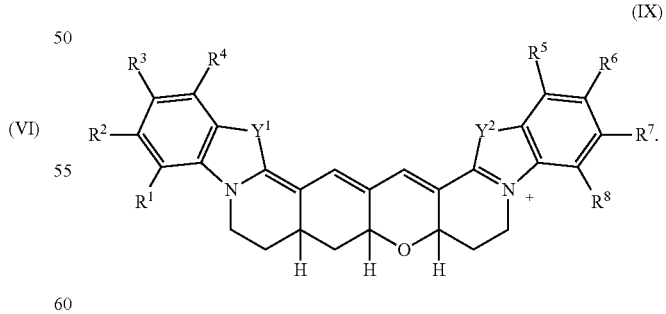
(IX)

16. The method of clause 15, wherein the ruthenium catalyst is (1,3-bis-(2,4,6-trimethylphenyl)-2-imidazolidinylidene)dichloro(o-isopropoxyphenylmethylene)ruthenium.

17. A method for making a compound according to clause 1 wherein A is

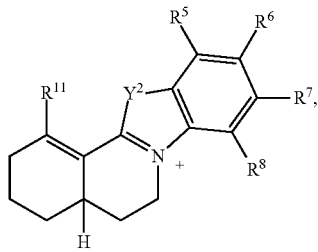

the method comprising: combining a solution comprising a compound according to Formula IV with 3-buten-1-yl trifluoromethanesulfonate to produce a compound according to Formula V

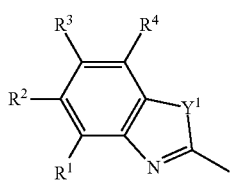
(IV)

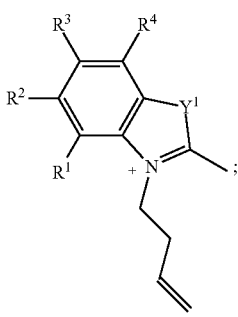
(V)

combining a solution comprising a compound according to Formula X with 3-buten-1-yl trifluoromethanesulfonate to produce a compound according to Formula XI

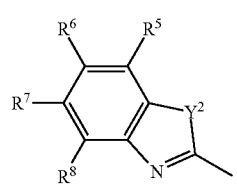
(X)

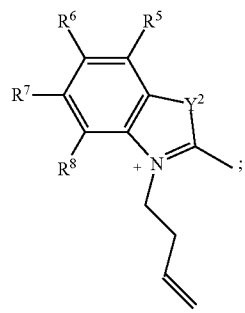
(XI)

combining a solution comprising the compound according to Formula V and the compound according to Formula XI, wherein the compounds according to Formula V and Formula XI may be the same or different, with (1E,4E)-1,5-bis(dimethylamino)-penta-1,4-dien-3-one to produce a compound according to Formula XII

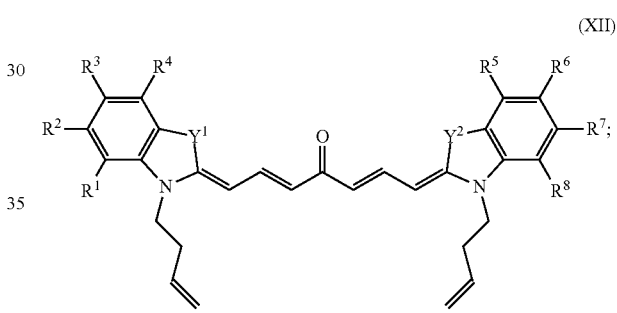
(XII)

combining a solution comprising the compound according to Formula XII with 3,3-dimethoxy-1-propene in the presence of a ruthenium catalyst to provide a compound according to Formula XIII

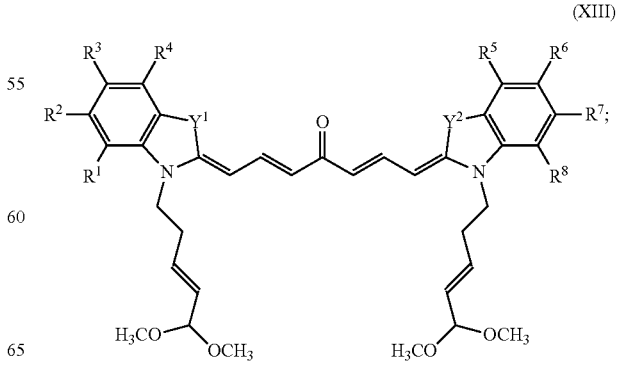
(XIII)

and combining the compound according to Formula XIII with a solution of 1 N HCl in tetrahydrofuran to provide a compound according to Formula XIV

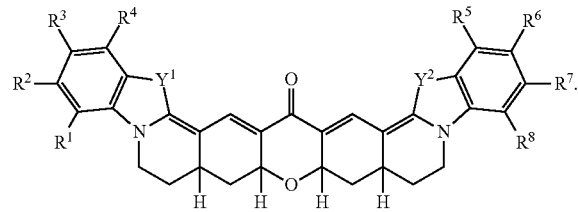

(XIV)

18. The method of clause 17, wherein the ruthenium catalyst is (1,3-bis-(2,4,6-trimethylphenyl)-2-imidazolidinylidene)dichloro(o-isopropoxyphenyl-methylene)ruthenium.

19. The method of clause 17, further comprising combining a solution comprising the compound according to Formula XIV with trifluoromethanesulfonic anhydride (Tf$_2$O) to provide a compound according to Formula XV:

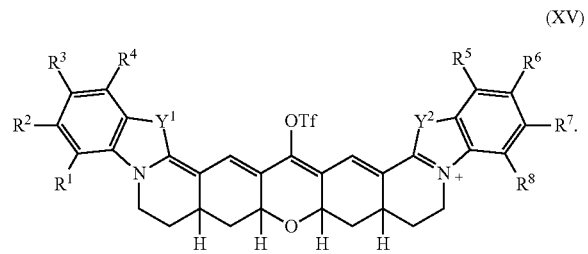

(XV)

20. The method of clause 19, further comprising combining a solution comprising the compound according to Formula XV with $R^g$—C$_6$H$_4$—B(OH)$_2$ in the presence of a palladium catalyst to provide a compound according to Formula XVI:

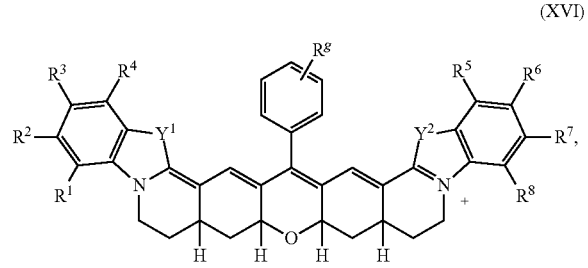

(XVI)

where $R^g$ is $R^a$, —COOR$^a$, or —OR$^a$, where $R^a$ is H, deuterium, alkyl or heteroalkyl.

21. The method of clause 19, further comprising combining a solution comprising the compound according to Formula XV with an amine having a formula NH(R$^{20}$)(R$^{21}$) to provide a compound according to formula XVII:

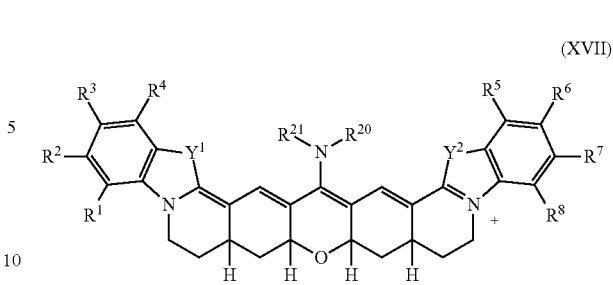

(XVII)

where $R^{20}$ and $R^{21}$ independently are H, deuterium, alkyl, heteroalkyl, aryl or heteroaryl.

22. The method of clause 21, wherein (i) $R^{20}$ is —(CR$^h_2$)$_n$—CH$_2$OH where each $R^h$ independently is H, deuterium, halo, alkyl, or aryl, and n is 1, 2, 3, or 4, and (ii) $R^{21}$ is H, deuterium, alkyl, heteroalkyl, aryl, or heteroaryl, the method further comprising combining a solution comprising the compound according to Formula XVII with a compound comprising an electrophilic group $R^{22}$ under basic conditions to provide a compound according to Formula XVIII:

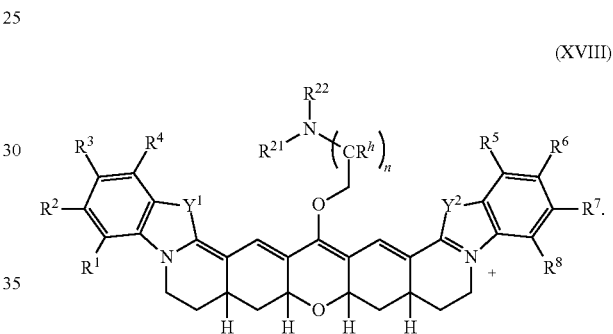

(XVIII)

23. A method for using a compound according to any one of clauses 1-13 wherein at least one of $R^1$-$R^{11}$ comprises a targeting agent, the method comprising: combining the compound with a sample comprising a target capable of binding with the targeting agent under conditions effective to provide binding of the targeting agent and the target; and imaging the target by visualizing the compound bound to the target.

24. The method of clause 23, wherein visualizing the compound comprises: irradiating the sample with targeted application of a quantity of light having a wavelength in the visible or near-infrared range and a selected intensity, wherein the quantity of light is sufficient to produce fluorescence of the compound; and detecting any fluorescence emitted by the compound.

25. The method of clause 23 or clause 24, wherein combining the compound with the sample is performed in vitro, ex vivo, or in vivo.

26. The method of any one of clauses 23-25, further comprising combining the compound with a reducing agent prior to imaging the target.

27. The method of any one of clauses 23-26, wherein the sample is a tissue sample, a biological fluid, or a target area within a subject.

28. The method of clause 27, wherein the sample is a target area within a subject, the method further comprising: administering the compound, or a pharmaceutical composition comprising the compound to the subject; subsequently irradiating the compound by targeted application of the quantity of light to a targeted portion of the subject; and detecting any fluorescence from the compound in the targeted portion of the subject.

29. The method of clause 28, wherein the target area is a tumor site and the targeted portion of the subject includes the tumor site, the method further comprising excising at least a portion of the tumor from the subject after detecting the fluorescence in the targeted portion of the subject.

30. A method for detecting reactive oxygen species, the method comprising: combining a compound according to any one of clauses 1-13 with a reducing agent to provide a reduced compound; contacting a sample with the reduced compound, whereby the reduced compound is oxidized to regenerate the compound according to any one of clauses 1-13 if reactive oxygen species (ROS) are present in the sample; irradiating the sample with a quantity of light having a wavelength in the visible or near-infrared range and a selected intensity, wherein the quantity of light is sufficient to produce fluorescence if the reduced compound has been oxidized by the ROS to regenerate the compound according to any one of clauses 1-13; and detecting any fluorescence emitted by the compound according to any one of clauses 1-13, wherein fluorescence indicates the presence of ROS in the sample.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound having a chemical structure according to Formula I, or a stereoisomer or pharmaceutically acceptable salt thereof:

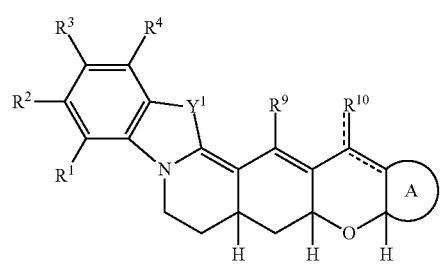

(I)

wherein A is

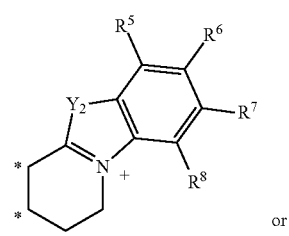

or

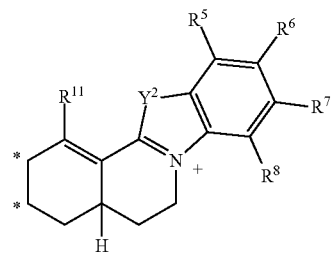

-continued wherein each "*" designates an attachment point of A;

the bonds represented by "----" are single or double bonds as needed to satisfy valence requirements;

$R^1$, $R^2$, $R^4$, $R^5$, $R^7$, and $R^8$ are H;

$R^3$, $R^6$, $R^9$ and $R^{11}$ independently are H, sulfonate, —N(R$^a$)$_2$, deuterium, alkyl, heteroalkyl, alkyl sulfonate, aminoalkyl, —C(O)OR$^a$, trityl, or a group comprising a conjugatable moiety, a targeting agent, or a drug, where each R$^a$ independently is H, deuterium, alkyl, or heteroalkyl;

$R^{10}$ is H, deuterium, O, alkyl, aryl, amino, sulfonate, triflate, —C(O)OR$^b$, —OR$^b$, —N(R$^b$)$_2$, heteroalkyl, heteroaryl, trityl, or a group comprising a conjugatable moiety, a targeting agent, or a drug, where each R$^b$ independently is H, deuterium, alkyl, heteroalkyl, aryl, or heteroaryl; and $Y^1$ and $Y^2$ independently are C(R$^c$)$_2$, wherein each R$^c$ independently is alkyl, H, deuterium, —(OCH$_2$CH$_2$)$_x$OH where x is an integer ≥2, trityl, or a group comprising a conjugatable moiety, a targeting agent, or a drug.

2. The compound of claim 1, wherein at least one of $R^3$, $R^6$, $R^9$-$R^{11}$, $Y^1$ or $Y^2$ comprises a group comprising a targeting agent or a drug.

3. The compound of claim 1, having a chemical structure according to Formula II or Formula III:

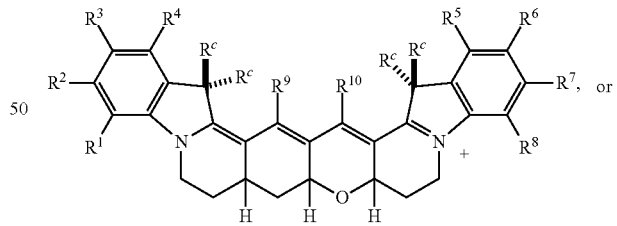

(II)

or

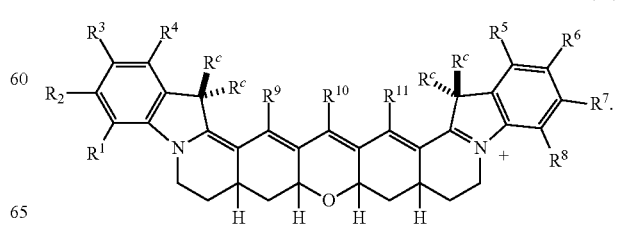

(III)

4. The compound of claim 3, wherein:
the compound has a chemical structure according to Formula II, $R^9$ and $R^{10}$ are H, and at least one of $R^3$ and $R^6$ is a group comprising a targeting agent or a drug; or
the compound has a chemical structure according to Formula III, $R^9$ and $R^{11}$ are H, and at least one of $R^3$, $R^6$, and $R^{10}$ is a group comprising a targeting agent or a drug.

5. The compound of claim 1, wherein at least one of $R^3$, $R^6$, $R^9$-$R^{11}$, $Y^1$ or $Y^2$ comprises a group comprising a targeting agent, the targeting agent comprising an antibody, a ligand, a peptide, or a nucleic acid strand.

6. The compound of claim 5, wherein the group comprising the targeting agent is —$(CH_2)_nC(O)R^e$, —$(CH_2)_nN(H)R^e$, —$(CH_2)_nN(H)C(O)R^e$, —$(CH_2)_nC(O)N(H)R^e$, —$(CH_2)_nC(O)SR^e$, —$C(O)R^e$, —$C(O)N(H)R^e$, —$C(O)N(H)(CH_2CH_2O)_m(CH_2)_nC(O)R^e$, —$N(H)C(O)R^e$, —$N(H)R^e$, or —$SR^e$, where
m is an integer ≥1;
n is an integer ≥1; and
$R^e$ is the targeting agent.

7. The compound of claim 5, wherein the targeting agent is phalloidin or an antibody.

8. The compound of claim 7, wherein the antibody is panitumumab, trastuzumab, pertuzumab, or brentuximab.

9. The compound of claim 1, wherein at least one of $R^3$, $R^6$, $R^9$-$R^{11}$, $Y^1$ or $Y^2$ comprises a group comprising a drug, the group having a formula —$L_1$-C(O)—$X^1$-drug, where:
$L_1$ is a linker moiety or is absent; and
$X^1$ is O, N(H), or N(CH$_3$).

10. The compound of claim 9, wherein $L_1$ is absent, O, or aryl or heteroaryl substituted with at least one substituent comprising a substituted or unsubstituted aliphatic or heteroaliphatic moiety, wherein the aryl or heteroaryl ring is the site of attachment to the remainder of the compound.

11. The compound of claim 9, wherein the group comprising the drug is:

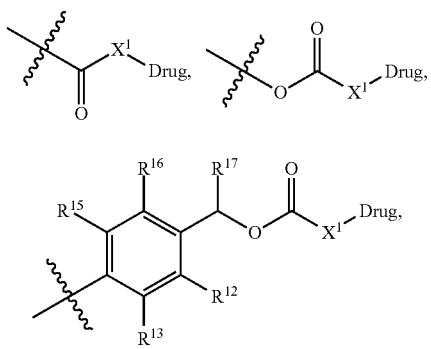

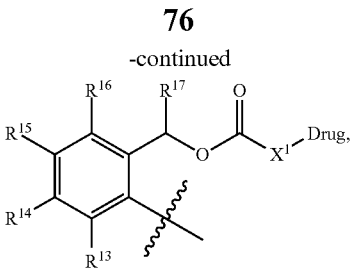

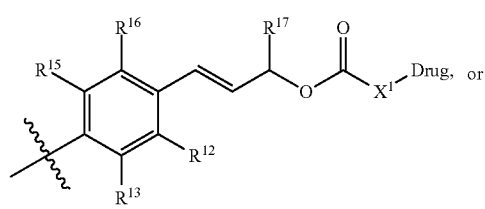

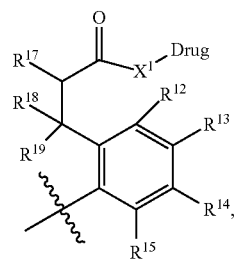

where
$X^1$ is O, N(H), or N(CH$_3$); and
$R^{12}$-$R^{19}$ independently are H, alkyl, —NO$_2$, —NR$^f_2$, —NR$^f_3{}^+$, alkoxy, or sulfonate, wherein each R$^f$ independently is H, halo, or alkyl.

12. The compound of claim 11, wherein $R^{12}$-$R^{19}$ are H.

13. The compound of claim 9, wherein the group comprising the drug is —C(O)—$X^1$-drug.

14. The compound of claim 1, wherein the compound is:

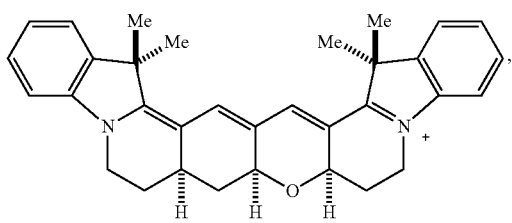

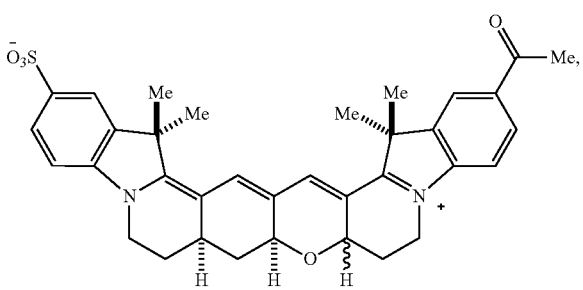

-continued
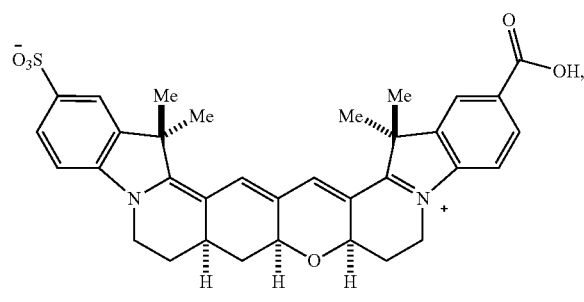
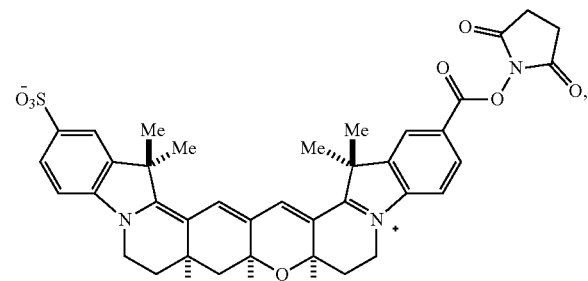
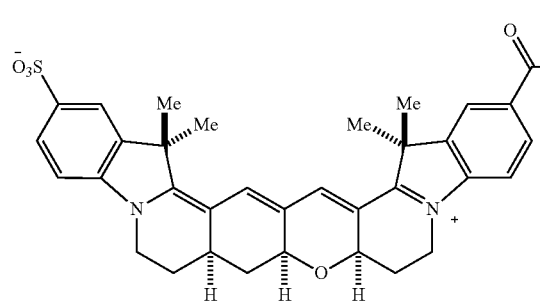
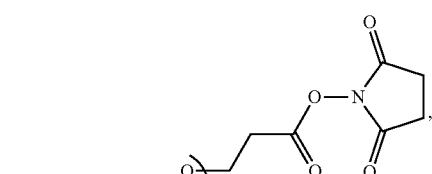
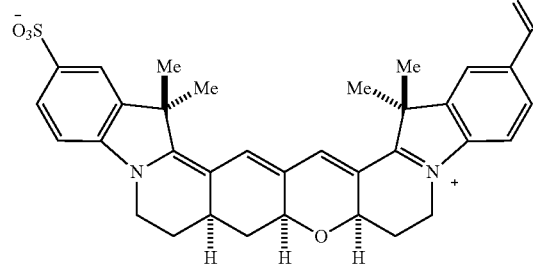
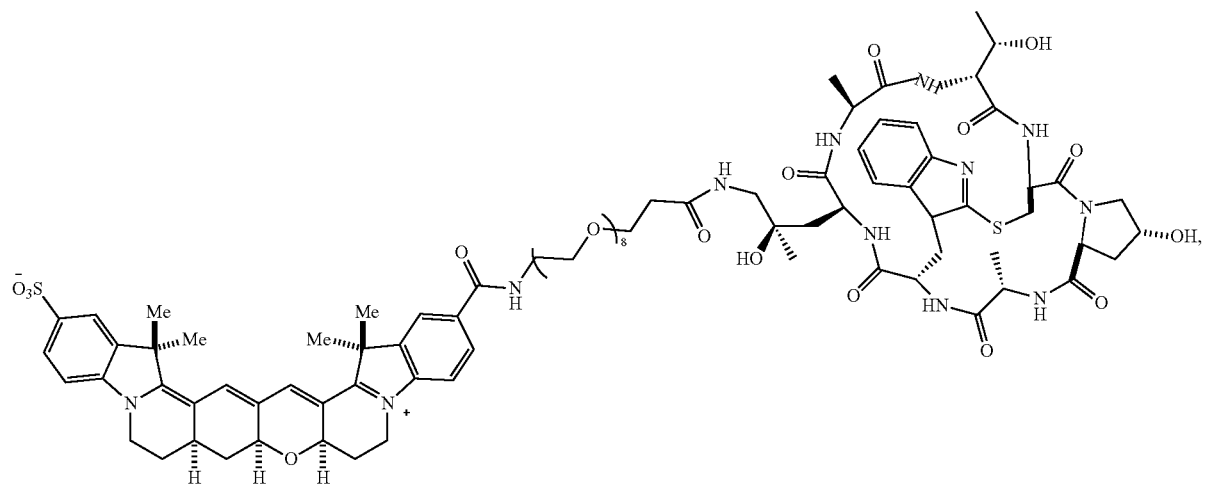

-continued

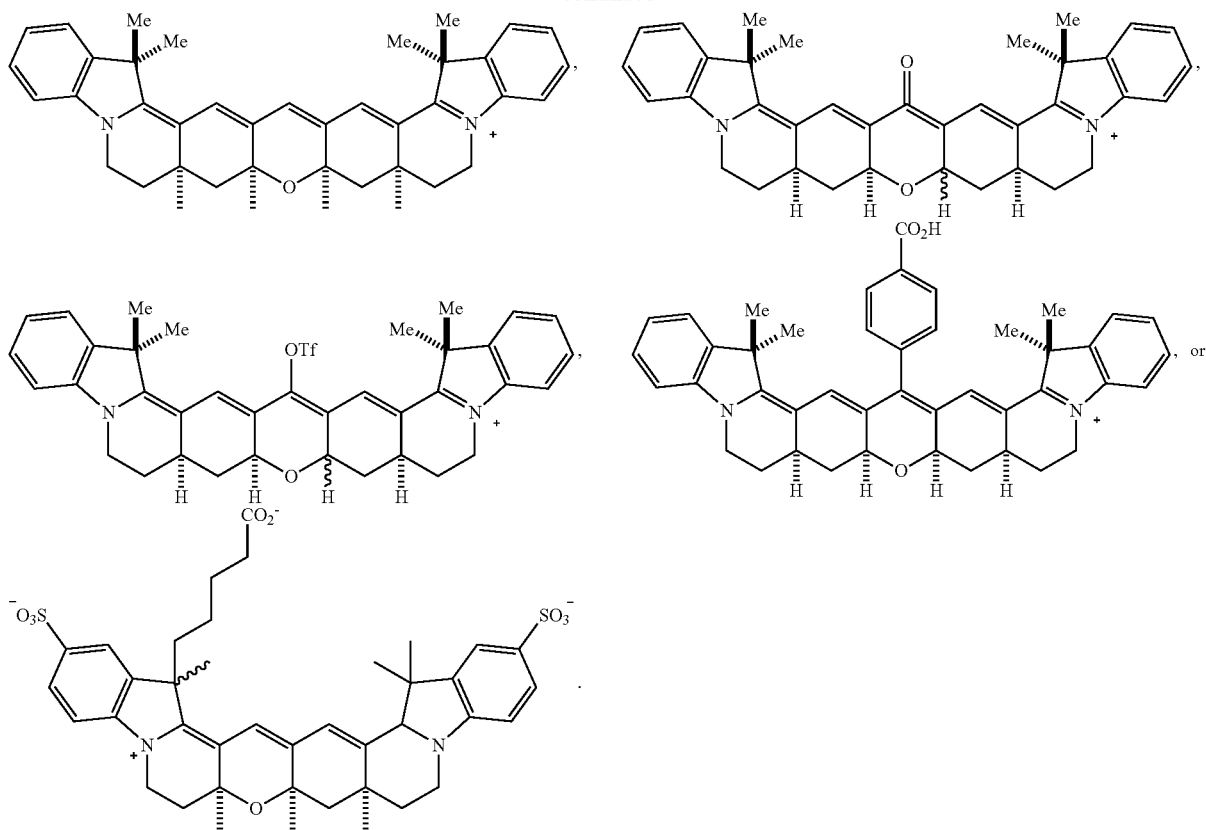

15. A pharmaceutical composition comprising a compound according to claim 1 and a pharmaceutically acceptable carrier.

16. The pharmaceutical composition of claim 15, wherein at least one of $R^3$, $R^6$, $R^9$-$R^{11}$, $Y^1$ or $Y^2$ comprises a group comprising a drug or a targeting agent.

17. A method for using a compound according to claim 1, wherein at least one of $R^3$, $R^6$, $R^9$-$R^{11}$, $Y^1$ or $Y^2$ comprises a group comprising a targeting agent, the method comprising:
    combining the compound with a sample comprising a target that binds with the targeting agent under conditions effective to provide binding of the targeting agent and the target; and
    imaging the target by visualizing the compound bound to the target, wherein visualizing the compound comprises
        irradiating the sample with targeted application of a quantity of light having a wavelength in the visible, far-red, or near-infrared range and a selected intensity, wherein the quantity of light is sufficient to produce fluorescence of the compound, and
    detecting any fluorescence emitted by the compound.

18. The method of claim 17, further comprising combining the compound with a reducing agent prior to imaging the target.

19. The method of claim 17, wherein the sample is a target area within a subject, the method further comprising:
    administering the compound or a pharmaceutical composition comprising the compound to the subject;
    subsequently irradiating the compound by targeted application of the quantity of light to a targeted portion of the subject; and
    detecting any fluorescence from the compound in the targeted portion of the subject.

20. The method of claim 19, wherein the target area is a tumor site and the targeted portion of the subject includes the tumor site, the method further comprising excising at least a portion of the tumor from the subject after detecting the fluorescence in the targeted portion of the subject.

* * * * *